United States Patent
Lowry

(10) Patent No.: US 10,828,289 B2
(45) Date of Patent: Nov. 10, 2020

(54) HAIR FOLLICLE STEM CELL ACTIVATION AND HAIR GROWTH

(71) Applicant: THE REGENTS OF THE UNIVERSITY OF CALIFORNIA, Oakland, CA (US)

(72) Inventor: William Lowry, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/327,966

(22) PCT Filed: Aug. 25, 2017

(86) PCT No.: PCT/US2017/048707
§ 371 (c)(1),
(2) Date: Feb. 25, 2019

(87) PCT Pub. No.: WO2018/039615
PCT Pub. Date: Mar. 1, 2018

(65) Prior Publication Data
US 2019/0224182 A1 Jul. 25, 2019

Related U.S. Application Data

(60) Provisional application No. 62/380,205, filed on Aug. 26, 2016.

(51) Int. Cl.
| | | |
|---|---|---|
| *A61K 8/98* | (2006.01) | |
| *A61K 31/426* | (2006.01) | |
| *A61K 31/497* | (2006.01) | |
| *A61Q 7/00* | (2006.01) | |
| *A61K 31/4439* | (2006.01) | |

(52) U.S. Cl.
CPC .......... *A61K 31/4439* (2013.01); *A61K 8/98* (2013.01); *A61K 31/426* (2013.01); *A61K 31/497* (2013.01); *A61Q 7/00* (2013.01)

(58) Field of Classification Search
CPC .... A61K 31/4439; A61K 8/98; A61K 31/426; A61K 31/497; A61Q 7/00
USPC ....................................................... 514/256
See application file for complete search history.

(56) References Cited

U.S. PATENT DOCUMENTS

| | | | |
|---|---|---|---|
| 2009/0156611 A1* | 6/2009 | Oinas | A61K 31/33 514/254.1 |
| 2011/0105436 A1 | 5/2011 | Turcotte et al. | |
| 2012/0108576 A1 | 5/2012 | Zhang et al. | |

FOREIGN PATENT DOCUMENTS

| | | |
|---|---|---|
| WO | WO-2012/065065 A1 | 5/2012 |
| WO | WO-2012/065065 A9 | 5/2012 |
| WO | WO-2016/138533 A2 | 9/2016 |
| WO | WO-2016/138533 A3 | 9/2016 |

OTHER PUBLICATIONS

Extended European Search Report dated Apr. 6, 2020, for European Patent Application No. 17844522.7, 5 pages.
Al-Muhammed, J. et al. (May-Jun. 1996). "In-vivo studies on dexamethasone sodium phosphate liposomes," J Microencapsul 13(3):293-306.
Chonn, A. et al. (Dec. 1995). "Recent advances in liposomal drug-delivery systems," *Curr Opin Biotechnol* 6(6):698-708.
Eyles, J.E. et al. (Jul. 1997). "Oral delivery and fate of poly(lactic acid) microsphere-encapsulated interferon in rats," J. Pharm. Pharmacol. 49(7):669-674.
Flores, A. et al. (Sep. 2017, e-published Aug. 14, 2017). "Lactate dehydrogenase activity drives hair follicle stem cell activation," *Nat Cell Biol* 19(9):1017-1026, 5 pages supplementary material.
Gao, Z.H. et al. (Jun. 1995). "Controlled release of a contraceptive steroid from biodegradable and injectable gel formulations: in vitro evaluation," Pharm. Res 12(6):857-863.
International Search Report dated Nov. 13, 2017, for PCT Application No. PCT/US2017/048707, filed Aug. 25, 2017, 2 pages.
Ostro, M.J. et al. (Aug. 1989). "Use of liposomes as injectable-drug delivery systems," *Am J Hosp Pharm* 46(8):1576-1587.
Rao K.P. (1995). "Recent developments of collagen-based materials for medical applications and drug delivery systems" *J. Biomater Sci. Polym. Ed.* 7(7):623-645.
Written Opinion dated Nov. 13, 2017, for PCT Application No. PCT/US2017/048707, filed Aug. 25, 2017, 3 pages.

* cited by examiner

*Primary Examiner* — Yevgeny Valenrod
(74) *Attorney, Agent, or Firm* — Edward D. Grieff; Mintz, Levin, Cohn, Ferris, Glovsky and Popeo, P.C.

(57) ABSTRACT

There are provided, inter alia, methods and compounds and method for inducing hair growth in a subject in need thereof.

22 Claims, 28 Drawing Sheets

HAIR FOLLICLE STEM CELL ACTIVATION AND HAIR GROWTH

CROSS-REFERENCES TO RELATED APPLICATIONS

This application is a Section 371 US national phase of International Application No. PCT/US2017/048707 filed Aug. 25, 2017, which claims the benefit of U.S. Provisional Application No. 62/380,205, filed Aug. 26, 2016, which is incorporated herein by reference in its entirety and for all purposes.

BACKGROUND OF THE INVENTION

Hair follicle stem cells (HFSCs) are often quiescent, long-lived cells that are responsible for maintaining the cellular homeostasis of the follicle. While often dormant, HFSCs quickly become activated to divide during a new hair cycle. The quiescence of HFSCs is regulated by a number of intrinsic and extrinsic mechanisms. In addition, there is a need in the art of hair growth and hair regeneration for safe and effective treatments. Disclosed herein, inter alia, solutions to these and other issues in the art.

BRIEF SUMMARY OF THE INVENTION

In an aspect is provided a method for inducing hair growth in a subject in need thereof, the method including administering to the subject an effective amount of a compound having the formula:

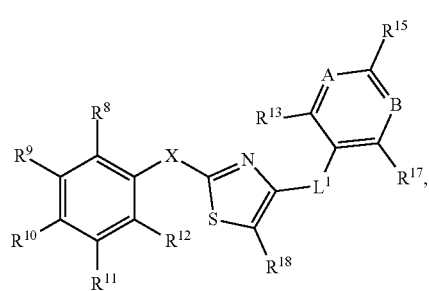

(III)

or a pharmaceutically acceptable salt thereof. For Formula (III), A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, $—CX^{8.1}_3$, $—CHX^{8.1}_2$, $—CH_2X^{8.1}$, $—CN$, $—SO_{n1}R^{8A}$, $—SO_{v1}NR^{8B}R^{8C}$, $—NHNR^{8B}R^{8C}$, $—ONR^{8B}R^{8C}$, $—NHC(O)NHNR^{8B}R^{8C}$, $—NHC(O)NR^{8B}R^{8C}$, $—N(O)_{m1}$, $—NR^{8B}R^{8C}$, $—C(O)R^{8D}$, $—C(O)OR^{8D}$, $—C(O)NR^{8B}R^{8C}$, $—OR^{8A}$, $—NR^{8B}SO_2R^{8A}$, $—NR^{8B}C(O)R^{8D}$, $—R^{8B}C(O)OR^{8D}$, $—NR^{8B}OR^{8D}$, $—OCX^{8.1}_3$, $—OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $—CX^{9.1}_3$, $—CHX^{9.1}_2$, $—CH_2X^{9.1}$, $—CN$, $—SO_{n1}R^{9A}$, $—SO_{v1}NR^{9B}R^{9C}$, $—NHNR^{9B}R^{9C}$, $—ONR^{9B}R^{9C}$, $—NHC(O)NHNR^{9B}R^{9C}$, $—NHC(O)NR^{9B}R^{9C}$, $—N(O)_{m1}$, $—NR^{9B}R^{9C}$, $—C(O)R^{9D}$, $—C(O)OR^{9D}$, $—C(O)NR^{9B}R^{9C}$, $—OR^{9A}$, $—NR^{9B}SO_2R^{9A}$, $—NR^{9B}C(O)R^{9D}$, $—NR^{9B}C(O)OR^{9D}$, $—NR^{9B}OR^{9D}$, $—OCX^{9.1}_3$, $—OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $—CX^{10.1}_3$, $—CHX^{10.1}_2$, $—CH_2X^{10.1}$, $—CN$, $—SO_{n1}R^{14}$, $—SO_{v1}NR^{10B}R^{10C}$, $—NHNR^{10B}R^{10C}$, $—ONR^{10B}R^{10C}$, $—NHC(O)NHNR^{10B}R^{10C}$, $—NHC(O)NR^{10B}R^{10C}$, $—N(O)_{m1}$, $—NR^{10B}R^{10C}$, $—C(O)R^{10D}$, $—C(O)OR^{10D}$, $—C(O)NR^{10B}R^{10C}$, $—OR^{10A}$, $—NR^{10B}SO_2R^{10A}$, $—NR^{10B}C(O)R^{10D}$, $—NR^{10B}C(O)OR^{10D}$, $—NR^{10B}OR^{10D}$, $—OCX^{10.1}_3$, $—OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $—CX^{11.1}_3$, $—CHX^{11.1}_2$, $—CH_2X^{11.1}$, $—CN$, $—SO_{n1}R^{11A}$, $—SO_{v1}NR^{11B}R^{11C}$, $—NHNR^{11B}R^{11C}$, $—ONR^{11B}R^{11C}$, $—NHC(O)NR^{11B}R^{11C}$, $—NHC(O)NR^{11B}R^{11C}$, $—N(O)_{m1}$, $—NR^{11B}R^{11C}$, $—C(O)R^{11D}$, $—C(O)OR^{11D}$, $—C(O)NR^{11B}R^{11C}$, $—OR^{11A}$, $—NR^{11B}SO_2R^{11A}$, $—NR^{11B}C(O)R^{11D}$, $—NR^{11B}C(O)OR^{11D}$, $—NR^{11B}OR^{11D}$, $—OCX^{11.1}_3$, $—OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $—CX^{12.1}_3$, $—CHX^{12.1}_2$, $—CH_2X^{12.1}$, $—CN$, $—SO_{n1}R^{12A}$, $—SO_{v1}NR^{12B}R^{12C}$, $—NHNR^{12B}R^{12C}$, $—ONR^{12B}R^{12C}$, $—NHC(O)NHNR^{12B}R^{12C}$, $—NHC(O)NR^{12B}R^{12C}$, $—N(O)_{m1}$, $—NR^{12B}R^{12C}$, $—C(O)R^{12D}$, $—C(O)OR^{12D}$, $—C(O)NR^{12B}R^{12C}$, $—OR^{12A}$, $—NR^{12B}SO_2R^{12A}$, $—NR^{12B}C(O)R^{12D}$, $—NR^{12B}C(O)OR^{12D}$, $—NR^{12B}OR^{12D}$, $—OCX^{12.1}_3$, $—OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $—CX^{13.1}_3$, $—CHX^{13.1}_2$, $—CH_2X^{13.1}$, $—CN$, $—SO_{n1}R^{13A}$, $—SO_{v1}NR^{13B}R^{13C}$, $—NHNR^{13B}R^{13C}$, $—ONR^{13B}R^{13C}$, $—NHC(O)NHNR^{13B}R^{13C}$, $—NHC(O)NR^{13B}R^{13C}$, $—N(O)_{m1}$, $—NR^{13B}R^{13C}$, $—C(O)R^{13D}$, $—C(O)OR^{13D}$, $—C(O)NR^{13B}R^{13C}$, $—OR^{13A}$, $—NR^{13B}SO_2R^{13A}$, $—NR^{13B}C(O)R^{13D}$, $—NR^{13B}C(O)OR^{13D}$, $—NR^{13B}OR^{13D}$, $—OCX^{13.1}_3$, $—OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $—CX^{14.1}_3$, $—CHX^{14.1}_2$, $—CH_2X^{14.1}$, $—CN$, $—SO_{n1}R^{14A}$, $—SO_{v1}NR^{14B}R^{14C}$, $—NHNR^{14B}R^{14C}$, $—ONR^{14B}R^{14C}$, $—NHC(O)NHNR^{14B}R^{14C}$, $—NHC(O)NR^{14B}R^{14C}$, $—N(O)_{m1}$, $—NR^{14B}R^{14C}$, $—C(O)R^{14D}$, $—C(O)OR^{14D}$, $—C(O)NR^{14B}R^{14C}$, $—OR^{14A}$, $—NR^{14B}SO_2R^{14A}$, $—NR^{14B}C(O)R^{14D}$, $—NR^{14B}C(O)OR^{14D}$, $—NR^{14B}OR^{14D}$, $—OCX^{14.1}_3$, $—OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $—CX^{15.1}_3$, $—CHX^{15.1}_2$, $—CH_2X^{15.1}$, $—CN$, $—SO_{n1}R^{15A}$, $—SO_{v1}NR^{15B}R^{15C}$, $—R^{15B}R^{15C}$, $—ONR^{15B}R^{15C}$, $—NHC(O)NHNR^{15B}R^{15C}$, $—NHC(O)NR^{15B}R^{15C}$, $—N(O)_{m1}$, $—NR^{15B}R^{15C}$, $—C(O)R^{15D}$, $—C(O)OR^{15D}$, $—C(O)$ $NR^{15B}R^{15C}$, —$OR^{15A}$, —$NR^{15B}SO_2R^{15A}$, —$NR^{15B}C(O)R^{15D}$, —$NR^{15B}C(O)OR^{15D}$, —$NR^{15B}OR^{15D}$, —$OCX^{15.1}{}_3$, —$OCHX^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, —$CX^{16.1}{}_3$, —$CHX^{16.1}{}_2$, —$CH_2X^{16.1}$, —$CN$, —$SO_{n1}R^{16A}$, —$SO_{v1}NR^{16B}R^{16C}$, —$R^{16B}R^{16C}$, —$ONR^{16B}R^{16C}$, —$NHC(O)NHNR^{16B}R^{16C}$, —$NHC(O)NR^{16B}R^{16C}$, —$N(O)_{m1}$, —$NR^{16B}R^{16C}$, —$C(O)R^{16D}$, —$C(O)OR^{16D}$, —$C(O)NR^{16B}R^{16C}$, —$OR^{16A}$, —$NR^{16B}SO_2R^{16A}$, —$NR^{16B}C(O)R^{16D}$, —$NR^{16B}C(O)OR^{16D}$, —$NR^{16B}OR^{16D}$, —$OCX^{16.1}{}_3$, —$OCHX^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, —$CX^{17.1}{}_3$, —$CHX^{17.1}{}_2$, —$CH_2X^{17.1}$, —$CN$, —$SO_{n1}R^{17A}$, —$SO_{v1}NR^{17B}R^{17C}$, —$NHNR^{17B}R^{17C}$, —$ONR^{17B}R^{17D}$, —$NHC(O)NHNR^{17B}R^{17C}$, —$NHC(O)NR^{17B}R^{17C}$, —$N(O)_{m1}$, —$NR^{17B}R^{17C}$, —$C(O)R^{17D}$, —$C(O)OR^{17D}$, —$C(O)NR^{17B}R^{17C}$, —$OR^{17A}$, —$NR^{17B}SO_2R^{17A}$, —$NR^{17B}C(O)R^{17D}$, —$NR^{17B}C(O)OR^{17D}$, —$NR^{17B}OR^{17D}$, —$OCX^{17.1}{}_3$, —$OCHX^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, —$CX^{18.1}{}_3$, —$CHX^{18.1}{}_2$, —$CH_2X^{18.1}$, —$CN$, —$SO_{n1}R^{18A}$, —$SO_{v1}NR^{18B}R^{18C}$, —$NHNR^{18B}R^{18C}$, —$ONR^{18B}R^{18C}$, —$NHC(O)NHNR^{18B}R^{18C}$, —$NHC(O)NR^{18B}R^{18C}$, —$N(O)_{m1}$, —$NR^{18B}R^{18C}$, —$C(O)R^{18D}$, —$C(O)OR^{18D}$, —$C(O)NR^{18B}R^{18C}$, —$OR^{18A}$, —$NR^{18B}SO_2R^{18A}$, —$NR^{18B}C(O)R^{18D}$, —$NR^{18B}C(O)OR^{18D}$, —$NR^{18B}OR^{18D}$, —$OCX^{18.1}{}_3$, —$OCHX^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, —$COR^{19D}$, —$C(O)NHNR^{19B}R^{19C}$, —$C(O)OR^{19D}$, —$SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, —$CF_3$, —$CCl_3$, —$CBr_3$, —$CI_3$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)$—$OH$, —$NHOH$, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$, and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently —Cl, —Br, —I or —F. In embodiments, the hair growth is an increase in hair growth relative to the absence of administration of the compound.

In another aspect, there is provided a method for inducing hair regeneration in a subject in need thereof, said method comprising administering to said subject an effective amount of a compound with structure of Formula (III):

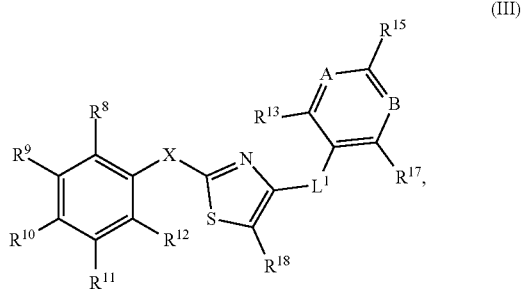

(III)

or a pharmaceutically acceptable salt thereof. For Formula (III), A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, —$CX^{8.1}{}_3$, —$CHX^{8.1}{}_2$, —$CH_2X^{8.1}$, —$CN$, —$SO_{n1}R^{8A}$, —$SO_{v1}NR^{8B}R^{8C}$, —$NHNR^{8B}R^{8C}$, —$ONR^{8B}R^{8C}$, —$NHC(O)NHNR^{8B}R^{8C}$, —$NHC(O)NR^{8B}R^{8C}$, —$N(O)_{m1}$, —$NR^{8B}R^{8C}$, —$C(O)R^{8D}$, —$C(O)OR^{8D}$, —$C(O)NR^{8B}R^{8C}$, —$OR^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}{}_3$, —$OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, —$CX^{9.1}{}_3$, —$CHX^{9.1}{}_2$, —$CH_2X^{9.1}$, —$CN$, —$SO_{n1}R^{9A}$, —$SO_{v1}NR^{9B}R^{9C}$, —$NHNR^{9B}R^{9C}$, —$ONR^{9B}R^{9C}$, —$NHC(O)NHNR^{9B}R^{9C}$, —$NHC(O)NR^{9B}R^{9C}$, —$N(O)_{m1}$, —$NR^{9B}R^{9C}$, —$C(O)R^{9D}$, —$C(O)OR^{9D}$, —$C(O)NR^{9B}R^{9C}$, —$OR^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}{}_3$, —$OCHX^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, —$CX^{10.1}{}_3$, —$CHX^{10.1}{}_2$, —$CH_2X^{10.1}$, —$CN$, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}{}_3$, —$OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, —$CX^{11.1}{}_3$, —CHX$^{11.1}_2$, —CH$_2$X$^{11.1}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —NR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{3B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{14}$ is hydrogen, halogen, —CX$^{14.1}_3$, —CHX$^{14.1}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}_3$, —OCHX$^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{16}$ is hydrogen, halogen, —CX$^{16.1}_3$, —CHX$^{16.1}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{7B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$, R$^{18D}$, R$^{19A}$, R$^{19B}$, R$^{19C}$ and R$^{19D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$, R$^{18C}$, R$^{19B}$ and R$^{19C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$, X$^{18.1}$, and X$^{19.1}$ are independently —Cl, —Br, —I or —F; and embodiments thereof. In embodiments, the hair regeneration is an increase in hair regeneration relative to the absence of administration of the compound.

In another aspect, there is provided a method for activating a quiescent hair follicle stem cell (HFSC) in a subject in need thereof. The method includes contacting a quiescent HFSC with an effective amount of a compound with structure of Formula (III):

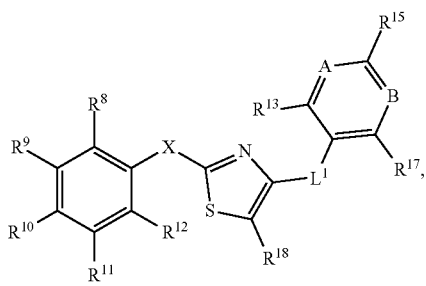

(III)

or a pharmaceutically acceptable salt thereof. For Formula (III), A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $-CX^{11.1}_3$, $-CHX^{11.1}_2$, $-CH_2X^{11.1}$, $-CN$, $-SO_{n1}R^{11A}$, $SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{15C}$, $-NHNR^{18B}R^{15C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)

—NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$, R$^{18D}$, R$^{19A}$, R$^{19B}$, R$^{19C}$ and R$^{19D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$, R$^{3C}$, R$^{4B}$, R$^{4C}$, R$^{5B}$, R$^{5C}$, R$^{6B}$, R$^{6C}$, R$^{7B}$, R$^{7C}$, R$^{8B}$, R$^{8C}$, R$^{9B}$, R$^{9C}$, R$^{10B}$, R$^{10C}$, R$^{11B}$, R$^{11C}$, R$^{12B}$, R$^{12C}$, R$^{13B}$, R$^{13C}$, R$^{14B}$, R$^{14C}$, R$^{15B}$, R$^{15C}$, R$^{16B}$, R$^{16C}$, R$^{17B}$, R$^{17C}$, R$^{18B}$, R$^{18C}$, R$^{19B}$ and R$^{19C}$ substituents bonded to the same nitrogen atom may optionally be joined to form a substituted or unsubstituted heterocycloalkyl or substituted or unsubstituted heteroaryl; and X$^{1.1}$, X$^{2.1}$, X$^{3.1}$, X$^{4.1}$, X$^{5.1}$, X$^{6.1}$, X$^{7.1}$, X$^{8.1}$, X$^{9.1}$, X$^{10.1}$, X$^{11.1}$, X$^{12.1}$, X$^{13.1}$, X$^{14.1}$, X$^{15.1}$, X$^{16.1}$, X$^{17.1}$, X$^{18.1}$, and X$^{19.1}$ are independently —Cl, —Br, —I or —F, and embodiments thereof, thereby activating said quiescent HFSC. In embodiments, the HFSC forms part of an organism (e.g. human) and the activating results in an increase in hair growth in the organism (e.g. relative to the absence of the compound).

In another aspect, there is provided a method for inducing glycolysis in a hair follicle stem cell (HFSC). The method includes contacting a HFSC with an effective amount of a compound with structure of Formula (III):

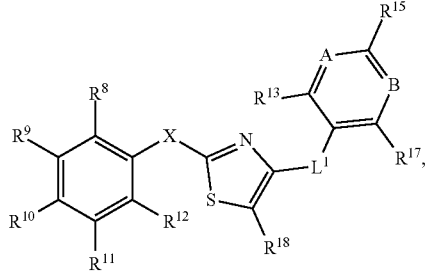

(III)

or a pharmaceutically acceptable salt thereof. For Formula (III), A is CR$^{14}$ or N; B is CR$^{16}$ or N; X is O, NR$^{19}$ or S; L$^1$ is a bond or substituted or unsubstituted C$_1$-C$_3$ alkylene; n1 is an integer from 0 to 4; m1 and v1 are independently 1 or 2; R$^8$ is hydrogen, halogen, —CX$^{8.1}_3$, —CHX$^{8.1}_2$, —CH$_2$X$^{8.1}$, —CN, —SO$_{n1}$R$^{8A}$, —SO$_{v1}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{18B}$R$^{8C}$, —N(O)$_{m1}$, —NR$^{18B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}_3$, —OCHX$^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^9$ is hydrogen, halogen, —CX$^{9.1}_3$, —CHX$^{9.1}_2$, —CH$_2$X$^{9.1}$, —CN, —SO$_{n1}$R$^{9A}$, —SO$_{v1}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is hydrogen, halogen, —CX$^{10.1}_3$, —CHX$^{10.1}_2$, —CH$_2$X$^{10.1}$, —CN, —SO$_{n1}$R$^{10A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m1}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ is hydrogen, halogen, —CX$^{11.1}_3$, —CHX$^{11.1}_2$, —CH$_2$X$^{11.1}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —R$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —R$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $-CX^{14.1}{}_3$, $-CHX^{14.1}{}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{4B}OR^{14D}$, $-OCX^{14.1}{}_3$, $-OCHX^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}{}_3$, $-CHX^{15.1}{}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}{}_3$, $-OCHX^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}{}_3$, $-CHX^{16.1}{}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}{}_3$, $-OCHX^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}{}_3$, $-CHX^{17.1}{}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{7B}R^{17C}$, $-NHC(O)NHNR^{7B}R^{7C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}{}_3$, $-OCHX^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}{}_3$, $-CHX^{18.1}{}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}{}_3$, $-OCHX^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{10B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$ and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{1.11}$, $X^{12.1}$, $X^{13.1}$, $X^{14.1}$, $X^{15.1}$, $X^{16.1}$, $X^{17.1}$, $X^{18.1}$ and $X^{19.1}$ are independently $-Cl$, $-Br$, $-I$ or $-F$, and embodiments thereof, thereby increasing glycolysis. In embodiments, the HFSC forms part of an organism (e.g. human) and the increase in glycolysis results in an increase in hair growth in the organism (e.g. relative to the absence of the compound). In embodiments, the inducing glycolysis is an increase in glycolytic activity (e.g. relative to the absence of the compound).

In another aspect, there is provided a method for activating lactate dehydrogenase in a hair follicle stem cell (HFSC), said method comprising contacting a HFSC with an effective amount of a compound with structure of Formula (III):

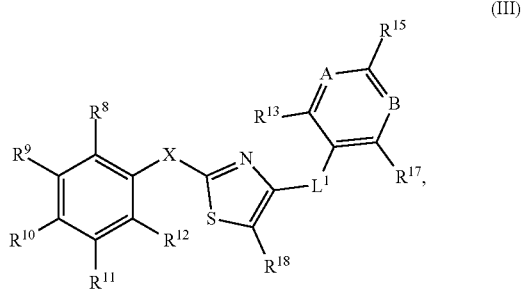

or a pharmaceutically acceptable salt thereof. For Formula (III), A is $CR^{14}$ or N; B is $CR^{16}$ or N; X is O, $NR^{19}$ or S; $L^1$ is a bond or substituted or unsubstituted $C_1$-$C_3$ alkylene; n1 is an integer from 0 to 4; m1 and v1 are independently 1 or 2; $R^8$ is hydrogen, halogen, $-CX^{8.1}{}_3$, $-CHX^{8.1}{}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^9$ is hydrogen, halogen, $-CX^{9.1}{}_3$, —CHX$^{9.1}{}_2$, —CH$_2$X$^{9.1}$, —CN, —SO$_{n1}$R$^{9A}$, —SO$_{v1}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}{}_3$, —OCHX$^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{10}$ is hydrogen, halogen, —CX$^{10.1}{}_3$, —CHX$^{10.1}{}_2$, —CH$_2$X$^{10.1}$, —CN, —SO$_{n1}$R$^{10A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m1}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$R$^{10D}$, —OCX$^{10.1}{}_3$, —OCHX$^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{11}$ is hydrogen, halogen, —CX$^{11.1}{}_3$, —CHX$^{11.1}{}_2$, —CH$_2$X$^{11.1}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}{}_3$, —OCHX$^{1.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{12}$ is hydrogen, halogen, —CX$^{12.1}{}_3$, —CHX$^{12.1}{}_2$, —CH$_2$X$^{12.1}$, —CN, —SO$_{n1}$R$^{12A}$, —SO$_{v1}$NR$^{12B}$R$^{12C}$, —NR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}{}_3$, —OCHX$^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{13}$ is hydrogen, halogen, —CX$^{13.1}{}_3$, —CHX$^{13.1}{}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{3B}$OR$^{13D}$, —OCX$^{13.1}{}_3$, —OCHX$^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{14}$ is hydrogen, halogen, —CX$^{14.1}{}_3$, —CHX$^{14.1}{}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}{}_3$, —OCHX$^{14.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ is hydrogen, halogen, —CX$^{15.1}{}_3$, —CHX$^{15.1}{}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}{}_3$, —OCHX$^{15.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{16}$ is hydrogen, halogen, —CX$^{16.1}{}_3$, —CHX$^{16.1}{}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}{}_3$, —OCHX$^{16.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{17}$ is hydrogen, halogen, —CX$^{17.1}{}_3$, —CHX$^{17.1}{}_2$, —CH$_2$X$^{17.1}$, —CN, —SO$_{n1}$R$^{17A}$, —SO$_{v1}$NR$^{7B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}{}_3$, —OCHX$^{17.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{18}$ is hydrogen, halogen, —CX$^{18.1}{}_3$, —CHX$^{18.1}{}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}{}_3$, —OCHX$^{18.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, R$^{17D}$, R$^{18A}$, R$^{18B}$, R$^{18C}$, R$^{18D}$, R$^{19A}$, R$^{19B}$, R$^{19C}$ and R$^{19D}$ are independently hydrogen, halogen, —CF$_3$, —CCl$_3$, —CBr$_3$, —Cl$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$ and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently —Cl, —Br, —I or —F, and embodiments thereof, thereby activating lactate dehydrogenase in a HFSC. In embodiments, the HFSC forms part of an organism (e.g. human) and the activating of the lactate dehydrogenase results in an increase in hair growth in the organism (e.g. relative to the absence of the compound). In embodiments, the activation of lactate dehydrogenase is an increase in lactate dehydrogenase enzymatic activity (e.g. relative to the absence of the compound).

BRIEF DESCRIPTION OF THE DRAWINGS

FIG. 1A: IHC staining for Ldha expression across the hair cycle shows Ldha protein confined to the HFSC niche, the bulge, indicated by the bracket. IHC staining for Sox9 on serial sections demarcates the HFSC population. Scale bar indicates 20 micrometers. FIG. 1B: Immunoblotting on FACS-isolated HFSC populations (α6low/Cd34+ and α6hiCd34+) versus total epidermis (Epi) shows differential expression of Ldha in the stem cell niche. Sox9 is a marker of HFSCs, and β-actin is a loading control. FIG. 1C: Colorimetric assay for Ldh enzyme activity in the epidermis shows highest activity in the bulge (brackets) and subcuticular muscle layer (bracket). This activity is enriched in the bulge across different stages of the hair cycle. Activity is indicated in the figure. Note also that developing hair shafts in pigmented mice show strong deposits of melanin as observed here; hair shafts never displayed any stain indicative of Ldh activity. Scale bars indicate 50 micrometers. FIG. 1D: Ldh activity in sorted cell populations, measured using a plate reader-based assay, also shows the highest Ldh activity in two separate HFSC populations (α6hi/Cd34 and α6low/Cd34) compared to epidermal cells (Epi) and fibroblasts (FBs). Each bar represents the average signal for each cell type where n=9 mice pooled from 3 independent experiments. Shown as mean±SEM. Paired t-test was performed, p<0.05 shown for each cell type versus epidermal cells FIG. 1E: HFSCs and epidermal cells were isolated during telogen (day 50) by FACS, and metabolites were extracted and analyzed by LC-MS. Heatmaps show relative levels of glycolytic and TCA cycle metabolites from cells isolated from different mice in independent experiments with cells from three animals in each. Asterisks indicate significant difference in metabolite levels between epidermal cells and HFSCs. For FIG. 1E, paired t-test was performed; * denotes p<0.05,  denotes p<0.01, * denotes p<0.001, ns denotes p>0.05, and n=9 mice pooled from 3 independent experiments.

FIG. 2A: GSEA on RNA-seq transcriptome data from HFSCs versus total epidermis shows enrichment for Glycolysis related genes in HFSCs (NES=1.72). FIG. 2B: GSEA on microarray transcriptome data from HFSCs versus total epidermis shows enrichment for Glycolysis related genes in HFSCs (NES=1.45). Results were generated from three mice of each condition. FIG. 2C: RNA-seq data from HFSCs sorted during telogen or telogen-anagen transition show induction of Ldha[21]. Data represent the average of three separate animals at each timepoint. FIG. 2D: Ldh activity in sorted stem cell populations, measured using a plate reader-based assay, shows elevated Ldh activity as stem cells become activated in telogen to anagen transition (Tel-Ana). Each bar represents the average signal for each condition where n=9 mice pooled from 3 independent experiments. Shown as mean±SEM. Paired t-test was performed, p<0.05. FIG. 2E: Heatmap showing relative levels of glycolytic and TCA cycle metabolites extracted from quiescent (Telogen, day 50), activated (Telogen-Anagen, day 70) and HFSCs that have returned to the quiescent state (Anagen, day 90). Data shown were generated from n=3 animals per timepoint in 3 independent experiments.

FIG. 3A: Ldha$^{+/+}$ animals enter the hair cycle (anagen) synchronously around day 70 as measured by shaving and observation beginning at day 50. K15CrePR;Ldha$^{fl/fl}$ animals treated with Mifepristone show defects in anagen entry. Results shown are representative of at least 33 animals of each genotype. FIG. 3B: Skin pathology showing that K15CrePR;Ldha$^{fl/fl}$ animals showed neither and remained in telogen. Scale bars indicate 50 micrometers. FIG. 3C: Ldh enzyme activity assay showed that K15CrePR;Ldha fl/fl animals lacked this activity in the HFSCs (indicated by bracket). Scale bars indicate 20 micrometers. FIG. 3D: Graph showing percentage of follicles in telogen, telogen to anagen transition and anagen in K15CrePR;Ldha$^{+/+}$ mice versus K15CrePR;Ldha$^{fl/fl}$ mice (n=225 follicles from 3 mice per genotype). Shown as mean±SEM. Paired t-test was performed, p<0.05. FIG. 3E: Heatmap showing relative levels of glycolytic and TCA cycle metabolites extracted from Ldha$^{++}$ HFSCs and Ldha$^{fl/fl}$ HFSCs and measured by LC-MS. Asterisks indicate significant difference in metabolite levels between genotypes. For FIG. 3E, paired t-test was performed,* denotes p<0.05,  denotes p<0.01, * denotes p<0.001, ns denotes p>0.05, and n=9 mice pooled from 3 independent experiments. FIG. 3F. Immunohistochemistry staining for Ki-67, a marker of proliferation is absent in Ldha$^{fl/fl}$ HFSCs. Phospo-S6, a marker in HFSCs at the beginning of a new hair cycle, is absent in Ldha$^{fl/fl}$ HFSCs. Staining for Ldha protein shows specific deletion in HFSCs. Brackets indicate bulge. Staining for Sox9 shows that HFSCs are still present in Ldha deleted niche. Scale bars indicate 20 micrometers. FIG. 3G: Animals which have Ldha deleted specifically in their HFSCs as controlled by Lgr5CreER, show profound defects in the entry into anagen. Right, skin pathology showing that Lgr5CreER;Ldha$^{fl/fl}$ animals mostly remained in telogen. Scale bars indicate 100 micrometers. Results shown are representative of at least 12 animals of each genotype. FIG. 3H: Ldh enzyme activity assay in the epidermis shows that Lgr5CreER;Ldha$^{fl/fl}$ animals lacked this activity in the HFSCs. Scale bars indicate 20 micrometers. FIG. 3I: LC-MS analysis of metabolites from the indicated mice. Data shown were generated from n=3 animals per condition pooled from 3 independent experiments.

FIG. 4A: Mpc1fl/fl animals show pigmentation and hair growth, consistent with entry into the anagen cycle at 8.5 weeks, whereas Mpc1+/+ animals do not show dorsal pigmentation and hair growth this early. Animals shown are representative of at least 12 animals of each genotype. FIG. 4B: FACS isolation of HFSC bulge populations in Mpc1+/+ versus Mpc1fl/fl mice followed by western blotting shows successful deletion of Mpc1 protein in the stem cell niche. β-actin is a loading control. FIG. 4C: Plate reader assay for Ldh activity on sorted HFSC populations shows elevated activity in Mpc1fl/fl HFSCs compared to Mpc1+/+ HFSCs. Each bar represents the average signal for each genotype where n=9 mice pooled from 3 independent experiments. Shown as mean±SEM. Paired t-test was performed, p<0.05. FIG. 4D: Histology on WT versus Mpc1 deletion skin shows induction of anagen in absence of Mpc1. Scale bars indicate 100 micrometers. Quantification of phenotype at right shows percentage of dorsal follicles in telogen, telogen to anagen transition and anagen in Mpc1+/+ mice versus Mpc1fl/fl mice (n=250 follicles from 3 mice per genotype). Shown as mean±SEM. Paired t-test was performed, p<0.05. FIG. 4E: Immunohistochemistry staining for Ki-67, a marker of proliferation that is only active in HFSCs at the beginning of a new hair cycle, is only present in Mpc1fl/fl HFSCs at 8.5 weeks, consistent with their accelerated entry into a new hair cycle. Phospo-S6, another marker that is only active in HFSCs at the beginning of a new hair cycle, is only present in Mpc1fl/fl HFSCs. Staining for Sox9 shows that HFSCs are present in Mpc1 deleted niche. Images taken at 60× magnification. FIG. 4F: Deletion of Mpc1 in mice bearing the Lgr5CreER allele shows strong induction of the hair cycle. Results are representative of at least 9 animals per genotype. FIG. 4G: Quantification of pigmentation in the indicated genotypes across three independent litters (n=5 mice per genotype).

FIG. 6A: RNA-seq data from sorted HFSCs in telogen and telogen-anagen transition[21]. n=3 mice per timepoint. Shown as mean±SEM. Paired t-test was performed, p<0.05. FIG. 6B: Nuclear protein fractions show expression of n-Myc and c-Myc in HFSCs compared to epidermal cells. H3k27ac is a loading control for nuclear proteins. FIG. 6C: Total protein preps from skin treated with 2 topical doses of RCGD423 (50 uM) show increased c-Myc, n-Myc and Ldha protein levels compared to animals that received 2 topical doses of vehicle control. β-actin is a loading control. FIG. 6D: Plate reader assay for Ldh enzyme activity in the epidermis. Each bar represents the average signal for each condition where n=9 mice pooled from 3 independent experiments. Shown as mean±SEM. Paired t-test was performed, p<0.05. FIG. 6E: Ldh enzyme activity assay in the epidermis in vehicle control and RCGD423 treated animals. Scale bar indicates 50 micrometers. FIG. 6F: Metabolomic analysis of Lactate on HFSCs isolated from RCGD423 treated skin for 48 hours. Each bar represents the average signal for each condition where n=9 mice pooled from 3 independent experiments. Shown as mean±SEM. Paired t-test was performed, p<0.05. FIG. 6G: Immunohistochemistry staining for Ki-67 and phospo-Stat3, a downstream marker of RCGD423 activity. Scale bar indicates 20 micrometers. FIG. 6H: Animals treated with RCGD423 (50 uM) show pigmentation and hair growth, indicative of entry into anagen, after 5 doses. Images shown are representative of at least 14 mice from 7 independent experiments. Scale bar indicates 100 micrometers. Quantification of phenotype showing time to observed phenotype in vehicle versus RCGD423 treated mice. n=6 mice per condition. Shown as mean±SEM.

FIG. 7A: Top, IHC with antibody recognizing specifically Ldha (same as used in FIG. 1A); bottom, IHC with antibody recognizing multiple isoforms of Ldh protein. Scale bars indicate 20 micrometers. FIG. 7B: the sorting strategy employed to isolate two populations of cells from the bulge. This particular sort was used to isolate the protein samples shown by western blot in FIG. 1B. FIG. 7C: Validation of colorimetric Ldh enzyme activity assay. The highest Ldh enzyme activity was observed in HFSC bulge and in the muscle. Activity indicated in the figure. In absence of substrate lactate there was no detectable activity; right, additional validation of colorimetric Ldh enzyme activity assay. Enzyme activity inhibited by treating skin with HCl before addition of staining solution with substrate lactate. No Ldh activity detected. Skin in which enzyme activity is not inhibited by Hydrochloric Acid (HCl) shows highest Ldh enzyme activity in HFSC bulge and in the muscle. Scale bars indicate 50 micrometers.

FIG. 8A. Analysis of RNA-seq data to validate that HFSCs in telogen-anagen transition were in fact in such a transition. The telogen-anagen transition is known to be driven by Shh (Gli factors are targets) and Wnt (Lef1, Axin, Ccnd1 are targets) signaling, and correlate with increased proliferation (Ki67 and Pcna). In addition, Sox4 was previously identified as a regulator of the telogen-anagen transition. n=3 mice per timepoint. Shown as mean±SEM. Paired t-test was performed, p<0.05. FIG. 8B: staining for Ki-67 marks dividing cells during various stages of the hair cycle. Brackets indicate the HFSC niche. Scale bars indicate 100 micrometers.

FIG. 9A: K15CrePR;Ldha$^{fl/fl}$ animals treated with Mifepristone during telogen (day 50) were allowed to develop for 6 months. None of the K15CrePR;Ldha$^{fl/fl}$ mice showed complete hair regrowth, compared to control animals that all grew their hair coats back completely. Images are representative of at least 12 animals per genotype. FIG. 9B: Histological examination of the long term K15CrePR;Ldha$^{fl/fl}$ mice showed that Ldha-null HFSCs remained in telogen while WT HFSCs went through anagen and then returned to telogen. This is apparent from thick sections (50 micron, right) that show an increased number of club hairs in the WT relative to Ldha-null follicles. Scale bars indicate 100 micrometers (left), and 20 micrometers (middle and right). FIG. 9C: IHC for HFSC marker Sox9 showed that deletion of Ldha from HFSCs does not affect their presence in the bulge even after 6 months. In addition, IHC and Ldh activity assay demonstrate that the deletion of Ldha was sustained. Because of the mosaicism of the deletion, in some portions of K15CrePR;Ldha$^{fl/fl}$ skin Ldha was not deleted. Shown on the bottom row is tissue from hair bearing skin in the K15CrePR;Ldha$^{+/+}$ mice where Ldha was still expressed, showing that new hair growth in K15CrePR;Ldha$^{fl/fl}$ mice was due to lack of deletion of Ldha caused by the mosaic approach used to mediate Cre recombination. Scale bars indicate 20 micrometers. FIG. 9D: To determine how various signaling pathways previously linked to the hair cycle are affected by loss of Ldha in HFSCs, we performed IHC for markers that indicate activity of these pathways in telogen and telogen-anagen transition. Note that pStat5 appears to be suppressed in normal telogen-anagen transition, and this does not seem to occur in Ldha-null HFSCs. pStat1 and pStat3 did not seem to be affected by loss of Ldha. Expression of Gli3, a target of Shh signaling, is typically induced in an activated hair germ derived from HFSCs, but Ldha-null HFSCs do not make an active hair germ. Activation of the Wnt pathway is indicated by nuclear localization of β-catenin, and very little nuclear β-catenin was detected in Ldha-null HFSCs. Scale bars indicate 6 micrometers.

FIG. 10A: Six months after initiation of deletion of Mpc1 in HFSCs (K15CrePR;Mpc1fl/fl), mice lacking Mpc1 show no deleterious effects as measured by the hair cycle (left), pathology (middle, Hematoxylin and Eosin staining), or staining for HFSCs (right, Sox9). Scale bars indicate 100 micrometers in middle panel, and 50 micrometers in right panel. Images are representative of at least 12 animals per genotype. FIG. 10B: To demonstrate that the deletion of Mpc1 promotes proliferation specifically in HFSCs, we used K15CrePR;Ldha$^{fl/fl}$ mice bearing a lox-stop-lox-Tomato allele to look at K15+ HFSCs and proliferation with and without Mpc1 deletion (left). In addition, we took advantage of the ires-GFP within the Lgr5CreER allele to stain for Ki-67 and GFP and look for co-localization with and without Mpc1 deletion (right). White brackets denote bulge area. Scale bars represent 20 micrometers. FIG. 10C: Deletion of Mpc1 in mice bearing the Lgr6CreER allele shows no premature induction of the hair cycle. FIG. 10D: Ldh activity assay on sorted HFSCs from either control or Lgr6CreER mediated Mpc1 deletion mice showed increased activity in cells lacking Mpc1. n=6 mice per genotype pooled from 2 independent experiments. Shown as mean±SEM. Paired t-test was performed, p<0.05.

DETAILED DESCRIPTION OF THE INVENTION

I. Definitions

Figure 1A:
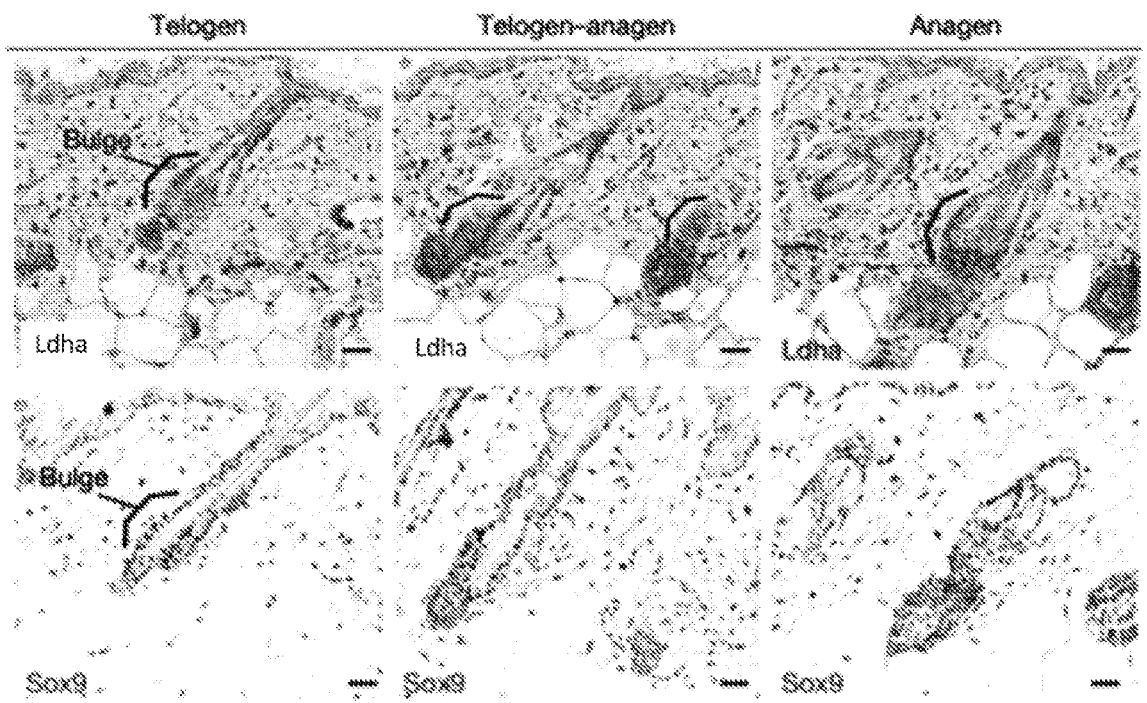
FIGS. 1A-1E. Lactate dehydrogenase activity is enriched in HFSCs.
Figure 1B:
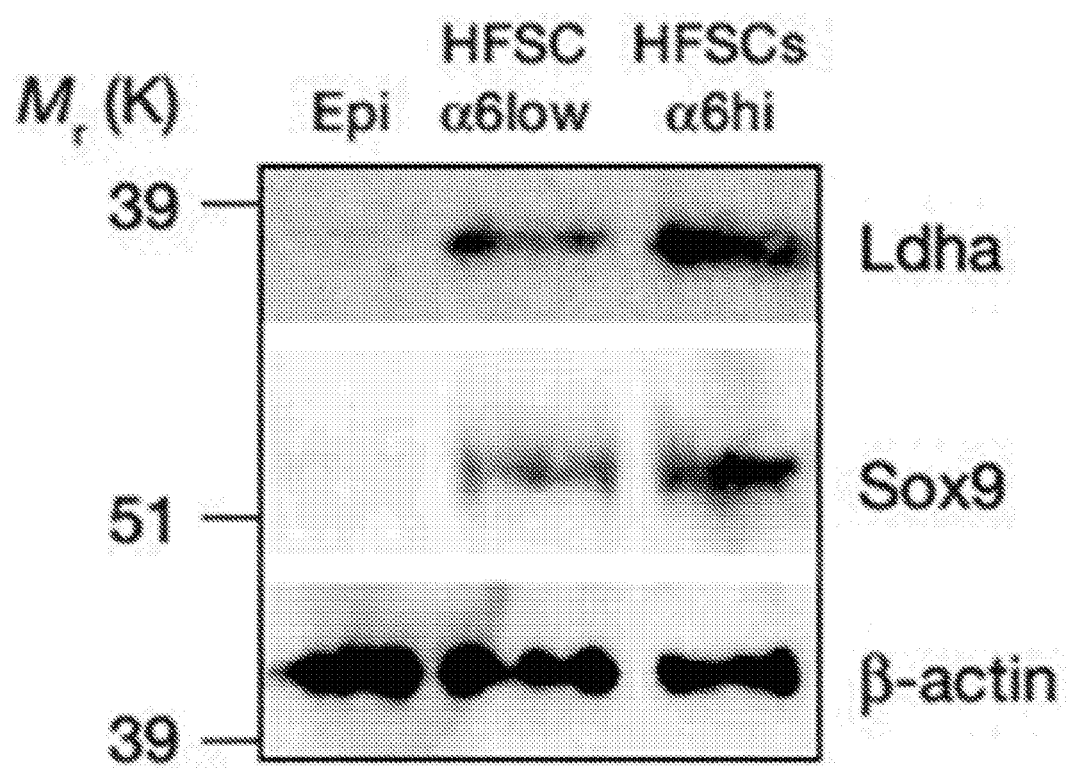

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. Heteroalkyl is not cyclized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

The term "oxy" as used herein, alone or in combination, refers to —O—.

The term "aryloxy" as used herein, alone or in combination, refers to a substituted or unsubstituted aryl group attached to the parent molecular moiety through an oxy i.e. an ether group. An example of an unsubstituted aryl ether group is phenoxy (i.e. $C_6H_5O$—).

The term "heteroaryloxy" as used herein, alone or in combination, refers to a substituted or unsubstituted heteroaryl group attached to the parent molecular moiety through an oxy i.e. a heteroaryl ether group. An example of an unsubstituted heteroaryl ether group is thiophenyl (i.e. $C_4H_3SO$—).

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR',
=N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRS$O_2$R', —CN and —$NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —N$RSO_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, Oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

The term "about" in the context of a numerical value means, unless indicated otherwise, the nominal numerical value±10% thereof.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " ⌇ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished for example as $R^{13A}$, $R^{13B}$, $R^{13C}$, $R^{13D}$, etc., wherein each of $R^{13A}$, $R^{3B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

A "nitrile" refers to a organic compound having a —CN group.

A "protected secondary amine" refers to the covalent attachment of a monovalent chemical moiety to an amine nitrogen atom that functions to prevent the amine moiety from reacting with reagents used in the chemical synthetic methods described herein (commonly referred to as "protecting" the amine group) and may be removed under conditions that do not substantially degrade the molecule of which the amine moiety forms a part (commonly referred to as "deprotecting" the amine group) thereby yielding a free amine. An amine protecting group can be acid labile, base labile, or labile in the presence of other reagents. Amine protecting groups include but are not limited to: -carbamates (such as -carbobenzyloxy (Cbz), -t-butoxycarbonyl (t-Boc), -fluorenylmethyloxycarbonyl (Fmoc), and -allyl carbamates), -benzyl, -4-methoxyphenyl, or -2,4-dimethoxyphenyl.

In some embodiments, the compound is a chemical species set forth in the Examples section or figures.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The terms "contacting" and "reacting" are used synonymously and may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, "biomolecule" is used in its customary sense and refers to a molecule that is present in living organisms and synthetic derivatives thereof, including macromolecules such as proteins, carbohydrates, lipids, and nucleic acids, as well as small molecules such as primary metabolites, secondary metabolites, and natural products. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

The terms "gp130 receptor," "gp130," gp130 protein," "IL6ST receptor," "IL6ST" or "IL6ST protein" are here used interchangeably and according to their common, ordinary meaning (e.g., transmembrane protein "glycoprotein 130") and refer to proteins of the same or similar names and functional fragments and homologs thereof. The term includes any recombinant or naturally occurring form of, or variants thereof that maintain gp130 activity (e.g. within at least 30%, 40%, 50%, 60%, 70%, 80%, 90%, 95%, or 100% activity compared to gp130).

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein include those compounds that readily undergo chemical or enzymatic changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be gp130. Thus, activation includes, at least in part, partially or totally increasing stimulation, increasing, promoting, or expediting activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. joint surface injury, arthritis or cartilage degenerative disease) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anti-cartilage degenerative agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anti-cartilage degenerative or anti-arthritic agents).

Co-administration includes administering one active agent (e.g. a complex described herein) within 0.5, 1, 2, 4, 6, 8, 10, 12, 16, 20, or 24 hours of a second active agent (e.g. anti-cartilage degenerative agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cartilage degenerative disorders.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. In embodiments, the patient is middle-aged (e.g., 45-65). In embodiments, the patient is greater than 30 years old. In embodiments, the patient is greater than 40 years old. In embodiments, the patient is greater than 50 years old. In embodiments, the patient is greater than 60 years old. In embodiments, the patient is greater than 70 years old. In embodiments, the patient is greater than 80 years old. In embodiments, the patient is 40 to 90 years old. In embodiments, the patient is 50 to 90 years old. In embodiments, the patient is 60 to 90 years old. In embodiments, the patient is 40 to 60 years old. In embodiments, the patient is 50, 60, 70, 80, or 90 years old. In embodiments, the patient is 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 years old.

"Disease" or "condition" refer to a state of being or health status of a patient or subject capable of being treated with the compounds or methods provided herein. Disease as used herein may refer to cartilage degenerative disease, joint surface injury or arthritis.

The term "linker" as described herein is a divalent chemical group that covalently joins one chemical moiety to another. Specific examples of linkers are described herein. Linkers may be polyethylene (PEG) linkers or bioconjugate linkers.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

As used herein, the term "proliferative program" and the like refer to the ability of a cell to proliferate. In embodiments, cell proliferation requires production of collagen. The term "activating compound" and the like refer to compounds disclosed herein having the ability to increase expression of p-STAT3 and c-Myc in a competent adult chondrocyte.

The term "hair growth" or the like refer, in the usual and customary sense, to expression of the hair shaft. The term "hair shaft" or the like refers, in the usual and customary sense, to the hard filamentous part of the hair follicle which extends above the dermis. The term "hair regeneration," "hair rejuvenation" or the like refers, in the usual and customary sense, to the appearance of a hair shaft in a region of dermis which had previously demonstrated hair shafts, but which hair shafts had subsequently become reduced in number or even eliminated. The terms "hair follicle stem cell," "HFSC" or the like refer, in the usual and customary sense, to a cell within the hair follicle which produces hair, as well known in the art. The term "quiescent hair follicle stem cell" or the like refers, in the usual and customary sense, to a hair follicle stem cell in the telogen phase, as well known in the art. The term "activating a quiescent hair follicle stem cell" or the like refers, in the usual and customary sense, to transition from the resting (telogen) or involuting (catagen) phases to growth phase (anagen), as well known in the art.

I. Methods

In an aspect is provided a method for inducing hair growth in a subject in need thereof, the method including administering to the subject an effective amount of a compound having the formula:

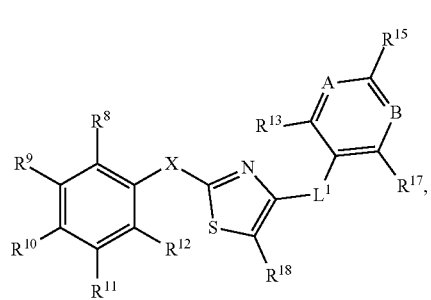

or a pharmaceutically acceptable salt thereof. For Formula (III), A is $CR^{14}$ or N; B is $CR^{16}$ or N; X is O, $NR^{19}$ or S; $L^1$ is a bond, O, $N(R^{20})$, S or substituted or unsubstituted $C_1$-$C_3$ alkylene; n1 is an integer from 0 to 4; m1 and v1 are independently 1 or 2; $R^8$ is hydrogen, halogen, $—CX^{8.1}_3$, $—CHX^{8.1}_2$, $—CH_2X^{8.1}$, $—CN$, $—SO_{n1}R^{8A}$, $—SO_{v1}NR^{8B}R^{8C}$, $—NHNR^{8B}R^{8C}$, $—ONR^{8B}R^{8C}$, $—NHC(O)NHNR^{8B}R^{8C}$, $—NHC(O)NR^{8B}R^{8C}$, $—N(O)_{m1}$, $—NR^{8B}R^{8C}$, $—C(O)R^{8D}$, $—C(O)OR^{8D}$, $—C(O)NR^{8B}R^{8C}$, $—OR^{8A}$, $—NR^{8B}SO_2R^{8A}$, $—NR^{8B}C(O)R^{8D}$, $—NR^{8B}C(O)OR^{8D}$, $—NR^{8B}OR^{8D}$, $—OCX^{8.1}_3$, $—OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or unsubstituted heteroaryl; $R^9$ is hydrogen, halogen, $—CX^{9.1}_3$, $—CHX^{9.1}_2$, $—CH_2X^{9.1}$, $—CN$, $—SO_{n1}R^{9A}$, $—SO_{v1}NR^{9B}R^{9C}$, $—NHNR^{9B}R^{9C}$, $—ONR^{9B}R^{9C}$, $—NHC(O)NHNR^{9B}R^{9C}$, $—NHC(O)NR^{9B}R^{9C}$, $—N(O)_{m1}$, $—NR^{9B}R^{9C}$, $—C(O)R^{9D}$, $—C(O)OR^{9D}$, $—C(O)NR^{9B}R^{9C}$, $—OR^{9A}$, $—NR^{9B}SO_2R^{9A}$, $—NR^{9B}C(O)R^{9D}$, $—NR^{9B}C(O)OR^{9D}$, $—NR^{9B}OR^{9D}$, $—OCX^{9.1}_3$, $—OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10}$ is hydrogen, halogen, $—CX^{10.1}_3$, $—CHX^{10.1}_2$, $—CH_2X^{10.1}$, $—CN$, $—SO_{n1}R^{10A}$, $—SO_{v1}NR^{10B}R^{10C}$, $—NHNR^{10B}R^{10C}$, $—ONR^{10B}R^{10C}$, $—NHC(O)NHNR^{10B}R^{10C}$, $—NHC(O)NR^{10B}R^{10C}$, $—N(O)_{m1}$, $—NR^{10B}R^{10C}$, $—C(O)R^{10D}$, $—C(O)OR^{10D}$, $—C(O)NR^{10B}R^{10C}$, $—OR^{10A}$, $—NR^{10B}SO_2R^{10A}$, $—NR^{10B}C(O)R^{10D}$, $—NR^{10B}C(O)OR^{10D}$, $—NR^{10B}OR^{10D}$, $—OCX^{10.1}_3$, $—OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{11}$ is hydrogen, halogen, $—CX^{11.1}_3$, $—CHX^{11.1}_2$, $—CH_2X^{11.1}$, $—CN$, $—SO_{n1}R^{11A}$, $—SO_{v1}NR^{11B}R^{11C}$, $—NHNR^{11B}R^{11C}$, $—ONR^{11B}R^{11C}$, $—NHC(O)NHNR^{11B}R^{11C}$, $—NHC(O)NR^{11B}R^{11C}$, $—N(O)_{m1}$, $—NR^{11B}R^{11C}$, $—C(O)R^{11D}$, $—C(O)OR^{11D}$, $—C(O)NR^{11B}R^{11C}$, $—OR^{11A}$, $—NR^{11B}SO_2R^{11A}$, $—NR^{11B}C(O)R^{11D}$, $—NR^{11B}C(O)OR^{11D}$, $—NR^{11B}OR^{11D}$, $—OCX^{11.1}_3$, $—OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{12}$ is hydrogen, halogen, $—CX^{12.1}_3$, $—CHX^{12.1}_2$, $—CH_2X^{12.1}$, $—CN$, $—SO_{n1}R^{12A}$, $—SO_{v1}NR^{12B}R^{12C}$, $—NHNR^{12B}R^{12C}$, $—ONR^{12B}R^{12C}$, $—NHC(O)NHNR^{12B}R^{12C}$, $—NHC(O)NR^{12B}R^{12C}$, $—N(O)_{m1}$, $—NR^{12B}R^{12C}$, $—C(O)R^{12D}$, $—C(O)OR^{12D}$, $—C(O)NR^{12B}R^{12C}$, $—OR^{12A}$, $—NR^{12B}SO_2R^{12A}$, $—NR^{12B}C(O)R^{12D}$, $—NR^{12B}C(O)OR^{12D}$, $—NR^{2B}OR^{12D}$, $—OCX^{12.1}_3$, $—OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ is hydrogen, halogen, $—CX^{13.1}_3$, $—CHX^{13.1}_2$, $—CH_2X^{13.1}$, $—CN$, $—SO_{n1}R^{13A}$, $—SO_{v1}NR^{13B}R^{13C}$, $—NHNR^{13B}R^{13C}$, $—ONR^{13B}R^{13C}$, $—NHC(O)NHNR^{13B}R^{13C}$, $—NHC(O)NR^{13B}R^{13C}$, $—N(O)_{m1}$, $—NR^{13B}R^{13C}$, $—C(O)R^{13D}$, $—C(O)OR^{13D}$, $—C(O)NR^{13B}R^{13C}$, $—OR^{13A}$, $—NR^{13B}SO_2R^{13A}$, $—NR^{13B}C(O)R^{13D}$, $—NR^{13B}C(O)OR^{13D}$, $—NR^{3B}OR^{13D}$, $—OCX^{13.1}_3$, $—OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{14}$ is hydrogen, halogen, $—CX^{14.1}_3$, $—CHX^{14.1}_2$, $—CH_2X^{14.1}$, $—CN$, $—SO_{n1}R^{14A}$, $—SO_{v1}NR^{14B}R^{14C}$, $—NHNR^{14B}R^{14C}$, $—ONR^{14B}R^{14C}$, $—NHC(O)NHNR^{14B}R^{14C}$, $—NHC(O)NR^{14B}R^{14C}$, $—N(O)_{m1}$, $—NR^{14B}R^{14C}$, $—C(O)R^{14D}$, $—C(O)OR^{14D}$, $—C(O)NR^{14B}R^{14C}$, $—OR^{14A}$, $—NR^{14B}SO_2R^{14A}$, $—NR^{14B}C(O)R^{14D}$, $—NR^{14B}C(O)OR^{14D}$, $—R^{14B}OR^{14D}$, $—OCX^{14.1}_3$, $—OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{8B}SO_2R^{18A}$, $-NR^{18C}(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$, and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently $-Cl$, $-Br$, $-I$ or $-F$.

In embodiments, L is a bond and X is NH. In further embodiments, wherein $R^{13}$, $R^{15}$, $R^{17}$ and $R^{18}$ are independently hydrogen. In further embodiments, $R^8$, $R^9$, $R^{11}$ and $R^{12}$ are independently hydrogen. In further embodiments, A is $CR^{14}$; and B is $CR^{16}$. In embodiments, $R^8$, $R^9$, $R^{11}$, $R^{12}$, $R^{13}$, $R^{15}$, $R^{17}$ and $R^{18}$ are independently hydrogen. In embodiments, A is N, B is $CR^{16}$, and $R^{16}$ is hydrogen. In embodiments, $R^{10}$ is fluorine, chlorine, bromine or iodine. In embodiments, A and B are independently N, and $R^{10}$ is fluorine, chlorine, bromine or iodine.

In embodiments, $R^{10}$ is hydrogen, fluorine, chlorine, iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{14}$ and $R^{16}$ are independently hydrogen. In embodiments, $R^{10}$ is fluorine, chlorine or iodine. In embodiments, $R^{10}$ is fluorine. In embodiments, $R^{10}$ is chlorine. In embodiments, $R^{10}$ is iodine. In embodiments, $R^{10}$ is bromine. In embodiments, $R^{10}$ is $-CX^{10.1}_3$, $-CHX^{10.1}_2$, or $-CH_2X^{10.1}$. In embodiments, $R^{10}$ is $-CF_3$, $-CHF_2$, or $-CH_2F$. In embodiments, $R^{10}$ is $-CBr_3$, $-CHBr_2$, or $-CH_2Br$. In embodiments, $R^{10}$ is $-CCl_3$, $-CHCl_2$, or $-CH_2Cl$. In embodiments, $R^{10}$ is $-CI_3$, $-CHI_2$, or $-CH_2I$.

In embodiments of the method, the compound with structure of Formula (III) has the structure of Formula (IIIa):

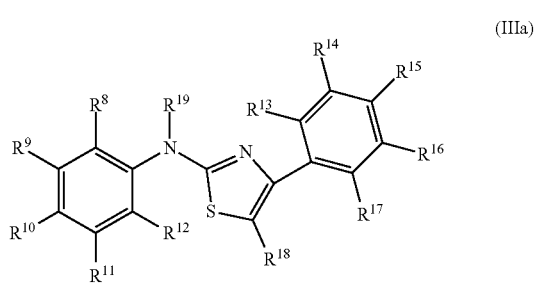

(IIIa)

or a pharmaceutically acceptable salt thereof, wherein: $R^{10}$ is hydrogen, fluorine, chlorine or iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{14}$ is hydrogen. In embodiments, $R^{16}$ is hydrogen.

In embodiments of the method, the compound with structure of Formula (III) has the structure of Formula (IIIb):

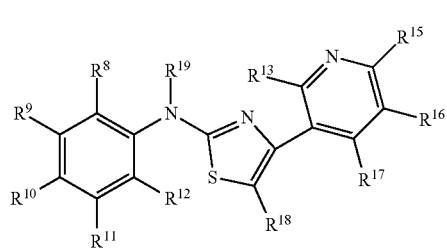

(IIIb)

or a pharmaceutically acceptable salt thereof.

In embodiments of the method, the compound with structure of Formula (III) has the structure of Formula (IIIc):

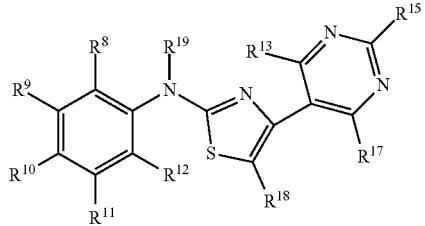

(IIIc)

or a pharmaceutically acceptable salt thereof.

In embodiments of the method, the compound has the formula:

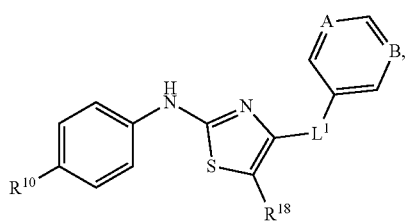

wherein A, B, $L^1$, $R^{18}$, and $R^{10}$ are as described herein.

In embodiments of the method, the compound has the formula:

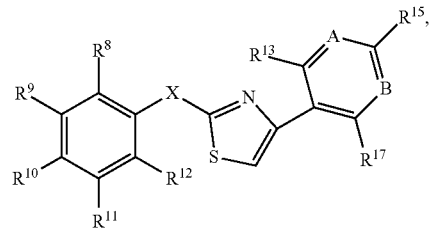

wherein A, B, $R^{13}$, $R^{15}$, $R^{17}$, X, $R^8$, $R^9$, $R^{10}$, $R^{11}$, and $R^{12}$ are as described herein.

In embodiments of the method, the compound has the formula:

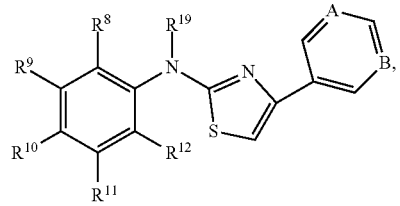

wherein A, B, $R^{19}$, $R^8$, $R^9$, $R^{10}$, $R^{11}$, and $R^{12}$ are as described herein.

In embodiments of the method, the compound has the formula:

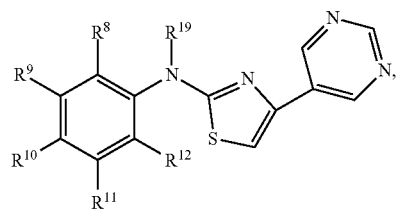

wherein $R^{19}$, $R^8$, $R^9$, $R^{10}$, $R^{11}$, and $R^{12}$ are as described herein.

In embodiments of the method, the compound has the formula:

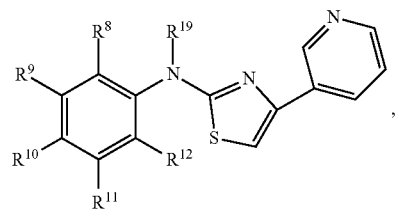

wherein $R^{19}$, $R^8$, $R^9$, $R^{10}$, $R^{11}$, and $R^{12}$ are as described herein.

In embodiments of the method, the compound has the formula:

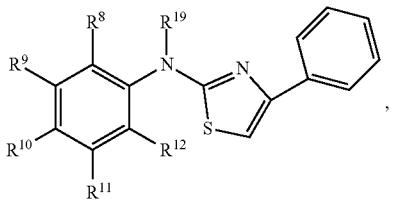

wherein $R^{19}$, $R^8$, $R^9$, $R^{10}$, $R^{11}$, and $R^{12}$ are as described herein.

In embodiments of the method, the compound has the formula:

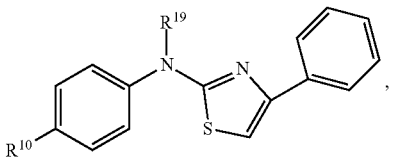

wherein $R^{19}$ and $R^{10}$ are as described herein.

In embodiments of the method, the compound has the formula:

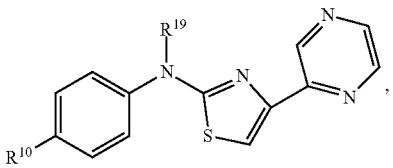

wherein $R^{10}$ and $R^{19}$ are as described herein.

In embodiments of the method, the compound has the formula:

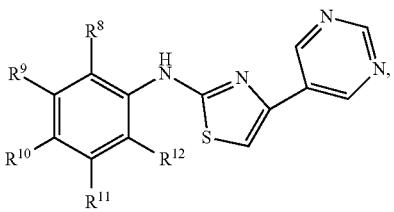

wherein $R^8$, $R^9$, $R^{10}$, $R^{11}$, and $R^{12}$ are as described herein.

In embodiments, $R^{13}$, $R^{15}$ and $R^{17}$ are independently hydrogen. In embodiments, $R^8$, $R^9$, $R^{11}$ and $R^{12}$ are independently hydrogen. In embodiments, $R^{18}$ is hydrogen. In embodiments, $R^{19}$ is hydrogen. n embodiments, $R^{19}$ is —$CH_3$. In embodiments, $R^{10}$ is fluorine, chlorine or iodine, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is fluorine, chlorine, bromine or iodine. In embodiments, $R^{10}$ is fluorine, chlorine or iodine. In embodiments, $R^{10}$ is fluorine. In embodiments, $R^8$, $R^9$, $R^{11}$, $R^{12}$, $R^{13}$, $R^{15}$, $R^{17}$, $R^{18}$ and $R^{19}$ are independently hydrogen.

In embodiments, $R^8$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8E}$-substituted or unsubstituted alkyl, $R^{8E}$-substituted or unsubstituted heteroalkyl, $R^{8E}$-substituted or unsubstituted cycloalkyl, $R^{8E}$-substituted or unsubstituted heterocycloalkyl, $R^{8E}$-substituted or unsubstituted aryl, or $R^{8E}$-substituted or unsubstituted heteroaryl. In embodiments, $R^8$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8E}$-substituted or unsubstituted $C_1$-$C_6$ alkyl, $R^{8E}$-substituted or unsubstituted 2 to 6 membered heteroalkyl, $R^{8E}$-substituted or unsubstituted $C_3$-$C_6$ cycloalkyl, $R^{8E}$-substituted or unsubstituted 3 to 6 membered heterocycloalkyl, $R^{8E}$-substituted or unsubstituted phenyl, or $R^{8E}$-substituted or unsubstituted 5 to 6 membered heteroaryl.

$R^{8E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8F}$-substituted or unsubstituted alkyl, $R^{8F}$-substituted or unsubstituted heteroalkyl, $R^{8F}$-substituted or unsubstituted cycloalkyl, $R^{8F}$-substituted or unsubstituted heterocycloalkyl, $R^{8F}$-substituted or unsubstituted aryl, or $R^{8F}$-substituted or unsubstituted heteroaryl. In embodiments, $R^{8E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^8$-substituted or unsubstituted $C_1$-$C_6$ alkyl, $R^{8E}$-substituted or unsubstituted 2 to 6 membered heteroalkyl, $R^{8F}$-substituted or unsubstituted $C_3$-$C_6$ cycloalkyl, $R^{8F}$-substituted or unsubstituted 3 to 6 membered heterocycloalkyl, $R^{8F}$-substituted or unsubstituted phenyl, or $R^{8F}$-substituted or unsubstituted 5 to 6 membered heteroaryl.

In embodiments, $R^9$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9E}$-substituted or unsubstituted alkyl, $R^{9E}$-substituted or unsubstituted heteroalkyl, $R^{9E}$-substituted or unsubstituted cycloalkyl, $R^{9E}$-substituted or unsubstituted heterocycloalkyl, $R^{9E}$-substituted or unsubstituted aryl, or $R^{9E}$-substituted or unsubstituted heteroaryl. In embodiments, $R^9$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9E}$-substituted or unsubstituted $C_1$-$C_6$ alkyl, $R^{9E}$-substituted or unsubstituted 2 to 6 membered heteroalkyl, $R^{9E}$-substituted or unsubstituted $C_3$-$C_6$ cycloalkyl, $R^{9E}$-substituted or unsubstituted 3 to 6 membered heterocycloalkyl, $R^{9E}$-substituted or unsubstituted phenyl, or $R^{9E}$-substituted or unsubstituted 5 to 6 membered heteroaryl.

$R^{9E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9F}$-substituted or unsubstituted alkyl, $R^{9F}$-substituted or unsubstituted heteroalkyl, $R^{9F}$-substituted or unsubstituted cycloalkyl, $R^{9F}$-substituted or unsubstituted heterocycloalkyl, $R^{9F}$-substituted or unsubstituted aryl, or $R^{9F}$-substituted or unsubstituted heteroaryl. In embodiments, $R^{9E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9F}$-substituted or unsubstituted $C_1$-$C_6$ alkyl, $R^{9F}$-substituted or unsubstituted 2 to 6 membered heteroalkyl, $R^{9F}$-substituted or unsubstituted $C_3$-$C_6$ cycloalkyl, $R^{9F}$-substituted or unsubstituted 3 to 6 membered heterocycloalkyl, $R^{9F}$-substituted or unsubstituted phenyl, or $R^{9F}$-substituted or unsubstituted 5 to 6 membered heteroaryl.

In embodiments, $R^{10}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10E}$-substituted or unsubstituted alkyl, $R^{10E}$-substituted or unsubstituted heteroalkyl, $R^{10E}$-substituted or unsubstituted cycloalkyl, $R^{10E}$-substituted or unsubstituted heterocycloalkyl, $R^{10E}$-substituted or unsubstituted aryl, or $R^{10E}$-substituted or unsubstituted heteroaryl. In embodiments, $R^{10}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10E}$-substituted or unsubstituted $C_1$-$C_6$ alkyl, $R^{10E}$-substituted or unsubstituted 2 to 6 membered heteroalkyl, $R^{10E}$-substituted or unsubstituted $C_3$-$C_6$ cycloalkyl, $R^{10E}$-substituted or unsubstituted 3 to 6 membered heterocycloalkyl, $R^{10E}$-substituted or unsubstituted phenyl, or $R^{10E}$-substituted or unsubstituted 5 to 6 membered heteroaryl. In embodiments, $R^{10}$ is fluorine, chlorine or iodine.

$R^{10E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10F}$-substituted or unsubstituted alkyl, $R^{10F}$-substituted or unsubstituted heteroalkyl, $R^{10F}$-substituted or unsubstituted cycloalkyl, $R^{10F}$-substituted or unsubstituted heterocycloalkyl, $R^{10F}$-substituted or unsubstituted aryl, or $R^{10F}$-substituted or unsubstituted heteroaryl. In embodiments, $R^{10E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{10F}$-substituted or unsubstituted $C_1$-$C_6$ alkyl, $R^{10F}$-substituted or unsubstituted 2 to 6 membered heteroalkyl, $R^{10F}$-substituted or unsubstituted $C_3$-$C_6$ cycloalkyl, $R^{10F}$-substituted or unsubstituted 3 to 6 membered heterocycloalkyl, $R^{10F}$-substituted or unsubstituted phenyl, or $R^{10F}$-substituted or unsubstituted 5 to 6 membered heteroaryl.

In embodiments, $R^{11}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11E}$-substituted or unsubstituted alkyl, $R^{11E}$-substituted or unsubstituted heteroalkyl, $R^{11E}$-substituted or unsubstituted cycloalkyl, $R^{11E}$-substituted or unsubstituted heterocycloalkyl, $R^{11E}$-substituted or unsubstituted aryl, or $R^{11E}$-substituted or unsubstituted heteroaryl. In embodiments, $R^{11}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11E}$-substituted or unsubstituted $C_1$-$C_6$ alkyl, $R^{11E}$-substituted or unsubstituted 2 to 6 membered heteroalkyl, $R^{11E}$-substituted or unsubstituted $C_3$-$C_6$ cycloalkyl, $R^{11E}$-substituted or unsubstituted 3 to 6 membered heterocycloalkyl, $R^{11E}$-substituted or unsubstituted phenyl, or $R^{11E}$-substituted or unsubstituted 5 to 6 membered heteroaryl.

$R^{11E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11F}$-substituted or unsubstituted alkyl, $R^{11F}$-substituted or unsubstituted heteroalkyl, $R^{11F}$-substituted or unsubstituted cycloalkyl, $R^{11F}$-substituted or unsubstituted heterocycloalkyl, $R^{11F}$-substituted or unsubstituted aryl, or $R^{11F}$-substituted or unsubstituted heteroaryl. In embodiments, $R^{11E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{11F}$-substituted or unsubstituted $C_1$-$C_6$ alkyl, $R^{11F}$-substituted or unsubstituted 2 to 6 membered heteroalkyl, $R^{11F}$ substituted or unsubstituted $C_3$-$C_6$ cycloalkyl, $R^{11F}$-substituted or unsubstituted 3 to 6 membered heterocycloalkyl, $R^{11F}$-substituted or unsubstituted phenyl, or $R^{11F}$-substituted or unsubstituted 5 to 6 membered heteroaryl.

In embodiments, $R^{12}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12E}$-substituted or unsubstituted alkyl, $R^{12E}$-substituted or unsubstituted heteroalkyl, $R^{12E}$-substituted or unsubstituted cycloalkyl, $R^{12E}$-substituted or unsubstituted heterocycloalkyl, $R^{12E}$-substituted or unsubstituted aryl, or $R^{12E}$-substituted or unsubstituted heteroaryl. In embodiments, $R^{12}$ is independently hydrogen, halogen,
—$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12E}$-substituted or unsubstituted $C_1$-$C_6$ alkyl, $R^{12E}$-substituted or unsubstituted 2 to 6 membered heteroalkyl, $R^{12E}$-substituted or unsubstituted $C_3$-$C_6$ cycloalkyl, $R^{12E}$-substituted or unsubstituted 3 to 6 membered heterocycloalkyl, $R^{12E}$-substituted or unsubstituted phenyl, or $R^{12E}$-substituted or unsubstituted 5 to 6 membered heteroaryl.

$R^{12E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12F}$-substituted or unsubstituted alkyl, $R^{12F}$-substituted or unsubstituted heteroalkyl, $R^{12F}$-substituted or unsubstituted cycloalkyl, $R^{12F}$-substituted or unsubstituted heterocycloalkyl, $R^{12F}$-substituted or unsubstituted aryl, or $R^{12F}$-substituted or unsubstituted heteroaryl. In embodiments, $R^{12E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{12F}$-substituted or unsubstituted $C_1$-$C_6$ alkyl, $R^{12F}$-substituted or unsubstituted 2 to 6 membered heteroalkyl, $R^{12F}$-substituted or unsubstituted $C_3$-$C_6$ cycloalkyl, $R^{12F}$-substituted or unsubstituted 3 to 6 membered heterocycloalkyl, $R^{12F}$-substituted or unsubstituted phenyl, or $R^{12F}$-substituted or unsubstituted 5 to 6 membered heteroaryl.

In embodiments, $R^{13}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13E}$-substituted or unsubstituted alkyl, $R^{13E}$-substituted or unsubstituted heteroalkyl, $R^{13E}$-substituted or unsubstituted cycloalkyl, $R^{13E}$-substituted or unsubstituted heterocycloalkyl, $R^{13E}$-substituted or unsubstituted aryl, or $R^{13E}$-substituted or unsubstituted heteroaryl. In embodiments, $R^{13}$ is independently hydrogen, halogen,
—$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13E}$-substituted or unsubstituted $C_1$-$C_6$ alkyl, $R^{13E}$-substituted or unsubstituted 2 to 6 membered heteroalkyl, $R^{13E}$-substituted or unsubstituted $C_3$-$C_6$ cycloalkyl, $R^{13E}$-substituted or unsubstituted 3 to 6 membered heterocycloalkyl, $R^{13E}$-substituted or unsubstituted phenyl, or $R^{13E}$-substituted or unsubstituted 5 to 6 membered heteroaryl.

$R^{13E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13F}$-substituted or unsubstituted alkyl, $R^{13F}$-substituted or unsubstituted heteroalkyl, $R^{13F}$-substituted or unsubstituted cycloalkyl, $R^{13F}$-substituted or unsubstituted heterocycloalkyl, $R^{13F}$-substituted or unsubstituted aryl, or $R^{13F}$-substituted or unsubstituted heteroaryl. In embodiments, $R^{13E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{13F}$-substituted or unsubstituted $C_1$-$C_6$ alkyl, $R^{13F}$-substituted or unsubstituted 2 to 6 membered heteroalkyl, $R^{13F}$-substituted or unsubstituted $C_3$-$C_6$ cycloalkyl, $R^{13F}$-substituted or unsubstituted 3 to 6 membered heterocycloalkyl, $R^{13F}$-substituted or unsubstituted phenyl, or $R^{13F}$-substituted or unsubstituted 5 to 6 membered heteroaryl.

In embodiments, $R^{14}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14E}$-substituted or unsubstituted alkyl, $R^{14E}$-substituted or unsubstituted heteroalkyl, $R^{14E}$-substituted or unsubstituted cycloalkyl, $R^{14E}$-substituted or unsubstituted heterocycloalkyl, $R^{14E}$-substituted or unsubstituted aryl, or $R^{14E}$-substituted or unsubstituted heteroaryl. In embodiments, $R^{14}$ is independently hydrogen, halogen,
—$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{14E}$-substituted or unsubstituted $C_1$-$C_6$ alkyl, $R^{14E}$-substituted or unsubstituted 2 to 6 membered heteroalkyl, $R^{14E}$-substituted or unsubstituted $C_3$-$C_6$ cycloalkyl, $R^{14E}$-substituted or unsubstituted 3 to 6 membered heterocycloalkyl, $R^{14E}$-substituted or unsubstituted phenyl, or $R^{14E}$-substituted or unsubstituted 5 to 6 membered heteroaryl.

$R^{14E}$ is independently oxo, halogen, —$CF_3$, —$CCl_3$, —$CBr_3$, —$CI_3$, —CN, —OH, —$NH_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14F}$-substituted or unsubstituted alkyl, R$^{14F}$-substituted or unsubstituted heteroalkyl, R$^{14F}$-substituted or unsubstituted cycloalkyl, R$^{14F}$-substituted or unsubstituted heterocycloalkyl, R$^{14F}$-substituted or unsubstituted aryl, or R$^{14F}$-substituted or unsubstituted heteroaryl. In embodiments, R$^{14E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14F}$-substituted or unsubstituted C$_1$-C$_6$ alkyl, R$^{14F}$-substituted or unsubstituted 2 to 6 membered heteroalkyl, R$^{14F}$-substituted or unsubstituted C$_3$-C$_6$ cycloalkyl, R$^{14F}$-substituted or unsubstituted 3 to 6 membered heterocycloalkyl, R$^{14F}$-substituted or unsubstituted phenyl, or R$^{14F}$-substituted or unsubstituted 5 to 6 membered heteroaryl.

In embodiments, R$^{15}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15E}$-substituted or unsubstituted alkyl, R$^{15E}$-substituted or unsubstituted heteroalkyl, R$^{15E}$-substituted or unsubstituted cycloalkyl, R$^{15E}$-substituted or unsubstituted heterocycloalkyl, R$^{15E}$-substituted or unsubstituted aryl, or R$^{15E}$-substituted or unsubstituted heteroaryl. In embodiments, R$^{15}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15E}$-substituted or unsubstituted C$_1$-C$_6$ alkyl, R$^{15E}$-substituted or unsubstituted 2 to 6 membered heteroalkyl, R$^{15E}$-substituted or unsubstituted C$_3$-C$_6$ cycloalkyl, R$^{15E}$-substituted or unsubstituted 3 to 6 membered heterocycloalkyl, R$^{15E}$-substituted or unsubstituted phenyl, or R$^{15E}$-substituted or unsubstituted 5 to 6 membered heteroaryl.

R$^{15E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15F}$-substituted or unsubstituted C$_1$-C$_6$ alkyl, R$^{15F}$-substituted or unsubstituted 2 to 6 membered heteroalkyl, R$^{15F}$-substituted or unsubstituted C$_3$-C$_6$ cycloalkyl, R$^{15F}$-substituted or unsubstituted 3 to 6 membered heterocycloalkyl, R$^{15F}$-substituted or unsubstituted phenyl, or R$^{15F}$-substituted or unsubstituted 5 to 6 membered heteroaryl.

In embodiments, R$^{16}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16E}$-substituted or unsubstituted alkyl, R$^{16E}$-substituted or unsubstituted heteroalkyl, R$^{16E}$-substituted or unsubstituted cycloalkyl, R$^{16E}$-substituted or unsubstituted heterocycloalkyl, R$^{16E}$-substituted or unsubstituted aryl, or R$^{16E}$-substituted or unsubstituted heteroaryl. In embodiments, R$^{16}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16E}$-substituted or unsubstituted C$_1$-C$_6$ alkyl, R$^{16E}$-substituted or unsubstituted 2 to 6 membered heteroalkyl, R$^{16E}$-substituted or unsubstituted C$_3$-C$_6$ cycloalkyl, R$^{16E}$-substituted or unsubstituted 3 to 6 membered heterocycloalkyl, R$^{16E}$-substituted or unsubstituted phenyl, or R$^{16E}$-substituted or unsubstituted 5 to 6 membered heteroaryl.

R$^{16E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16F}$-substituted or unsubstituted alkyl, R$^{16F}$-substituted or unsubstituted heteroalkyl, R$^{16F}$-substituted or unsubstituted cycloalkyl, R$^{16F}$-substituted or unsubstituted heterocycloalkyl, R$^{16F}$-substituted or unsubstituted aryl, or R$^{16F}$-substituted or unsubstituted heteroaryl. In embodiments, R$^{16E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16F}$-substituted or unsubstituted C$_1$-C$_6$ alkyl, R$^{16F}$-substituted or unsubstituted 2 to 6 membered heteroalkyl, R$^{16F}$-substituted or unsubstituted C$_3$-C$_6$ cycloalkyl, R$^{16F}$-substituted or unsubstituted 3 to 6 membered heterocycloalkyl, R$^{16F}$-substituted or unsubstituted phenyl, or R$^{16F}$-substituted or unsubstituted 5 to 6 membered heteroaryl.

In embodiments, R$^{17}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{17E}$-substituted or unsubstituted alkyl, R$^{17E}$-substituted or unsubstituted heteroalkyl, R$^{17E}$-substituted or unsubstituted cycloalkyl, R$^{17E}$-substituted or unsubstituted heterocycloalkyl, R$^{17E}$-substituted or unsubstituted aryl, or R$^{17E}$- substituted or unsubstituted heteroaryl. In embodiments, $R^{17}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17E}$-substituted or unsubstituted $C_1$-$C_6$ alkyl, $R^{17E}$-substituted or unsubstituted 2 to 6 membered heteroalkyl, $R^{17E}$-substituted or unsubstituted $C_3$-$C_6$ cycloalkyl, $R^{17E}$-substituted or unsubstituted 3 to 6 membered heterocycloalkyl, $R^{17E}$-substituted or unsubstituted phenyl, or $R^{17E}$-substituted or unsubstituted 5 to 6 membered heteroaryl.

$R^{17E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17F}$-substituted or unsubstituted alkyl, $R^{7F}$-substituted or unsubstituted heteroalkyl, $R^{7F}$-substituted or unsubstituted cycloalkyl, $R^{7F}$-substituted or unsubstituted heterocycloalkyl, $R^{17F}$-substituted or unsubstituted aryl, or $R^{17F}$-substituted or unsubstituted heteroaryl. In embodiments, $R^{17E}$ is independently oxo, halogen, —$CF_3$, —$CCl_3$, —$CBr_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{17F}$-substituted or unsubstituted $C_1$-$C_6$ alkyl, $R^{17F}$-substituted or unsubstituted 2 to 6 membered heteroalkyl, $R^{17F}$-substituted or unsubstituted $C_3$-$C_6$ cycloalkyl, $R^{17F}$-substituted or unsubstituted 3 to 6 membered heterocycloalkyl, $R^{17F}$-substituted or unsubstituted phenyl, or $R^{17F}$-substituted or unsubstituted 5 to 6 membered heteroaryl.

In embodiments, $R^{18}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18E}$-substituted or unsubstituted alkyl, $R^{18E}$-substituted or unsubstituted heteroalkyl, $R^{18E}$-substituted or unsubstituted cycloalkyl, $R^{18E}$-substituted or unsubstituted heterocycloalkyl, $R^{18E}$-substituted or unsubstituted aryl, or $R^{18E}$-substituted or unsubstituted heteroaryl. In embodiments, $R^{18}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18E}$-substituted or unsubstituted $C_1$-$C_6$ alkyl, $R^{18E}$-substituted or unsubstituted 2 to 6 membered heteroalkyl, $R^{18E}$-substituted or unsubstituted $C_3$-$C_6$ cycloalkyl, $R^{18E}$-substituted or unsubstituted 3 to 6 membered heterocycloalkyl, $R^{18E}$-substituted or unsubstituted phenyl, or $R^{18E}$-substituted or unsubstituted 5 to 6 membered heteroaryl.

$R^{18E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18F}$-substituted or unsubstituted alkyl, $R^{18F}$-substituted or unsubstituted heteroalkyl, $R^{18F}$-substituted or unsubstituted cycloalkyl, $R^{18F}$-substituted or unsubstituted heterocycloalkyl, $R^{18F}$-substituted or unsubstituted aryl, or $R^{18F}$-substituted or unsubstituted heteroaryl. In embodiments, $R^{18E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{18F}$-substituted or unsubstituted $C_1$-$C_6$ alkyl, $R^{18F}$-substituted or unsubstituted 2 to 6 membered heteroalkyl, $R^{18F}$-substituted or unsubstituted $C_3$-$C_6$ cycloalkyl, $R^{18F}$-substituted or unsubstituted 3 to 6 membered heterocycloalkyl, $R^{18F}$-substituted or unsubstituted phenyl, or $R^{18F}$-substituted or unsubstituted 5 to 6 membered heteroaryl.

In embodiments, $R^{19}$ is independently hydrogen, —COH, —C(O)$NHNH_2$, —C(O)OH, —$SO_2H$, —C(O)$NH_2$, $R^{19E}$-substituted or unsubstituted alkyl, $R^{19E}$-substituted or unsubstituted heteroalkyl, $R^{19E}$-substituted or unsubstituted cycloalkyl, $R^{19E}$-substituted or unsubstituted heterocycloalkyl, $R^{19E}$-substituted or unsubstituted aryl, or $R^{19E}$-substituted or unsubstituted heteroaryl.

$R^{19E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19F}$-substituted or unsubstituted alkyl, $R^{19F}$-substituted or unsubstituted heteroalkyl, $R^{19F}$-substituted or unsubstituted cycloalkyl, $R^{19F}$-substituted or unsubstituted heterocycloalkyl, $R^{19F}$-substituted or unsubstituted aryl, or $R^{19F}$-substituted or unsubstituted heteroaryl. In embodiments, $R^{19E}$ is independently oxo, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{19F}$-substituted or unsubstituted $C_1$-$C_6$ alkyl, $R^{19F}$-substituted or unsubstituted 2 to 6 membered heteroalkyl, $R^{19F}$-substituted or unsubstituted $C_3$-$C_6$ cycloalkyl, $R^{19F}$-substituted or unsubstituted 3 to 6 membered heterocycloalkyl, $R^{19F}$-substituted or unsubstituted phenyl, or $R^{19F}$-substituted or unsubstituted 5 to 6 membered heteroaryl.

In embodiments, $R^{8A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8AF}$-substituted or unsubstituted alkyl, $R^{8AF}$-substituted or unsubstituted heteroalkyl, $R^{8AF}$-substituted or unsubstituted cycloalkyl, $R^{8AF}$-substituted or unsubstituted heterocycloalkyl, $R^{8AF}$-substituted or unsubstituted aryl, or $R^{8AF}$- substituted or unsubstituted heteroaryl. In embodiments, $R^{8A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8AF}$-substituted or unsubstituted $C_1$-$C_6$ alkyl, $R^{8AF}$-substituted or unsubstituted 2 to 6 membered heteroalkyl, $R^{8AF}$-substituted or unsubstituted $C_3$-$C_6$ cycloalkyl, $R^{8AF}$-substituted or unsubstituted 3 to 6 membered heterocycloalkyl, $R^{8AF}$-substituted or unsubstituted phenyl, or $R^{8AF}$-substituted or unsubstituted 5 to 6 membered heteroaryl.

In embodiments, $R^{8B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8BF}$-substituted or unsubstituted alkyl, $R^{8BF}$-substituted or unsubstituted heteroalkyl, $R^{8BF}$-substituted or unsubstituted cycloalkyl, $R^{8BF}$-substituted or unsubstituted heterocycloalkyl, $R^{8BF}$-substituted or unsubstituted aryl, or $R^{8BF}$-substituted or unsubstituted heteroaryl. In embodiments, $R^{8B}$ is independently hydrogen, halogen, —$CF_3$, —$CCl_3$, —$CBr_3$, —$CI_{13}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8BF}$-substituted or unsubstituted $C_1$-$C_6$ alkyl, $R^{8BF}$-substituted or unsubstituted 2 to 6 membered heteroalkyl, $R^{8BF}$-substituted or unsubstituted $C_3$-$C_6$ cycloalkyl, $R^{8BF}$-substituted or unsubstituted 3 to 6 membered heterocycloalkyl, $R^{8BF}$-substituted or unsubstituted phenyl, or $R^{8BF}$-substituted or unsubstituted 5 to 6 membered heteroaryl.

In embodiments, $R^{8C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8CF}$-substituted or unsubstituted alkyl, $R^{8CF}$-substituted or unsubstituted heteroalkyl, $R^{8CF}$-substituted or unsubstituted cycloalkyl, $R^{8CF}$-substituted or unsubstituted heterocycloalkyl, $R^{8CF}$-substituted or unsubstituted aryl, or $R^{8CF}$-substituted or unsubstituted heteroaryl. In embodiments, $R^{8C}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8CF}$-substituted or unsubstituted $C_1$-$C_6$ alkyl, $R^{8CF}$-substituted or unsubstituted 2 to 6 membered heteroalkyl, $R^{8CF}$-substituted or unsubstituted $C_3$-$C_6$ cycloalkyl, $R^{8CF}$-substituted or unsubstituted 3 to 6 membered heterocycloalkyl, $R^{8CF}$-substituted or unsubstituted phenyl, or $R^{8CF}$-substituted or unsubstituted 5 to 6 membered heteroaryl. $R^{8B}$ and $R^{8C}$ bonded to the same nitrogen atom may optionally be joined to form a $R^{8CF}$-substituted or unsubstituted 3 to 6 membered heterocycloalkyl or $R^{8CF}$-substituted or unsubstituted 5 to 6 membered heteroaryl.

In embodiments, $R^{8D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8DF}$-substituted or unsubstituted alkyl, $R^{8DF}$-substituted or unsubstituted heteroalkyl, $R^{8DF}$-substituted or unsubstituted cycloalkyl, $R^{8DF}$-substituted or unsubstituted heterocycloalkyl, $R^{8DF}$-substituted or unsubstituted aryl, or $R^{8DF}$-substituted or unsubstituted heteroaryl. In embodiments, $R^{8D}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{8DF}$-substituted or unsubstituted $C_1$-$C_6$ alkyl, $R^{8DF}$-substituted or unsubstituted 2 to 6 membered heteroalkyl, $R^{8DF}$-substituted or unsubstituted $C_3$-$C_6$ cycloalkyl, $R^{8DF}$-substituted or unsubstituted 3 to 6 membered heterocycloalkyl, $R^{8DF}$-substituted or unsubstituted phenyl, or $R^{8DF}$-substituted or unsubstituted 5 to 6 membered heteroaryl.

In embodiments, $R^{9A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9AF}$-substituted or unsubstituted alkyl, $R^{9AF}$-substituted or unsubstituted heteroalkyl, $R^{9AF}$-substituted or unsubstituted cycloalkyl, $R^{9AF}$-substituted or unsubstituted heterocycloalkyl, $R^{9AF}$-substituted or unsubstituted aryl, or $R^{9AF}$-substituted or unsubstituted heteroaryl. In embodiments, $R^{9A}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9AF}$-substituted or unsubstituted $C_1$-$C_6$ alkyl, $R^{9AF}$-substituted or unsubstituted 2 to 6 membered heteroalkyl, $R^{9AF}$-substituted or unsubstituted $C_3$-$C_6$ cycloalkyl, $R^{9AF}$-substituted or unsubstituted 3 to 6 membered heterocycloalkyl, $R^{9AF}$-substituted or unsubstituted phenyl, or $R^{9AF}$-substituted or unsubstituted 5 to 6 membered heteroaryl.

In embodiments, $R^{9B}$ is independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{9BF}$-substituted or unsubstituted alkyl, $R^{9BF}$-substituted or unsubstituted heteroalkyl, $R^{9BF}$-substituted or unsubstituted cycloalkyl, $R^{9BF}$-substituted or unsubstituted heterocycloalkyl, $R^{9BF}$-substituted or unsubstituted aryl, or $R^{9BF}$-substituted or unsubstituted heteroaryl. In embodiments, $R^{9B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9BF}$-substituted or unsubstituted C$_1$-C$_6$ alkyl, R$^{9BF}$-substituted or unsubstituted 2 to 6 membered heteroalkyl, R$^{9BF}$-substituted or unsubstituted C$_3$-C$_6$ cycloalkyl, R$^{9BF}$-substituted or unsubstituted 3 to 6 membered heterocycloalkyl, R$^{9BF}$-substituted or unsubstituted phenyl, or R$^{9BF}$-substituted or unsubstituted 5 to 6 membered heteroaryl.

In embodiments, R$^{9C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9CF}$-substituted or unsubstituted alkyl, R$^{9CF}$-substituted or unsubstituted heteroalkyl, R$^{9CF}$-substituted or unsubstituted cycloalkyl, R$^{9CF}$-substituted or unsubstituted heterocycloalkyl, R$^{9CF}$-substituted or unsubstituted aryl, or R$^{9CF}$-substituted or unsubstituted heteroaryl. In embodiments, R$^{9C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9CF}$-substituted or unsubstituted C$_1$-C$_6$ alkyl, R$^{9CF}$-substituted or unsubstituted 2 to 6 membered heteroalkyl, R$^{9CF}$-substituted or unsubstituted C$_3$-C$_6$ cycloalkyl, R$^{9CF}$-substituted or unsubstituted 3 to 6 membered heterocycloalkyl, R$^{9CF}$-substituted or unsubstituted phenyl, or R$^{9CF}$-substituted or unsubstituted 5 to 6 membered heteroaryl. R$^{9B}$ and R$^{9C}$ bonded to the same nitrogen atom may optionally be joined to form a R$^{9CF}$-substituted or unsubstituted 3 to 6 membered heterocycloalkyl or R$^{9CF}$-substituted or unsubstituted 5 to 6 membered heteroaryl.

In embodiments, R$^{9D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9DF}$-substituted or unsubstituted alkyl, R$^{9DF}$-substituted or unsubstituted heteroalkyl, R$^{9DF}$-substituted or unsubstituted cycloalkyl, R$^{9DF}$-substituted or unsubstituted heterocycloalkyl, R$^{9DF}$-substituted or unsubstituted aryl, or R$^{9DF}$-substituted or unsubstituted heteroaryl. In embodiments, R$^{9D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{9DF}$-substituted or unsubstituted C$_1$-C$_6$ alkyl, R$^{9DF}$-substituted or unsubstituted 2 to 6 membered heteroalkyl, R$^{9DF}$-substituted or unsubstituted C$_3$-C$_6$ cycloalkyl, R$^{9DF}$-substituted or unsubstituted 3 to 6 membered heterocycloalkyl, R$^{9DF}$-substituted or unsubstituted phenyl, or R$^{9DF}$-substituted or unsubstituted 5 to 6 membered heteroaryl.

In embodiments, R$^{10A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10AF}$-substituted or unsubstituted alkyl, R$^{10AF}$-substituted or unsubstituted heteroalkyl, R$^{10AF}$-substituted or unsubstituted cycloalkyl, R$^{10AF}$-substituted or unsubstituted heterocycloalkyl, R$^{10AF}$-substituted or unsubstituted aryl, or R$^{10AF}$-substituted or unsubstituted heteroaryl. In embodiments, R$^{10A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10AF}$-substituted or unsubstituted C$_1$-C$_6$ alkyl, R$^{10A}$-substituted or unsubstituted 2 to 6 membered heteroalkyl, R$^{10A}$-substituted or unsubstituted C$_3$-C$_6$ cycloalkyl, R$^{10A}$-substituted or unsubstituted 3 to 6 membered heterocycloalkyl, R$^{10A}$-substituted or unsubstituted phenyl, or R$^{10AF}$-substituted or unsubstituted 5 to 6 membered heteroaryl.

In embodiments, R$^{10B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10BF}$-substituted or unsubstituted alkyl, R$^{10BF}$-substituted or unsubstituted heteroalkyl, R$^{10BF}$-substituted or unsubstituted cycloalkyl, R$^{10BF}$-substituted or unsubstituted heterocycloalkyl, R$^{10BF}$-substituted or unsubstituted aryl, or R$^{10BF}$-substituted or unsubstituted heteroaryl. In embodiments, R$^{10B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10BF}$-substituted or unsubstituted C$_1$-C$_6$ alkyl, R$^{10BF}$-substituted or unsubstituted 2 to 6 membered heteroalkyl, R$^{10BF}$-substituted or unsubstituted C$_3$-C$_6$ cycloalkyl, R$^{10BF}$-substituted or unsubstituted 3 to 6 membered heterocycloalkyl, R$^{10BF}$-substituted or unsubstituted phenyl, or R$^{10BF}$-substituted or unsubstituted 5 to 6 membered heteroaryl.

In embodiments, R$^{10C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10CF}$-substituted or unsubstituted alkyl, R$^{10CF}$-substituted or unsubstituted heteroalkyl, R$^{10CF}$-substituted or unsubstituted cycloalkyl, R$^{10CF}$-substituted or unsubstituted heterocycloalkyl, R$^{10CF}$-substituted or unsubstituted aryl, or R$^{10CF}$-substituted or unsubstituted heteroaryl. In embodiments, R$^{10C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10CF}$-substituted or unsubstituted C$_1$-C$_6$ alkyl, R$^{10CF}$-substituted or unsubstituted 2 to 6 membered heteroalkyl, R$^{10CF}$-substituted or unsubstituted C$_3$-C$_6$ cycloalkyl, R$^{10CF}$-substituted or unsubstituted 3 to 6 membered heterocycloalkyl, R$^{10CF}$-substituted or unsubstituted phenyl, or R$^{10CF}$-substituted or unsubstituted 5 to 6 membered heteroaryl. R$^{10B}$ and R$^{10C}$ bonded to the same nitrogen atom may optionally be joined to form a R$^{10CF}$-substituted or unsubstituted 3 to 6 membered heterocycloalkyl or R$^{10CF}$-substituted or unsubstituted 5 to 6 membered heteroaryl.

In embodiments, R$^{10D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10DF}$-substituted or unsubstituted alkyl, R$^{10DF}$-substituted or unsubstituted heteroalkyl, R$^{10DF}$-substituted or unsubstituted cycloalkyl, R$^{10DF}$-substituted or unsubstituted heterocycloalkyl, R$^{10DF}$-substituted or unsubstituted aryl, or R$^{10DF}$-substituted or unsubstituted heteroaryl. In embodiments, R$^{10D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{10DF}$-substituted or unsubstituted C$_1$-C$_6$ alkyl, R$^{10DF}$-substituted or unsubstituted 2 to 6 membered heteroalkyl, R$^{10DF}$-substituted or unsubstituted C$_3$-C$_6$ cycloalkyl, R$^{10DF}$-substituted or unsubstituted 3 to 6 membered heterocycloalkyl, R$^{10DF}$-substituted or unsubstituted phenyl, or R$^{10DF}$-substituted or unsubstituted 5 to 6 membered heteroaryl.

In embodiments, R$^{11A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11AF}$-substituted or unsubstituted alkyl, R$^{11AF}$-substituted or unsubstituted heteroalkyl, R$^{11AF}$-substituted or unsubstituted cycloalkyl, R$^{11AF}$-substituted or unsubstituted heterocycloalkyl, R$^{11AF}$-substituted or unsubstituted aryl, or R$^{11AF}$-substituted or unsubstituted heteroaryl. In embodiments, R$^{11A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11AF}$-substituted or unsubstituted C$_1$-C$_6$ alkyl, R$^{11AF}$-substituted or unsubstituted 2 to 6 membered heteroalkyl, R$^{11AF}$-substituted or unsubstituted C$_3$-C$_6$ cycloalkyl, R$^{11AF}$-substituted or unsubstituted 3 to 6 membered heterocycloalkyl, R$^{11AF}$-substituted or unsubstituted phenyl, or R$^{11AF}$-substituted or unsubstituted 5 to 6 membered heteroaryl.

In embodiments, R$^{11B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11BF}$-substituted or unsubstituted alkyl, R$^{11BF}$-substituted or unsubstituted heteroalkyl, R$^{11BF}$-substituted or unsubstituted cycloalkyl, R$^{11BF}$-substituted or unsubstituted heterocycloalkyl, R$^{11BF}$-substituted or unsubstituted aryl, or R$^{11BF}$-substituted or unsubstituted heteroaryl. In embodiments, R$^{11B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11BF}$-substituted or unsubstituted C$_1$-C$_6$ alkyl, R$^{11BF}$-substituted or unsubstituted 2 to 6 membered heteroalkyl, R$^{11BF}$-substituted or unsubstituted C$_3$-C$_6$ cycloalkyl, R$^{11BF}$-substituted or unsubstituted 3 to 6 membered heterocycloalkyl, R$^{11BF}$-substituted or unsubstituted phenyl, or R$^{11BF}$-substituted or unsubstituted 5 to 6 membered heteroaryl.

In embodiments, R$^{11C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11CF}$-substituted or unsubstituted alkyl, R$^{11CF}$-substituted or unsubstituted heteroalkyl, R$^{11CF}$-substituted or unsubstituted cycloalkyl, R$^{11CF}$-substituted or unsubstituted heterocycloalkyl, R$^{11CF}$-substituted or unsubstituted aryl, or R$^{11CF}$-substituted or unsubstituted heteroaryl. In embodiments, R$^{11C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11CF}$-substituted or unsubstituted C$_1$-C$_6$ alkyl, R$^{11CF}$-substituted or unsubstituted 2 to 6 membered heteroalkyl, R$^{11CF}$-substituted or unsubstituted C$_3$-C$_6$ cycloalkyl, R$^{11CF}$-substituted or unsubstituted 3 to 6 membered heterocycloalkyl, RCF-substituted or unsubstituted phenyl, or R$^{11CF}$-substituted or unsubstituted 5 to 6 membered heteroaryl. R$^{11B}$ and R$^{11C}$ bonded to the same nitrogen atom may optionally be joined to form a R$^{11CF}$-substituted or unsubstituted 3 to 6 membered heterocycloalkyl or R$^{11CF}$-substituted or unsubstituted 5 to 6 membered heteroaryl.

In embodiments, R$^{11D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11DF}$-substituted or unsubstituted alkyl, R$^{11DF}$-substituted or unsubstituted heteroalkyl, R$^{11DF}$-substituted or unsubstituted cycloalkyl, R$^{11DF}$-substituted or unsubstituted heterocycloalkyl, R$^{11DF}$-substituted or unsubstituted aryl, or R$^{11DF}$-substituted or unsubstituted heteroaryl. In embodiments, R$^{11D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{11DF}$-substituted or unsubstituted C$_1$-C$_6$ alkyl, R$^{11DF}$-substituted or unsubstituted 2 to 6 membered heteroalkyl, R$^{11DF}$-substituted or unsubstituted C$_3$-C$_6$ cycloalkyl, R$^{11DF}$-substituted or unsubstituted 3 to 6 membered heterocycloalkyl, R$^{11DF}$-substituted or unsubstituted phenyl, or R$^{11DF}$-substituted or unsubstituted 5 to 6 membered heteroaryl.

In embodiments, R$^{12A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12AF}$-substituted or unsubstituted alkyl, R$^{12AF}$-substituted or unsubstituted heteroalkyl, R$^{12AF}$-substituted or unsubstituted cycloalkyl, R$^{12AF}$-substituted or unsubstituted heterocycloalkyl, R$^{12AF}$-substituted or unsubstituted aryl, or R$^{12AF}$-substituted or unsubstituted heteroaryl. In embodiments, R$^{12A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12AF}$-substituted or unsubstituted C$_1$-C$_6$ alkyl, R$^{12AF}$-substituted or unsubstituted 2 to 6 membered heteroalkyl, R$^{12AF}$-substituted or unsubstituted C$_3$-C$_6$ cycloalkyl, R$^{12AF}$-substituted or unsubstituted 3 to 6 membered heterocycloalkyl, R$^{12AF}$-substituted or unsubstituted phenyl, or R$^{12AF}$-substituted or unsubstituted 5 to 6 membered heteroaryl.

In embodiments, R$^{12B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12BF}$-substituted or unsubstituted alkyl, R$^{12BF}$-substituted or unsubstituted heteroalkyl, R$^{12BF}$-substituted or unsubstituted cycloalkyl, R$^{12BF}$-substituted or unsubstituted heterocycloalkyl, R$^{12BF}$-substituted or unsubstituted aryl, or R$^{12BF}$-substituted or unsubstituted heteroaryl. In embodiments, R$^{12B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12BF}$-substituted or unsubstituted C$_1$-C$_6$ alkyl, R$^{12BF}$-substituted or unsubstituted 2 to 6 membered heteroalkyl, R$^{12BF}$-substituted or unsubstituted C$_3$-C$_6$ cycloalkyl, R$^{12BF}$-substituted or unsubstituted 3 to 6 membered heterocycloalkyl, R$^{12BF}$-substituted or unsubstituted phenyl, or R$^{12BF}$-substituted or unsubstituted 5 to 6 membered heteroaryl.

In embodiments, R$^{12C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12CF}$-substituted or unsubstituted alkyl, R$^{12CF}$-substituted or unsubstituted heteroalkyl, R$^{12CF}$-substituted or unsubstituted cycloalkyl, R$^{12CF}$-substituted or unsubstituted aryl, or R$^{12CF}$-substituted or unsubstituted heteroaryl. In embodiments, R$^{12C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12CF}$-substituted or unsubstituted C$_1$-C$_6$ alkyl, R$^{12CF}$-substituted or unsubstituted 2 to 6 membered heteroalkyl, R$^{12CF}$-substituted or unsubstituted C$_3$-C$_6$ cycloalkyl, R$^{12CF}$-substituted or unsubstituted 3 to 6 membered heterocycloalkyl, R$^{12CF}$-substituted or unsubstituted phenyl, or R$^{12CF}$-substituted or unsubstituted 5 to 6 membered heteroaryl. R$^{12B}$ and R$^{12C}$ bonded to the same nitrogen atom may optionally be joined to form a R$^{12CF}$-substituted or unsubstituted 3 to 6 membered heterocycloalkyl or R$^{12CF}$-substituted or unsubstituted 5 to 6 membered heteroaryl.

In embodiments, R$^{12D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12DF}$-substituted or unsubstituted alkyl, R$^{12DF}$-substituted or unsubstituted heteroalkyl, R$^{12DF}$-substituted or unsubstituted cycloalkyl, R$^{12DF}$-substituted or unsubstituted heterocycloalkyl, R$^{12DF}$-substituted or unsubstituted aryl, or R$^{12DF}$-substituted or unsubstituted heteroaryl. In embodiments, R$^{12D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{12DF}$-substituted or unsubstituted C$_1$-C$_6$ alkyl, R$^{12DF}$-substituted or unsubstituted 2 to 6 membered heteroalkyl, R$^{12DF}$-substituted or unsubstituted C$_3$-C$_6$ cycloalkyl, R$^{12DF}$-substituted or unsubstituted 3 to 6 membered heterocycloalkyl, R$^{12DF}$-substituted or unsubstituted phenyl, or R$^{12DF}$-substituted or unsubstituted 5 to 6 membered heteroaryl.

In embodiments, R$^{13A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{13AF}$-substituted or unsubstituted alkyl, R$^{13A}$-substituted or unsubstituted heteroalkyl, R$^{13A}$-substituted or unsubstituted cycloalkyl, R$^{13AF}$-substituted or unsubstituted heterocycloalkyl, R$^{13AF}$-substituted or unsubstituted aryl, or R$^{13AF}$-substituted or unsubstituted heteroaryl. In embodiments, R$^{13A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{13AF}$-substituted or unsubstituted C$_1$-C$_6$ alkyl, R$^{3AF}$-substituted or unsubstituted 2 to 6 membered heteroalkyl, R$^{13AF}$-substituted or unsubstituted C$_3$-C$_6$ cycloalkyl, R$^{13AF}$-substituted or unsubstituted 3 to 6 membered heterocycloalkyl, R$^{13AF}$- substituted or unsubstituted phenyl, or $R^{13AF}$-substituted or unsubstituted 5 to 6 membered heteroaryl.

In embodiments, $R^{13B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13BF}$-substituted or unsubstituted alkyl, $R^{13BF}$-substituted or unsubstituted heteroalkyl, $R^{13BF}$-substituted or unsubstituted cycloalkyl, $R^{13BF}$-substituted or unsubstituted heterocycloalkyl, $R^{13BF}$-substituted or unsubstituted aryl, or $R^{13BF}$-substituted or unsubstituted heteroaryl. In embodiments, $R^{13B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13BF}$-substituted or unsubstituted $C_1$-$C_6$ alkyl, $R^{13BF}$-substituted or unsubstituted 2 to 6 membered heteroalkyl, $R^{13BF}$-substituted or unsubstituted $C_3$-$C_6$ cycloalkyl, $R^{13BF}$-substituted or unsubstituted 3 to 6 membered heterocycloalkyl, $R^{13BF}$-substituted or unsubstituted phenyl, or $R^{13BF}$-substituted or unsubstituted 5 to 6 membered heteroaryl.

In embodiments, $R^{13C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13CF}$-substituted or unsubstituted alkyl, $R^{13CF}$-substituted or unsubstituted heteroalkyl, $R^{13C}$-substituted or unsubstituted cycloalkyl, $R^{13CF}$-substituted or unsubstituted heterocycloalkyl, $R^{13CF}$-substituted or unsubstituted aryl, or $R^{13CF}$-substituted or unsubstituted heteroaryl. In embodiments, $R^{13C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13CF}$-substituted or unsubstituted $C_1$-$C_6$ alkyl, $R^{13CF}$-substituted or unsubstituted 2 to 6 membered heteroalkyl, $R^{13CF}$-substituted or unsubstituted $C_3$-$C_6$ cycloalkyl, $R^{13CF}$-substituted or unsubstituted 3 to 6 membered heterocycloalkyl, $R^{13CF}$-substituted or unsubstituted phenyl, or $R^{13CF}$-substituted or unsubstituted 5 to 6 membered heteroaryl. $R^{13B}$ and $R^{13C}$ bonded to the same nitrogen atom may optionally be joined to form a $R^{13CF}$-substituted or unsubstituted 3 to 6 membered heterocycloalkyl or $R^{13CF}$-substituted or unsubstituted 5 to 6 membered heteroaryl.

In embodiments, $R^{13D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13DF}$-substituted or unsubstituted alkyl, $R^{13DF}$-substituted or unsubstituted heteroalkyl, $R^{13DF}$-substituted or unsubstituted cycloalkyl, $R^{13DF}$-substituted or unsubstituted heterocycloalkyl, $R^{13DF}$-substituted or unsubstituted aryl, or $R^{13DF}$-substituted or unsubstituted heteroaryl. In embodiments, $R^{13D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{13DF}$-substituted or unsubstituted $C_1$-$C_6$ alkyl, $R^{13DF}$-substituted or unsubstituted 2 to 6 membered heteroalkyl, $R^{13DF}$-substituted or unsubstituted $C_3$-$C_6$ cycloalkyl, $R^{13DF}$-substituted or unsubstituted 3 to 6 membered heterocycloalkyl, $R^{13DF}$-substituted or unsubstituted phenyl, or $R^{13DF}$-substituted or unsubstituted 5 to 6 membered heteroaryl.

In embodiments, $R^{14A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14AF}$-substituted or unsubstituted alkyl, $R^{14AF}$-substituted or unsubstituted heteroalkyl, $R^{14AF}$-substituted or unsubstituted cycloalkyl, $R^{14AF}$-substituted or unsubstituted heterocycloalkyl, $R^{14AF}$-substituted or unsubstituted aryl, or $R^{14AF}$-substituted or unsubstituted heteroaryl. In embodiments, $R^{14A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14AF}$-substituted or unsubstituted $C_1$-$C_6$ alkyl, $R^{14AF}$-substituted or unsubstituted 2 to 6 membered heteroalkyl, $R^{14AF}$-substituted or unsubstituted $C_3$-$C_6$ cycloalkyl, $R^{14AF}$-substituted or unsubstituted 3 to 6 membered heterocycloalkyl, $R^{14AF}$-substituted or unsubstituted phenyl, or $R^{14AF}$-substituted or unsubstituted 5 to 6 membered heteroaryl.

In embodiments, $R^{14B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14BF}$-substituted or unsubstituted alkyl, $R^{14BF}$-substituted or unsubstituted heteroalkyl, $R^{14BF}$-substituted or unsubstituted cycloalkyl, $R^{14BF}$-substituted or unsubstituted heterocycloalkyl, $R^{14BF}$-substituted or unsubstituted aryl, or $R^{14BF}$-substituted or unsubstituted heteroaryl. In embodiments, $R^{14B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{14BF}$-substituted or unsubstituted $C_1$-$C_6$ alkyl, $R^{14BF}$-substituted or unsubstituted 2 to 6 membered heteroalkyl, $R^{14BF}$-substituted or unsubstituted $C_3$-$C_6$ cycloalkyl, $R^{14BF}$-substituted or unsubstituted 3 to 6 membered heterocycloalkyl, $R^{14BF}$-substituted or unsubstituted phenyl, or $R^{14BF}$-substituted or unsubstituted 5 to 6 membered heteroaryl.

In embodiments, $R^{14C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14CF}$-substituted or unsubstituted alkyl, R$^{14CF}$-substituted or unsubstituted heteroalkyl, R$^{14CF}$-substituted or unsubstituted cycloalkyl, R$^{14CF}$-substituted or unsubstituted heterocycloalkyl, R$^{14CF}$-substituted or unsubstituted aryl, or R$^{14CF}$-substituted or unsubstituted heteroaryl. In embodiments, R$^{14C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14CF}$-substituted or unsubstituted C$_1$-C$_6$ alkyl, R$^{14CF}$-substituted or unsubstituted 2 to 6 membered heteroalkyl, R$^{14CF}$-substituted or unsubstituted C$_3$-C$_6$ cycloalkyl, R$^{14CF}$-substituted or unsubstituted 3 to 6 membered heterocycloalkyl, R$^{14CF}$-substituted or unsubstituted phenyl, or R$^{14CF}$-substituted or unsubstituted 5 to 6 membered heteroaryl. R$^{14B}$ and R$^{14C}$ bonded to the same nitrogen atom may optionally be joined to form a R$^{14CF}$-substituted or unsubstituted 3 to 6 membered heterocycloalkyl or R$^{14CF}$-substituted or unsubstituted 5 to 6 membered heteroaryl.

In embodiments, R$^{14D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14DF}$-substituted or unsubstituted alkyl, R$^{14DF}$-substituted or unsubstituted heteroalkyl, R$^{14DF}$-substituted or unsubstituted cycloalkyl, R$^{14DF}$-substituted or unsubstituted heterocycloalkyl, R$^{14DF}$-substituted or unsubstituted aryl, or R$^{14DF}$-substituted or unsubstituted heteroaryl. In embodiments, R$^{14D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{14DF}$-substituted or unsubstituted C$_1$-C$_6$ alkyl, R$^{14DF}$-substituted or unsubstituted 2 to 6 membered heteroalkyl, R$^{14DF}$-substituted or unsubstituted C$_3$-C$_6$ cycloalkyl, R$^{14DF}$-substituted or unsubstituted 3 to 6 membered heterocycloalkyl, R$^{14DF}$-substituted or unsubstituted phenyl, or R$^{14DF}$-substituted or unsubstituted 5 to 6 membered heteroaryl.

In embodiments, R$^{15A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15AF}$-substituted or unsubstituted alkyl, R$^{15AF}$-substituted or unsubstituted heteroalkyl, R$^{15AF}$-substituted or unsubstituted cycloalkyl, R$^{15AF}$-substituted or unsubstituted heterocycloalkyl, R$^{15AF}$-substituted or unsubstituted aryl, or R$^{15AF}$-substituted or unsubstituted heteroaryl. In embodiments, R$^{15A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15AF}$-substituted or unsubstituted C$_1$-C$_6$ alkyl, R$^{15AF}$-substituted or unsubstituted 2 to 6 membered heteroalkyl, R$^{15AF}$-substituted or unsubstituted C$_3$-C$_6$ cycloalkyl, R$^{15AF}$-substituted or unsubstituted 3 to 6 membered heterocycloalkyl, R$^{15AF}$-substituted or unsubstituted phenyl, or R$^{15AF}$-substituted or unsubstituted 5 to 6 membered heteroaryl.

In embodiments, R$^{15B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15BF}$-substituted or unsubstituted alkyl, R$^{15BF}$-substituted or unsubstituted heteroalkyl, R$^{15BF}$-substituted or unsubstituted cycloalkyl, R$^{15BF}$-substituted or unsubstituted heterocycloalkyl, R$^{15BF}$-substituted or unsubstituted aryl, or R$^{15BF}$-substituted or unsubstituted heteroaryl. In embodiments, R$^{15B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15BF}$-substituted or unsubstituted C$_1$-C$_6$ alkyl, R$^{15BF}$-substituted or unsubstituted 2 to 6 membered heteroalkyl, R$^{15BF}$-substituted or unsubstituted C$_3$-C$_6$ cycloalkyl, R$^{15BF}$-substituted or unsubstituted 3 to 6 membered heterocycloalkyl, R$^{15BF}$-substituted or unsubstituted phenyl, or R$^{15BF}$-substituted or unsubstituted 5 to 6 membered heteroaryl.

In embodiments, R$^{15C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15CF}$-substituted or unsubstituted alkyl, R$^{15CF}$-substituted or unsubstituted heteroalkyl, R$^{15CF}$-substituted or unsubstituted cycloalkyl, R$^{15CF}$-substituted or unsubstituted heterocycloalkyl, R$^{15CF}$-substituted or unsubstituted aryl, or R$^{15CF}$-substituted or unsubstituted heteroaryl. In embodiments, R$^{15C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15CF}$-substituted or unsubstituted C$_1$-C$_6$ alkyl, R$^{15CF}$-substituted or unsubstituted 2 to 6 membered heteroalkyl, R$^{15CF}$-substituted or unsubstituted C$_3$-C$_6$ cycloalkyl, R$^{15CF}$-substituted or unsubstituted 3 to 6 membered heterocycloalkyl, R$^{15CF}$-substituted or unsubstituted phenyl, or R$^{15CF}$-substituted or unsubstituted 5 to 6 membered heteroaryl. R$^{15B}$ and R$^{15C}$ bonded to the same nitrogen atom may optionally be joined to form a R$^{15CF}$-substituted or unsubstituted 3 to 6 membered heterocycloalkyl or R$^{15CF}$-substituted or unsubstituted 5 to 6 membered heteroaryl.

In embodiments, R$^{15D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15DF}$-substituted or unsubstituted alkyl, R$^{15DF}$-substituted or unsubstituted heteroalkyl, R$^{15DF}$-substituted or unsubstituted cycloalkyl, R$^{15DF}$-substituted or unsubstituted heterocycloalkyl, R$^{15DF}$-substituted or unsubstituted aryl, or R$^{15DF}$-substituted or unsubstituted heteroaryl. In embodiments, R$^{15D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{15DF}$-substituted or unsubstituted C$_1$-C$_6$ alkyl, R$^{15DF}$-substituted or unsubstituted 2 to 6 membered heteroalkyl, R$^{15DF}$-substituted or unsubstituted C$_3$-C$_6$ cycloalkyl, R$^{15DF}$-substituted or unsubstituted 3 to 6 membered heterocycloalkyl, R$^{15DF}$-substituted or unsubstituted phenyl, or R$^{15DF}$-substituted or unsubstituted 5 to 6 membered heteroaryl.

In embodiments, R$^{16A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16AF}$-substituted or unsubstituted alkyl, R$^{16AF}$-substituted or unsubstituted heteroalkyl, R$^{16AF}$-substituted or unsubstituted cycloalkyl, R$^{16AF}$-substituted or unsubstituted heterocycloalkyl, R$^{16AF}$-substituted or unsubstituted aryl, or R$^{16AF}$-substituted or unsubstituted heteroaryl. In embodiments, R$^{16A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16AF}$-substituted or unsubstituted C$_1$-C$_6$ alkyl, R$^{16AF}$-substituted or unsubstituted 2 to 6 membered heteroalkyl, R$^{16AF}$-substituted or unsubstituted C$_3$-C$_6$ cycloalkyl, R$^{16AF}$-substituted or unsubstituted 3 to 6 membered heterocycloalkyl, R$^{16AF}$-substituted or unsubstituted phenyl, or R$^{16AF}$-substituted or unsubstituted 5 to 6 membered heteroaryl.

In embodiments, R$^{16B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16BF}$-substituted or unsubstituted alkyl, R$^{16BF}$-substituted or unsubstituted heteroalkyl, R$^{16BF}$-substituted or unsubstituted cycloalkyl, R$^{16BF}$-substituted or unsubstituted heterocycloalkyl, R$^{16BF}$-substituted or unsubstituted aryl, or R$^{16BF}$-substituted or unsubstituted heteroaryl. In embodiments, R$^{16B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16BF}$-substituted or unsubstituted C$_1$-C$_6$ alkyl, R$^{16BF}$-substituted or unsubstituted 2 to 6 membered heteroalkyl, R$^{16BF}$-substituted or unsubstituted C$_3$-C$_6$ cycloalkyl, R$^{16BF}$-substituted or unsubstituted 3 to 6 membered heterocycloalkyl, R$^{16BF}$-substituted or unsubstituted phenyl, or R$^{16BF}$-substituted or unsubstituted 5 to 6 membered heteroaryl.

In embodiments, R$^{16C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16CF}$-substituted or unsubstituted alkyl, R$^{16CF}$-substituted or unsubstituted heteroalkyl, R$^{16CF}$-substituted or unsubstituted cycloalkyl, R$^{16CF}$-substituted or unsubstituted heterocycloalkyl, R$^{16CF}$-substituted or unsubstituted aryl, or R$^{16CF}$-substituted or unsubstituted heteroaryl. In embodiments, R$^{16C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16CF}$-substituted or unsubstituted C$_1$-C$_6$ alkyl, R$^{16CF}$-substituted or unsubstituted 2 to 6 membered heteroalkyl, R$^{16CF}$-substituted or unsubstituted C$_3$-C$_6$ cycloalkyl, R$^{16CF}$-substituted or unsubstituted 3 to 6 membered heterocycloalkyl, R$^{16CF}$-substituted or unsubstituted phenyl, or R$^{16CF}$-substituted or unsubstituted 5 to 6 membered heteroaryl. R$^{16B}$ and R$^{16C}$ bonded to the same nitrogen atom may optionally be joined to form a R$^{16CF}$-substituted or unsubstituted 3 to 6 membered heterocycloalkyl or R$^{16CF}$-substituted or unsubstituted 5 to 6 membered heteroaryl.

In embodiments, R$^{16D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16DF}$-substituted or unsubstituted alkyl, R$^{16DF}$-substituted or unsubstituted heteroalkyl, R$^{16DF}$-substituted or unsubstituted cycloalkyl, R$^{16DF}$-substituted or unsubstituted heterocycloalkyl, R$^{16DF}$-substituted or unsubstituted aryl, or R$^{16DF}$-substituted or unsubstituted heteroaryl. In embodiments, R$^{16D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{16DF}$-substituted or unsubstituted C$_1$-C$_6$ alkyl, R$^{16DF}$-substituted or unsubstituted 2 to 6 membered heteroalkyl, R$^{16DF}$-substituted or unsubstituted C$_3$-C$_6$ cycloalkyl, R$^{16DF}$-substituted or unsubstituted 3 to 6 membered heterocycloalkyl, R$^{16DF}$-substituted or unsubstituted phenyl, or R$^{16DF}$-substituted or unsubstituted 5 to 6 membered heteroaryl.

In embodiments, R$^{17A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{17AF}$-substituted or unsubstituted alkyl, R$^{17AF}$-substituted or unsubstituted heteroalkyl, R$^{17AF}$-substituted or unsubstituted cycloalkyl, $R^{17AF}$-substituted or unsubstituted heterocycloalkyl, $R^{17AF}$-substituted or unsubstituted aryl, or $R^{17AF}$-substituted or unsubstituted heteroaryl. In embodiments, $R^{17A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17AF}$-substituted or unsubstituted C$_1$-C$_6$ alkyl, $R^{17AF}$-substituted or unsubstituted 2 to 6 membered heteroalkyl, $R^{17AF}$ substituted or unsubstituted C$_3$-C$_6$ cycloalkyl, $R^{17AF}$-substituted or unsubstituted 3 to 6 membered heterocycloalkyl, $R^{17AF}$-substituted or unsubstituted phenyl, or $R^{7AF1}$-substituted or unsubstituted 5 to 6 membered heteroaryl.

In embodiments, $R^{17B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17BF}$-substituted or unsubstituted alkyl, $R^{17BF}$-substituted or unsubstituted heteroalkyl, $R^{17BF}$-substituted or unsubstituted cycloalkyl, $R^{17BF}$-substituted or unsubstituted heterocycloalkyl, $R^{17BF}$-substituted or unsubstituted aryl, or $R^{17BF}$-substituted or unsubstituted heteroaryl. In embodiments, $R^{17B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17BF}$-substituted or unsubstituted C$_1$-C$_6$ alkyl, $R^{17BF}$-substituted or unsubstituted 2 to 6 membered heteroalkyl, $R^{17BF}$-substituted or unsubstituted C$_3$-C$_6$ cycloalkyl, $R^{17BF}$-substituted or unsubstituted 3 to 6 membered heterocycloalkyl, $R^{7BF}$-substituted or unsubstituted phenyl, or $R^{17BF}$-substituted or unsubstituted 5 to 6 membered heteroaryl.

In embodiments, $R^{17C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17CF}$-substituted or unsubstituted alkyl, $R^{17CF}$-substituted or unsubstituted heteroalkyl, $R^{17CF}$-substituted or unsubstituted cycloalkyl, $R^{17CF}$-substituted or unsubstituted heterocycloalkyl, $R^{17CF}$-substituted or unsubstituted aryl, or $R^{17CF}$-substituted or unsubstituted heteroaryl. In embodiments, $R^{7C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17CF}$-substituted or unsubstituted C$_1$-C$_6$ alkyl, Rv$^{7CF}$-substituted or unsubstituted 2 to 6 membered heteroalkyl, $R^{17CF}$-substituted or unsubstituted C$_3$-C$_6$ cycloalkyl, $R^{17CF}$-substituted or unsubstituted 3 to 6 membered heterocycloalkyl, $R^{17CF}$-substituted or unsubstituted phenyl, or $R^{17CF}$-substituted or unsubstituted 5 to 6 membered heteroaryl. $R^{17B}$ and $R^{17C}$ bonded to the same nitrogen atom may optionally be joined to form a $R^{17CF}$-substituted or unsubstituted 3 to 6 membered heterocycloalkyl or $R^{17CF}$-substituted or unsubstituted 5 to 6 membered heteroaryl.

In embodiments, $R^{17D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17DF}$-substituted or unsubstituted alkyl, $R^{17DF}$-substituted or unsubstituted heteroalkyl, $R^{17DF}$-substituted or unsubstituted cycloalkyl, $R^{17DF}$-substituted or unsubstituted heterocycloalkyl, $R^{17DF}$-substituted or unsubstituted aryl, or $R^{17DF}$-substituted or unsubstituted heteroaryl. In embodiments, $R^{17D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{17DF}$-substituted or unsubstituted C$_1$-C$_6$ alkyl, $R^{17DF}$-substituted or unsubstituted 2 to 6 membered heteroalkyl, $R^{17DF}$-substituted or unsubstituted C$_3$-C$_6$ cycloalkyl, $R^{17DF}$-substituted or unsubstituted 3 to 6 membered heterocycloalkyl, $R^{17DF}$-substituted or unsubstituted phenyl, or $R^{17DF}$-substituted or unsubstituted 5 to 6 membered heteroaryl.

In embodiments, $R^{18A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{18AF}$-substituted or unsubstituted alkyl, $R^{18AF}$-substituted or unsubstituted heteroalkyl, $R^{18AF}$-substituted or unsubstituted cycloalkyl, $R^{18AF}$-substituted or unsubstituted heterocycloalkyl, $R^{18AF}$-substituted or unsubstituted aryl, or $R^{18AF}$-substituted or unsubstituted heteroaryl. In embodiments, $R^{18A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{18AF}$-substituted or unsubstituted C$_1$-C$_6$ alkyl, $R^{18AF}$-substituted or unsubstituted 2 to 6 membered heteroalkyl, $R^{18A}$-substituted or unsubstituted C$_3$-C$_6$ cycloalkyl, $R^{18AF}$-substituted or unsubstituted 3 to 6 membered heterocycloalkyl, $R^{18AF}$-substituted or unsubstituted phenyl, or $R^{18AF}$-substituted or unsubstituted 5 to 6 membered heteroaryl.

In embodiments, $R^{18B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, $R^{18BF}$-substituted or unsubstituted alkyl, $R^{18BF}$-substituted or unsubstituted heteroalkyl, $R^{18BF}$-substituted or unsubstituted cycloalkyl, $R^{18BF}$-substituted or unsubstituted heterocycloalkyl, $R^{18BF}$-substituted or unsubstituted aryl, or $R^{18BF}$-substituted or unsubstituted heteroaryl. In embodiments, $R^{18B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18BF}$-substituted or unsubstituted C$_1$-C$_6$ alkyl, R$^{18BF}$-substituted or unsubstituted 2 to 6 membered heteroalkyl, R$^{18BF}$-substituted or unsubstituted C$_3$-C$_6$ cycloalkyl, R$^{18BF}$-substituted or unsubstituted 3 to 6 membered heterocycloalkyl, R$^{18BF}$-substituted or unsubstituted phenyl, or R$^{18BF}$-substituted or unsubstituted 5 to 6 membered heteroaryl.

In embodiments, R$^{18C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18CF}$-substituted or unsubstituted alkyl, R$^{18CF}$-substituted or unsubstituted heteroalkyl, R$^{18CF}$-substituted or unsubstituted cycloalkyl, R$^{18CF}$-substituted or unsubstituted heterocycloalkyl, R$^{18CF}$-substituted or unsubstituted aryl, or R$^{18CF}$-substituted or unsubstituted heteroaryl. In embodiments, R$^{18C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18CF}$-substituted or unsubstituted C$_1$-C$_6$ alkyl, R$^{18CF}$-substituted or unsubstituted 2 to 6 membered heteroalkyl, R$^{18CF}$-substituted or unsubstituted C$_3$-C$_6$ cycloalkyl, R$^{18CF}$-substituted or unsubstituted 3 to 6 membered heterocycloalkyl, R$^{18C}$-substituted or unsubstituted phenyl, or R$^{18CF}$-substituted or unsubstituted 5 to 6 membered heteroaryl. R$^{18B}$ and R$^{18C}$ bonded to the same nitrogen atom may optionally be joined to form a R$^{18CF}$-substituted or unsubstituted 3 to 6 membered heterocycloalkyl or R$^{18CF}$-substituted or unsubstituted 5 to 6 membered heteroaryl.

In embodiments, R$^{18D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18DF}$-substituted or unsubstituted alkyl, R$^{18DF}$-substituted or unsubstituted heteroalkyl, R$^{18DF}$-substituted or unsubstituted cycloalkyl, R$^{18DF}$-substituted or unsubstituted heterocycloalkyl, R$^{18DF}$-substituted or unsubstituted aryl, or R$^{18DF}$-substituted or unsubstituted heteroaryl. In embodiments, R$^{18D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{18DF}$-substituted or unsubstituted C$_1$-C$_6$ alkyl, R$^{18DF}$-substituted or unsubstituted 2 to 6 membered heteroalkyl, R$^{18DF}$-substituted or unsubstituted C$_3$-C$_6$ cycloalkyl, R$^{18DF}$-substituted or unsubstituted 3 to 6 membered heterocycloalkyl, R$^{18DF}$-substituted or unsubstituted phenyl, or R$^{18DF}$-substituted or unsubstituted 5 to 6 membered heteroaryl.

In embodiments, R$^{19A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19A}$-substituted or unsubstituted alkyl, R$^{19AF}$-substituted or unsubstituted heteroalkyl, R$^{19A}$-substituted or unsubstituted cycloalkyl, R$^{19AF}$-substituted or unsubstituted heterocycloalkyl, R$^{19AF}$-substituted or unsubstituted aryl, or R$^{19AF}$-substituted or unsubstituted heteroaryl. In embodiments, R$^{19A}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19AF}$-substituted or unsubstituted C$_1$-C$_6$ alkyl, R$^{19AF}$-substituted or unsubstituted 2 to 6 membered heteroalkyl, R$^{19AF}$-substituted or unsubstituted C$_3$-C$_6$ cycloalkyl, R$^{19AF}$-substituted or unsubstituted 3 to 6 membered heterocycloalkyl, R$^{18AF}$-substituted or unsubstituted phenyl, or R$^{19AF}$-substituted or unsubstituted 5 to 6 membered heteroaryl.

In embodiments, R$^{19B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19BF}$-substituted or unsubstituted alkyl, R$^{19BF}$-substituted or unsubstituted heteroalkyl, R$^{19BF}$-substituted or unsubstituted cycloalkyl, R$^{19BF}$-substituted or unsubstituted heterocycloalkyl, R$^{19BF}$-substituted or unsubstituted aryl, or R$^{19BF}$-substituted or unsubstituted heteroaryl. In embodiments, R$^{19B}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19BF}$-substituted or unsubstituted C$_1$-C$_6$ alkyl, R$^{19BF}$-substituted or unsubstituted 2 to 6 membered heteroalkyl, R$^{19BF}$-substituted or unsubstituted C$_3$-C$_6$ cycloalkyl, R$^{19BF}$-substituted or unsubstituted 3 to 6 membered heterocycloalkyl, R$^{19BF}$-substituted or unsubstituted phenyl, or R$^{19BF}$-substituted or unsubstituted 5 to 6 membered heteroaryl.

In embodiments, R$^{19C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19CF}$-substituted or unsubstituted alkyl, R$^{19CF}$-substituted or unsubstituted heteroalkyl, R$^{19CF}$-substituted or unsubstituted cycloalkyl, R$^{19CF}$-substituted or unsubstituted heterocycloalkyl, R$^{19CF}$-substituted or unsubstituted aryl, or R$^{19CF}$-substituted or unsubstituted heteroaryl. In embodiments, R$^{19C}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19CF}$-substituted or unsubstituted C$_1$-C$_6$ alkyl, R$^{19CF}$-substituted or unsubstituted 2 to 6 membered heteroalkyl, R$^{19CF}$-substituted or unsubstituted C$_3$-C$_6$ cycloalkyl, R$^{19CF}$-substituted or unsubstituted 3 to 6 membered heterocycloalkyl, R$^{19CF}$-substituted or unsubstituted phenyl, or R$^{19CF}$-substituted or unsubstituted 5 to 6 membered heteroaryl. R$^{19B}$ and R$^{19C}$ bonded to the same nitrogen atom may optionally be joined to form a R$^{19CF}$-substituted or unsubstituted 3 to 6 membered heterocycloalkyl or R$^{19CF}$-substituted or unsubstituted 5 to 6 membered heteroaryl.

In embodiments, R$^{19D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19DF}$-substituted or unsubstituted alkyl, R$^{19DF}$-substituted or unsubstituted heteroalkyl, R$^{19DF}$-substituted or unsubstituted cycloalkyl, R$^{19DF}$-substituted or unsubstituted heterocycloalkyl, R$^{19DF}$-substituted or unsubstituted aryl, or R$^{19DF}$-substituted or unsubstituted heteroaryl. In embodiments, R$^{19D}$ is independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{19DF}$-substituted or unsubstituted C$_1$-C$_6$ alkyl, R$^{19DF}$-substituted or unsubstituted 2 to 6 membered heteroalkyl, R$^{19DF}$-substituted or unsubstituted C$_3$-C$_6$ cycloalkyl, R$^{19DF}$-substituted or unsubstituted 3 to 6 membered heterocycloalkyl, R$^{19DF}$-substituted or unsubstituted phenyl, or R$^{19DF}$-substituted or unsubstituted 5 to 6 membered heteroaryl.

In embodiments, L$^1$ is independently a bond, O, N(R$^{20}$), S or R$^{20E}$-substituted or unsubstituted C$_1$-C$_3$ alkylene. In embodiments, L$^1$ is a bond or substituted or unsubstituted C$_1$-C$_3$ alkylene.

In embodiments, R$^{20}$ is independently hydrogen, —COH, —C(O)NHNH$_2$, —C(O)OH, —SO$_2$H, —C(O)NH$_2$, R$^{20E}$-substituted or unsubstituted alkyl, R$^{20E}$-substituted or unsubstituted heteroalkyl, R$^{20E}$-substituted or unsubstituted cycloalkyl, R$^{20E}$-substituted or unsubstituted heterocycloalkyl, R$^{20E}$-substituted or unsubstituted aryl, or R$^{20E}$-substituted or unsubstituted heteroaryl.

R$^{20E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{20F}$-substituted or unsubstituted alkyl, R$^{20F}$-substituted or unsubstituted heteroalkyl, R$^{20F}$-substituted or unsubstituted cycloalkyl, R$^{20F}$-substituted or unsubstituted heterocycloalkyl, R$^{20F}$-substituted or unsubstituted aryl, or R$^{20F}$-substituted or unsubstituted heteroaryl. In embodiments, R$^{20E}$ is independently oxo, halogen, —CF$_3$, —CCl$_3$, —CBr$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{20F}$-substituted or unsubstituted C$_1$-C$_6$ alkyl, R$^{20F}$-substituted or unsubstituted 2 to 6 membered heteroalkyl, R$^{20F}$-substituted or unsubstituted C$_3$-C$_6$ cycloalkyl, R$^{20F}$-substituted or unsubstituted 3 to 6 membered heterocycloalkyl, R$^{20F}$-substituted or unsubstituted phenyl, or R$^{20F}$-substituted or unsubstituted 5 to 6 membered heteroaryl.

In embodiments, R$^{8F}$, R$^{9F}$, R$^{10F}$, R$^{11F}$, R$^{12F}$, R$^{13F}$, R$^{14F}$, R$^{15F}$, R$^{16F}$, R$^{17F}$, R$^{18F}$, R$^{19F}$, R$^{20F}$, R$^{8AF}$, R$^{8BF}$, R$^{8CF}$, R$^{8DF}$, R$^{9AF}$, R$^{9BF}$, R$^{9CF}$, R$^{9DF}$, R$^{10AF}$, R$^{11BF}$, R$^{10CF}$, R$^{10DF}$, R$^{11A}$, R$^{11BF}$, R$^{11CF}$, R$^{11DF}$, R$^{12AF}$, R$^{12BF}$, R$^{12CF}$, R$^{12DF}$, R$^{13AF}$, R$^{13BF}$, R$^{13CF}$, R$^{13DF}$, R$^{14AF}$, R$^{14BF}$, R$^{14CF}$, R$^{14DF}$, R$^{15AF}$, R$^{15BF}$, R$^{15CF}$, R$^{15DF}$, R$^{16A}$, R$^{16BF}$, R$^{16CF}$, R$^{16DF}$, R$^{17AF}$, R$^{17BF}$, R$^{17CF}$, R$^{17DF}$, R$^{18AF}$, R$^{18BF}$, R$^{18CF}$, R$^{18DF}$, R$^{19AF}$, R$^{19BF}$, R$^{19CF}$ and R$^{19DF}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl. In embodiments, R$^{8F}$, R$^{9F}$, R$^{10F}$, R$^{11F}$, R$^{12F}$, R$^{13F}$, R$^{14F}$, R$^{15F}$, R$^{16F}$, R$^{17F}$, R$^{18F}$, R$^{19F}$, R$^{20F}$, R$^{8AF}$, R$^{8BF}$, R$^{8CF}$, R$^{8DF}$, R$^{9AF}$, R$^{9BF}$, R$^{9CF}$, R$^{9DF}$, R$^{10AF}$, R$^{10BF}$, R$^{10CF}$, R$^{10DF}$, R$^{11AF}$, R$^{11BF}$, R$^{11CF}$, R$^{11DF}$, R$^{12AF}$, R$^{12BF}$, R$^{12CF}$, R$^{12DF}$, R$^{13AF}$, R$^{13BF}$, R$^{13CF}$, R$^{13DF}$, R$^{14AF}$, R$^{14BF}$, R$^{14CF}$, R$^{14DF}$, R$^{15AF}$, R$^{15BF}$, R$^{15CF}$, R$^{15DF}$, R$^{16AF}$, R$^{16BF}$, R$^{16CF}$, R$^{16DF}$, R$^{17AF}$, R$^{17BF}$, R$^{17CF}$, R$^{17DF}$, R$^{18AF}$, R$^{18BF}$, R$^{18CF}$, R$^{18DF}$, R$^{19AF}$, R$^{19BF}$, R$^{19CF}$ and R$^{19DF}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In some embodiments, a compound as described herein may include multiple instances of R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{20E}$, m1, n1, v1, and/or other variables. In such embodiments, each variable may optional be different and be appropriately labeled to distinguish each group for greater clarity. For example, where each R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{20E}$, m1, n1, v1, is different, they may be referred to, for example, as R$^{8.1}$, R$^{8.2}$, R$^{8.3}$, R$^{8.4}$, R$^{8.5}$, R$^{8.6}$, R$^{9.1}$, R$^{9.2}$, R$^{9.3}$, R$^{9.4}$, R$^{9.5}$, R$^{9.6}$, R$^{10.1}$, R$^{10.2}$, R$^{10.3}$, R$^{10.4}$, R$^{10.5}$, R$^{10.6}$, R$^{11.1}$, R$^{11.2}$, R$^{11.3}$, R$^{11.4}$, R$^{11.5}$, R$^{11.6}$, R$^{12.1}$, R$^{12.2}$, R$^{12.3}$, R$^{12.4}$, R$^{12.5}$, R$^{12.6}$, R$^{13.1}$, R$^{13.2}$, R$^{13.3}$, R$^{13.4}$, R$^{13.5}$, R$^{13.6}$, R$^{14.1}$, R$^{14.2}$, R$^{14.3}$, R$^{14.4}$, R$^{14.5}$, R$^{14.6}$, R$^{15.1}$, R$^{15.2}$, R$^{15.3}$, R$^{15.4}$, R$^{15.5}$, R$^{15.6}$, R$^{16.1}$, R$^{16.2}$, R$^{16.3}$, R$^{16.4}$, R$^{16.5}$, R$^{16.6}$, R$^{17.1}$, R$^{17.2}$, R$^{17.3}$, R$^{17.4}$, R$^{17.5}$, R$^{17.6}$, R$^{18.1}$, R$^{18.2}$, R$^{18.3}$, R$^{18.4}$, R$^{18.5}$, R$^{18.6}$, R$^{19.1}$, R$^{19.2}$, R$^{19.4}$, R$^{19.5}$, R$^{19.6}$, R$^{20.1}$, R$^{20.2}$, R$^{20.3}$, R$^{20.4}$, R$^{20.5}$, R$^{20.6}$, R$^{20E.1}$, R$^{20E.2}$, R$^{20E.3}$, R$^{20E.4}$, R$^{20E.5}$, R$^{20E.6}$, m1$^1$, m1$^2$, m1$^3$, m1$^4$, m1$^5$, m1$^6$, n1$^1$, n1$^2$, n1$^3$, n1$^4$, n1$^5$, n1$^6$, v1$^1$, v1$^2$, v1$^3$, v1$^4$, v1$^5$, v1$^6$, respectively, wherein the definition of R$^8$ is assumed by R$^{8.1}$, R$^{8.2}$, R$^{8.3}$, R$^{8.4}$, R$^{8.5}$, R$^{8.6}$, the definition of R$^9$ is assumed by R$^{9.1}$, R$^{9.2}$, R$^{9.3}$, R$^{9.4}$, R$^{9.5}$, R$^{9.6}$, the definition of R$^{10}$ is assumed by R$^{10.1}$, R$^{10.2}$, R$^{10.3}$, R$^{10.4}$, R$^{10.5}$, R$^{10.6}$, the definition of R$^{11}$ is assumed by R$^{11.1}$, R$^{11.2}$, R$^{11.3}$, R$^{11.4}$, R$^{11.5}$, R$^{11.6}$, R$^{11.7}$, the definition of R$^{12}$ is assumed by R$^{12.1}$, R$^{12.2}$, R$^{12.3}$, R$^{12.4}$, R$^{12.5}$, R$^{12.6}$, R$^{12.7}$, the definition of R$^{13}$ is assumed by R$^{13.1}$, R$^{13.2}$, R$^{13.3}$, R$^{13.4}$, R$^{13.5}$, R$^{13.6}$, the definition of R$^{14}$ is assumed by R$^{14.1}$, R$^{14.2}$, R$^{14.3}$, R$^{14.4}$, R$^{14.5}$, R$^{14.6}$, the definition of $R^{15}$ is assumed by $R^{15.1}$, $R^{15.2}$, $R^{15.3}$, $R^{15.4}$, $R^{15.5}$, $R^{15.6}$, the definition of $R^{16}$ is assumed by $R^{16.1}$, $R^{16.2}$, $R^{16.3}$, $R^{16.4}$, $R^{16.5}$, $R^{16.6}$, the definition of $R^{17}$ is assumed by $R^{17.1}$, $R^{17.2}$, $R^{17.3}$, $R^{17.4}$, $R^{17.5}$, $R^{17.6}$, the definition of $R^{18}$ is assumed by $R^{18.1}$, $R^{18.2}$, $R^{18.3}$, $R^{18.4}$, $R^{18.5}$, $R^{18.6}$, the definition of $R^{19}$ is assumed by $R^{19.1}$, $R^{19.2}$, $R^{19.3}$, $R^{19.4}$, $R^{19.5}$, $R^{19.6}$, the definition of $R^{20}$ is assumed by $R^{20.1}$, $R^{20.2}$, $R^{20.3}$, $R^{20.4}$, $R^{20.5}$, $R^{20.6}$, the definition of $R^{20E}$ is assumed by $R^{20E.1}$, $R^{20E.2}$, $R^{20E.3}$, $R^{20E.4}$, $R^{20E.5}$, $R^{20E.6}$, the definition of m1 is assumed by m1, $m1^2$, $m1^3$, $m1^4$, $m1^5$, $m1^6$, the definition of n1 is assumed by $n1^1$, $n1^2$, $n1^3$, $n1^4$, $n1^5$, $n1^6$, and the definition of v1 is assumed by $v1^1$, $v1^2$, $v1^3$, $v1^4$, $v1^5$, $v1^6$.

The variables used within a definition of $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{20E}$, m1, n1, v1, and/or other variables that appear at multiple instances and are different may similarly be appropriately labeled to distinguish each group for greater clarity.

In embodiments, the compound is

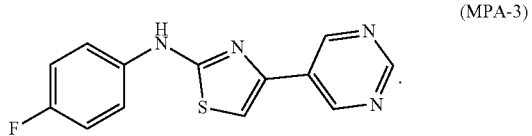 [SMILES: Fc1ccc(Nc2nc(-c3cncnc3)cs2)cc1]
(MPA-3)

In embodiments, the compound is

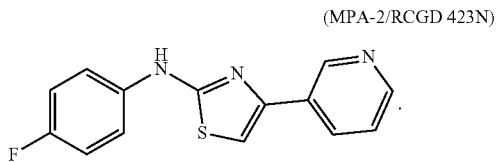 [SMILES: Fc1ccc(Nc2nc(-c3cccnc3)cs2)cc1]
(MPA-2/RCGD 423N)

In embodiments, the compound is

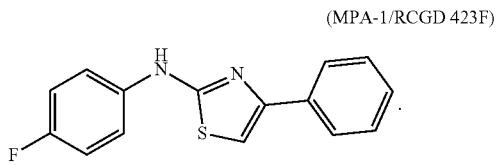 [SMILES: Fc1ccc(Nc2nc(-c3ccccc3)cs2)cc1]
(MPA-1/RCGD 423F)

In embodiments, the compound is

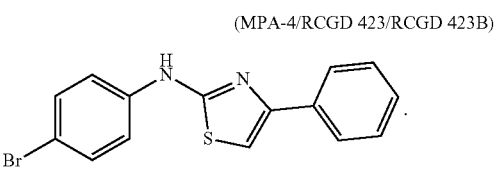 [SMILES: Brc1ccc(Nc2nc(-c3ccccc3)cs2)cc1]
(MPA-4/RCGD 423/RCGD 423B)

In an aspect is provided a method for inducing hair regeneration in a subject in need thereof, the method including administering to the subject an effective amount of a compound described herein (e.g. with structure of Formula (III), (IIIa), (IIIb) or (IIIc) as set forth herein) including embodiments thereof. Hair of the subject is thereby regenerated. In embodiments, inducing hair regeneration results in an increase in hair growth relative to the absence of the compound. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the inducement results in an increase in hair regeneration relative to the absence of the compound.

In an aspect is provided a method for activating a quiescent hair follicle stem cell (HFSC) in a subject in need thereof, the method including contacting a quiescent HFSC with an effective amount of a compound described herein (e.g. with structure of Formula (III), (IIIa), (IIIb) or (IIIc) as set forth herein) including embodiments thereof. The quiescent HFSC is thereby activated. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the activating results in an increase in quiescent HFSC activity (e.g. activity resulting in hair growth) relative to the absence of the compound.

In an aspect is provided a method for inducing glycolysis in a hair follicle stem cell (HFSC), the method including contacting a HFSC with an effective amount of a compound described herein (e.g. with structure of Formula (III), (IIIa), (IIIb) or (IIIc) as set forth herein) including embodiments thereof. Glycolysis in the HFSC is thereby induced. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the method is performed in vitro. In embodiments, the HFSC is in a subject in need thereof, wherein the method includes administering to the subject an effective amount of the compound. In embodiments, the inducing results in an increase in glycolysis relative to the absence of the compound. In embodiments, the inducing results in an increase in hair growth relative to the absence of the compound.

In an aspect is provided a method for activating lactate dehydrogenase in a hair follicle stem cell (HFSC), the method including contacting a HFSC with an effective amount of a compound described herein (e.g. with structure of Formula (III), (IIIa), (IIIb) or (IIIc) as set forth herein) including embodiments thereof. Lactate dehydrogenase in the HFSC is thereby activated. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the method is performed in vitro. In embodiments, the HFSC is in a subject in need thereof, wherein the method includes administering to the subject an effective amount of the compound. In embodiments, the activating results in an increase in lactate dehydrogenase activity (e.g. an activity the results in hair growth) relative to the absence of the compound.

In another aspect, there is provided a method for hair regeneration. The method includes administering to a subject in need thereof an effective amount of a compound described herein (e.g. with structure of Formula (III), (IIIa), (IIIb) or (IIIc) as set forth herein) including embodiments thereof. The hair of the subject is thereby regenerated. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the hair regeneration is an increased amount of hair growth relative to the absence of the compound.

In another aspect, there is provided a method for activating a quiescent hair follicle stem cell (HFSC). The method includes contacting a quiescent HFSC with an effective amount of a compound described herein (e.g. with structure of Formula (III), (IIIa), (IIIb) or (IIIc) as set forth herein) including embodiments thereof. The quiescent HFSC is thereby activated. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B.

In embodiments, the quiescent HFSC is a human HFSC. In embodiments, the quiescent HFSC is within a human subject. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B.

In another aspect, there is provided a method for inducing glycolysis in a hair follicle stem cell (HFSC). The method includes contacting a HFSC with an effective amount of a compound described herein (e.g. with structure of Formula (III), (IIIa), (IIIb) or (IIIc) as set forth herein) including embodiments thereof. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the method is performed in vitro. In embodiments, the HFSC is in a subject in need thereof, wherein the method includes administering to the subject an effective amount of the compound. In embodiments, the inducing results in an increase in glycolysis (e.g. an activity the results in hair growth) relative to the absence of the compound.

In embodiments, the HFSC is a human HFSC. In embodiments, the HFSC is within a human subject. In embodiments, the HFSC is a quiescent HFSC.

In embodiments, levels of glycolytic metabolites in the cell are increased relative to the absence of administration of the compound. In embodiments, the glycolytic metabolites are glucose, fructose-6-phosphate, fructose-bisphosphate, dihydroxyacetone phosphate, 3-phosphoglycerate or lactate. In embodiments, the glycolytic metabolites is glucose. In embodiments, the glycolytic metabolites is fructose-6-phosphate. In embodiments, the glycolytic metabolites is fructose-bisphosphate. In embodiments, the glycolytic metabolites is dihydroxyacetone phosphate. In embodiments, the glycolytic metabolites is 3-phosphoglycerate. In embodiments, the glycolytic metabolites is lactate.

In another aspect, there is provided a method for activation of lactate dehydrogenase in a hair follicle stem cell (HFSC). The method includes contacting a HFSC with an effective amount of a compound described herein (e.g. with structure of Formula (III), (IIIa), (IIIb) or (IIIc) as set forth herein) including embodiments thereof. In embodiments, the compound is MPA-3. In embodiments, the compound is MPA-2/RCGD 423N. In embodiments, the compound is MPA-1/RCGD 423F. In embodiments, the compound is MPA-4/RCGD 423/RCGD 423B. In embodiments, the method is performed in vitro. In embodiments, the HFSC is in a subject in need thereof, wherein the method includes administering to the subject an effective amount of the compound. In embodiments, the activating results in an increase in lactate dehydrogenase activity (e.g. an activity the results in hair growth) relative to the absence of the compound.

In embodiments, the HFSC is a human HFSC. In embodiments, the HFSC is within a human subject. In embodiments, the HFSC is a quiescent HFSC.

Further to any aspect disclosed herein contemplating a HFSC, and embodiment thereof, in further embodiments the HFSC forms part of an organism, e.g., a mammal. In embodiments, the organism is a human.

In embodiments, the compound is a compound described herein (e.g., in an aspect, embodiment, example, table, figure, scheme, appendix, or claim).

In embodiments of the methods provided herein, the subject is a human subject. In embodiments, the subject is a male human subject. In embodiments, the subject is a female human subject. The human subject may be suffering from hair loss. The hair loss may be due to family history (heredity or genetics), harmonal changes, a medical condition (e.g. dissecting cellulitis, a fungal infection (such as tinea capitis), folliculitis, secondary syphilis, demodex folliculorum), a medication or a medical treatment. In embodiments, the hair loss is due to androgenic hair loss, alopecia androgenetica, or alopecia seborrheica. In embodiments, the hair loss is due to traction alopecia, trichotillomania, childbirth, major surgery, poisoning, or severe stress (e.g. telogen effluvium). In embodiments, the hair loss is due to alopecia mucinosa, biotinidase deficiency, chronic inflammation, diabetes, lupus erythematosus, pseudopelade of Brocq, telogen effluvium or tufted folliculitis.

In embodiments, the subject is a domesticated animal, such as a dog, cat or horse. In embodiments, the subject is a cat. In embodiments, the subject is horse.

II. Pharmaceutical Compositions

Also provided herein are pharmaceutical formulations. In one aspect is a pharmaceutical composition that includes a compound described herein and a pharmaceutically acceptable excipient, the pharmaceutical composition useful in the practice of the methods disclosed herein.

In embodiments of the pharmaceutical compositions, the compound, or pharmaceutically acceptable salt thereof, is included in a therapeutically effective amount.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between LD$_{50}$ (the amount of compound lethal in 50% of the population) and ED$_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the ED$_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

III. Embodiments

Embodiment P1

A method for hair growth, said method comprising administering to a subject in need thereof an effective amount of a compound with structure of Formula (III):

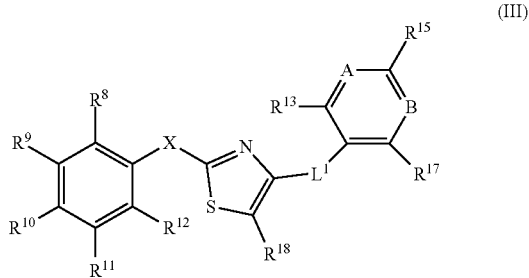

(III)

or a pharmaceutically acceptable salt thereof,
wherein:
A is CR$^{14}$ or N;
B is CR$^{16}$ or N;
X is O, NR$^9$ or S;
L$^1$ is a bond or substituted or unsubstituted C$_1$-C$_3$ alkylene;
n1 is an integer from 0 to 4;
m1 and v1 are independently 1 or 2;
R$^8$ is hydrogen, halogen, —CX$^{8.1}{}_3$, —CHX$^{8.1}{}_2$, —CH$_2$X$^{8.1}$, —CN, —SO$_{n1}$R$^{8A}$, —SO$_{v1}$NR$^{8B}$R$^{8C}$, —NHNR$^{8B}$R$^{8C}$, —ONR$^{8B}$R$^{8C}$, —NHC(O)NHNR$^{8B}$R$^{8C}$, —NHC(O)NR$^{8B}$R$^{8C}$, —N(O)$_{m1}$, —NR$^{8B}$R$^{8C}$, —C(O)R$^{8D}$, —C(O)OR$^{8D}$, —C(O)NR$^{8B}$R$^{8C}$, —OR$^{8A}$, —NR$^{8B}$SO$_2$R$^{8A}$, —NR$^{8B}$C(O)R$^{8D}$, —NR$^{8B}$C(O)OR$^{8D}$, —NR$^{8B}$OR$^{8D}$, —OCX$^{8.1}{}_3$, —OCHX$^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^{9.1}{}_3$, —CHX$^{9.1}{}_2$, —CH$_2$X$^{9.1}$, —CN, —SO$_{n1}$R$^{9A}$, —SO$_{v1}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}{}_3$, —OCHX$^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10.1}{}_3$, —CHX$^{10.1}{}_2$, —CH$_2$X$^{10.1}$, —CN, —SO$_{n1}$R$^{11A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m1}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}{}_3$, —OCHX$^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11.13}$, —CHX$^{11.1}{}_2$, —CH$_2$X$^{11.1}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}{}_3$, —OCHX$^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12.1}{}_3$, —CHX$^{12.1}{}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}{}_3$, —OCHX$^{12.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —CX$^{13.1}{}_3$, —CHX$^{13.1}{}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}{}_3$, —OCHX$^{13.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, —$CX^{14.1}_3$, —$CHX^{14.1}_2$, —$CH_2X^{14.1}$, —CN, —$SO_{n1}R^{14A}$, —$SO_{v1}NR^{14B}R^{14C}$, —$NHNR^{14B}R^{14C}$, —$ONR^{14B}R^{14C}$, —NHC(O)NHNR^{14B}R^{14C}$, —$NHC(O)NR^{14B}R^{14C}$, —$N(O)_{m1}$, —$NR^{14B}R^{14C}$, —$C(O)R^{14D}$, —$C(O)OR^{14D}$, —C(O)NR^{14B}R^{14C}$, —$OR^{14A}$, —$NR^{14B}SO_2R^{14A}$, —$NR^{14B}C(O)R^{14D}$, —$NR^{14B}C(O)OR^{14D}$, —$NR^{14B}OR^{14D}$, —$OCX^{14.1}_3$, —$OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —$CX^{15.1}_3$, —$CHX^{15.1}_2$, —$CH_2X^{15.1}$, —CN, —$SO_{n1}R^{15A}$, —$SO_{v1}NR^{15B}R^{15C}$, —$NHNR^{15B}R^{15C}$, —$ONR^{15B}R^{15C}$, —NHC(O)NHNR^{15B}R^{15C}$, —$NHC(O)NR^{15B}R^{15C}$, —$N(O)_{m1}$, —$NR^{15B}R^{15C}$, —$C(O)R^{15D}$, —$C(O)OR^{15D}$, —C(O)NR^{15B}R^{15C}$, —$OR^{15A}$, —$NR^{15B}SO_2R^{15A}$, —$NR^{15B}C(O)R^{15D}$, —$NR^{15B}C(O)OR^{15D}$, —$NR^{15B}OR^{15D}$, —$OCX^{15.1}_3$, —$OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$CX^{16.1}_3$, —$CHX^{16.1}_2$, —$CH_2X^{16.1}$, —CN, —$SO_{n1}R^{16A}$, —$SO_{v1}NR^{16B}R^{16C}$, —$NHNR^{16B}R^{16C}$, —$ONR^{16B}R^{16C}$, —NHC(O)NHNR^{16B}R^{16C}$, —$NHC(O)NR^{16B}R^{16C}$, —$N(O)_{m1}$, —$NR^{16B}R^{16C}$, —$C(O)R^{16D}$, —$C(O)OR^{16D}$, —C(O)NR^{16B}R^{16C}$, —$OR^{16A}$, —$NR^{16B}SO_2R^{16A}$, —$NR^{16B}C(O)R^{16D}$, —$NR^{16B}C(O)OR^{16D}$, —$NR^{16B}OR^{16D}$, —$OCX^{16.1}_3$, —$OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —$CX^{17.1}_3$, —$CHX^{17.1}_2$, —$CH_2X^{17.1}$, —CN, —$SO_{n1}R^{17A}$, —$SO_{v1}NR^{17B}R^{17C}$, —$NHNR^{17B}R^{17C}$, —$ONR^{7B}R^{17C}$, —NHC(O)NHNR^{17B}R^{17C}$, —$NHC(O)NR^{17B}R^{17C}$, —$N(O)_{m1}$, —$NR^{17B}R^{17C}$, —$C(O)R^{17D}$, —$C(O)OR^{17D}$, —C(O)NR^{17B}R^{17C}$, —$OR^{17A}$, —$NR^{17B}SO_2R^{17A}$, —$NR^{17B}C(O)R^{17D}$, —$NR^{17B}C(O)OR^{17D}$, —$NR^{17B}OR^{17D}$, —$OCX^{17.1}_3$, —$OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$CX^{18.1}_3$, —$CHX^{18.1}_2$, —$CH_2X^{18.1}$, —CN, —$SO_{n1}R^{18A}$, —$SO_{v1}NR^{18B}R^{18C}$, —$NHNR^{18B}R^{18C}$, —$ONR^{8B}R^{8C}$, —NHC(O)NHNR^{18B}R^{18C}$, —$NHC(O)NR^{18B}R^{18C}$, —$N(O)_{m1}$, —$NR^{18B}R^{18C}$, —$C(O)R^{18D}$, —$C(O)OR^{18D}$, —C(O)NR^{18B}R^{18C}$, —$OR^{18A}$, —$NR^{18B}SO_2R^{18A}$, —$NR^{18B}C(O)R^{18D}$, —$NR^{18B}C(O)OR^{18D}$, —$NR^{18}OR^{18D}$, —$OCX^{18.1}_3$, —$OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19}$ is hydrogen, —$COR^{19D}$, —$C(O)NHNR^{19B}R^{19C}$, —$C(O)OR^{19D}$, —$SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$ and $R^{18D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$ and $X^{18.1}$ are independently —Cl, —Br, —I or —F.

Embodiment P2

The method according to embodiment P1, wherein L is a bond and X is NH.

Embodiment P3

The method according to embodiment P2, wherein $R^{13}$, $R^5$, $R^{17}$ and $R^{18}$ are independently hydrogen.

Embodiment P4

The method according to embodiment P3, wherein $R^8$, $R^9$, $R^{11}$ and $R^{12}$ are independently hydrogen.

Embodiment P5

The method according to embodiment P4, wherein: A is $CR^{14}$; and B is $CR^{16}$.

Embodiment P6

The method according to embodiment P5, wherein:
$R^{10}$ is hydrogen, fluorine, chlorine, iodine, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —NHC(O)NHNR$^{10B}R^{10C}$, —$NHC(O)NR^{10B}R^{10C}$, —$N(O)_{m1}$, —$NR^{10B}R^{15C}$, —$C(O)R^{10D}$, —$C(O)OR^{10D}$, —C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{14}$ and $R^{16}$ are independently hydrogen.

Embodiment P7

The method according to embodiment P6, wherein $R^{10}$ is fluorine, chlorine or iodine.

Embodiment P8

The method according to embodiment P2, wherein $R^8$, $R^9$, $R^{11}$, $R^{12}$, $R^{13}$, $R^{15}$, $R^{17}$ and $R^{18}$ are independently hydrogen.

Embodiment P9

The method according to embodiment P8, wherein:
A is N;
B is $CR^{16}$; and
$R^{16}$ is hydrogen.

Embodiment P10

The method according to embodiment P9, wherein $R^{10}$ is fluorine, chlorine, bromine or iodine.

Embodiment P11

The method according to embodiment P8, wherein:
A and B are independently N; and
$R^{10}$ is fluorine, chlorine, bromine or iodine.

Embodiment P12

The method according to embodiment P1, wherein the compound with structure of Formula (III) has the structure of Formula (IIIa):

(IIIa)

or a pharmaceutically acceptable salt thereof, wherein:
$R^{10}$ is hydrogen, fluorine, chlorine or iodine, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment P13

The method according to embodiment P1, wherein the compound with structure of Formula (III) has the structure of Formula (IIIb):

(IIIb)

or a pharmaceutically acceptable salt thereof.

Embodiment P14

The method according to embodiment P1, wherein the compound with structure of Formula (III) has the structure of Formula (IIIc):

(IIIc)

or a pharmaceutically acceptable salt thereof.

Embodiment P15

A method for hair regeneration, said method comprising administering to a subject in need thereof an effective amount of a compound with structure of Formula (III), (IIIa), (IIIb) or (IIIc) as set forth in one of embodiments P1 to P14.

Embodiment P16

A method for activating a quiescent hair follicle stem cell (HFSC), said method comprising contacting a quiescent HFSC with an effective amount of a compound with structure of Formula (III), (IIIa), (IIIb) or (IIIc) as set forth in one of embodiments P1 to P14, thereby activating said quiescent HFSC.

Embodiment P17

The method according to embodiment P16, wherein said quiescent HFSC is a human HFSC.

Embodiment P18

The method according to embodiment P17, wherein said quiescent HFSC is within a human subject.

Embodiment P19

A method for increasing glycolysis in a hair follicle stem cell (HFSC), said method comprising contacting a HFSC with an effective amount of a compound with structure of Formula (III), (IIIa), (IIIb) or (IIIc) as set forth in one of embodiments P1 to P14.

83

Embodiment P20

The method according to embodiment P19, wherein said HFSC is a human HFSC.

Embodiment P21

The method according to embodiment P20, wherein said HFSC is within a human subject.

Embodiment P22

The method according to any one of embodiments P19 to P21, wherein said HFSC is a quiescent HFSC.

Embodiment P23

The method according to any one of embodiments P19 to P22, wherein levels of glycolytic metabolites are increased relative to the absence of administration of said compound.

Embodiment P24

The method according to embodiment P23, wherein said glycolytic metabolites are glucose, fructose-6-phosphate, fructose-bisphosphate, dihydroxyacetone phosphate, 3-phosphoglycerate or lactate.

Embodiment P25

A method for activation of lactate dehydrogenase in a hair follicle stem cell (HFSC), said method comprising contacting a HFSC with an effective amount of a compound with structure of Formula (III), (IIIa), (IIIb) or (IIIc) as set forth in one of embodiments P1 to P14.

Embodiment P26

The method according to embodiment P25, said HFSC is a human HFSC.

Embodiment P27

The method according to embodiment P26, said HFSC is within a human subject.

Embodiment P28

The method according to any one of embodiments P25 to P27, wherein said HFSC is a quiescent HFSC.

IV. Additional Embodiments

Embodiment 1

A method for inducing hair growth in a subject in need thereof, said method comprising administering to said subject an effective amount of a compound with structure of Formula (III):

84

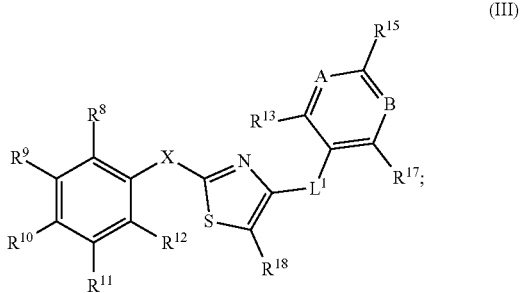

(III)

or a pharmaceutically acceptable salt thereof, wherein:

A is $CR^{14}$ or N;

B is $CR^{16}$ or N;

X is O, $NR^{19}$ or S;

$L^1$ is a bond or substituted or unsubstituted $C_1$-$C_3$ alkylene;

n1 is an integer from 0 to 4;

m1 and v1 are independently 1 or 2;

$R^8$ is hydrogen, halogen, $-CX^{8.1}{}_3$, $-CHX^{8.1}{}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}{}_3$, $-CHX^{9.1}{}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^{9.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10.1}{}_3$, $-CHX^{10.1}{}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11.13}$, $-CHX^{11.1}{}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}{}_3$, $-OCHX^{11.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-NR^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-NR^{16B}C(O)R^{16D}$, $-N^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-NR^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$, and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently $-Cl$, $-Br$, $-I$ or $-F$.

Embodiment 2

The method according to embodiment 1, wherein $L^1$ is a bond and X is NH.

Embodiment 3

The method according to embodiment 2, wherein $R^{13}$, $R^{15}$, $R^{17}$ and $R^{18}$ are independently hydrogen.

Embodiment 4

The method according to embodiment 3, wherein $R^8$, $R^9$, $R^{11}$ and $R^{12}$ are independently hydrogen.

Embodiment 5

The method according to embodiment 4, wherein: A is $CR^{14}$; and B is $CR^{16}$.

Embodiment 6

The method according to embodiment 5, wherein:

$R^{10}$ is hydrogen, fluorine, chlorine, iodine, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{11D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{14}$ and $R^{16}$ are independently hydrogen.

Embodiment 7

The method according to embodiment 6, wherein $R^{10}$ is fluorine, chlorine or iodine.

Embodiment 8

The method according to embodiment 2, wherein $R^8$, $R^9$, $R^{11}$, $R^{12}$, $R^{13}$, $R^{15}$, $R^{17}$ and $R^{18}$ are independently hydrogen.

Embodiment 9

The method according to embodiment 8, wherein:

A is N;

B is $CR^{16}$; and $R^{16}$ is hydrogen.

Embodiment 10

The method according to embodiment 9, wherein $R^{10}$ is fluorine, chlorine, bromine or iodine.

Embodiment 11

The method according to embodiment 8, wherein:

A and B are independently N; and $R^{10}$ is fluorine, chlorine, bromine or iodine.

Embodiment 12

The method according to embodiment 1, wherein the compound has the structure of Formula (IIIa):

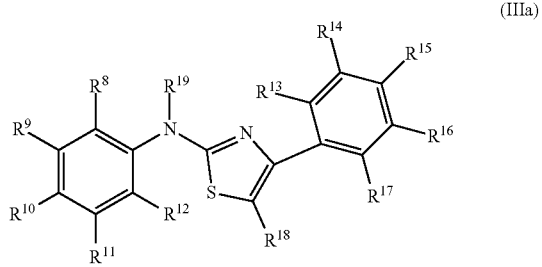

(IIIa)

or a pharmaceutically acceptable salt thereof, wherein:

$R^{10}$ is hydrogen, fluorine, chlorine or iodine, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 13

The method according to embodiment 1, wherein the compound has the structure of Formula (IIIb):

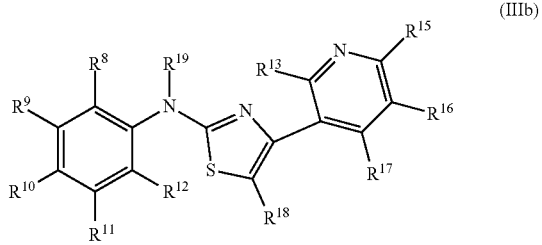

(IIIb)

or a pharmaceutically acceptable salt thereof.

Embodiment 14

The method according to embodiment 1, wherein the compound has the structure of Formula (IIIc):

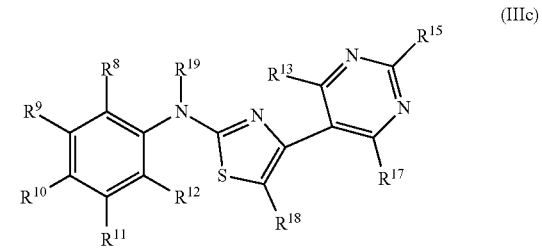

(IIIc)

or a pharmaceutically acceptable salt thereof.

Embodiment 15

A method for inducing hair regeneration in a subject in need thereof, said method comprising administering to said subject an effective amount of a compound with structure of Formula (III):

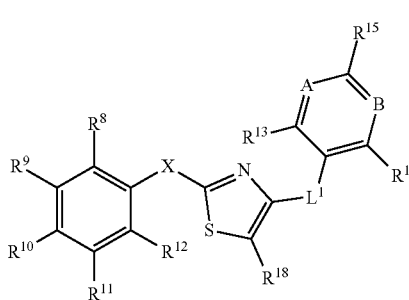

(III)

or a pharmaceutically acceptable salt thereof,
wherein:
A is $CR^{14}$ or N;
B is $CR^{16}$ or N;
X is O, $NR^{19}$ or S;
$L^1$ is a bond or substituted or unsubstituted $C_1$-$C_3$ alkylene;
n1 is an integer from 0 to 4;
m1 and v1 are independently 1 or 2;
$R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10}$ is hydrogen, halogen, $-CX^{10.1}_3$, $-CHX^{10.1}_2$, $-CH_2X^{10.1}$, $-CN$, $-SO_{n1}R^{1A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O) NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O) NR^{11B}R^{11C}$, $-OR^{11A}$, $-NR^{11B}SO_2R^{11A}$, $-NR^{11B}C(O) R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O) NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O) NR^{12B}R^{12C}$, $-OR^{12A}$, $-NR^{12B}SO_2R^{12A}$, $-NR^{12B}C(O) R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O) NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O) NR^{13B}R^{13C}$, $-OR^{13A}$, $-NR^{13B}SO_2R^{13A}$, $-NR^{13B}C(O) R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O) NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O) NR^{14B}R^{14C}$, $-OR^{14A}$, $-NR^{14B}SO_2R^{14A}$, $-NR^{14B}C(O) R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O) NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O) NR^{15B}R^{15C}$, $-OR^{15A}$, $-NR^{15B}SO_2R^{15A}$, $-NR^{15B}C(O) R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O) NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O) NR^{16B}R^{16C}$, $-OR^{16A}$, $-NR^{16B}SO_2R^{16A}$, $-NR^{16B}C(O) R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —$CX^{17.1}_3$, —$CHX^{17.1}_2$, —$CH_2X^{17.1}$, —CN, —$SO_{n1}R^{17A}$, —$SO_{v1}NR^{17B}R^{17C}$, —$NHNR^{17B}R^{17C}$, —$ONR^{17B}R^{17C}$, —NHC(O)$NHNR^{17B}R^{17C}$, —NHC(O)$NR^{17B}R^{17C}$, —N(O)$_{m1}$, —$NR^{17B}R^{17C}$, —C(O)$R^{17D}$, —C(O)O$R^{17D}$, —C(O)$NR^{17B}R^{17C}$, —O$R^{17A}$, —$NR^{17B}SO_2R^{17A}$, —$NR^{17B}C(O)R^{17D}$, —$NR^{17B}C(O)OR^{17D}$, —$NR^{17B}OR^{17D}$, —$OCX^{17.1}_3$, —$OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —$CX^{18.1}_3$, —$CHX^{18.1}_2$, —$CH_2X^{18.1}$, —CN, —$SO_{n1}R^{18A}$, —$SO_{v1}NR^{18B}R^{18C}$, —$NHNR^{18B}R^{18C}$, —$ONR^{18B}R^{18C}$, —NHC(O)$NHNR^{18B}R^{18C}$, —NHC(O)$NR^{18B}R^{18C}$, —N(O)$_{m1}$, —$NR^{18B}R^{18C}$, —C(O)$R^{18D}$, —C(O)O$R^{18D}$, —C(O)$NR^{18B}R^{18C}$, —O$R^{18A}$, —$NR^{18B}SO_2R^{18A}$, —$NR^{18B}C(O)R^{18D}$, —$NR^{18B}C(O)OR^{18D}$, —$NR^{18B}OR^{18D}$, —$OCX^{18.1}_3$, —$OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19}$ is hydrogen, —$COR^{19D}$, —C(O)$NHNR^{19B}R^{19C}$, —C(O)O$R^{19D}$, —$SO_2R^{19A}$, C(O)$NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$ and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently —Cl, —Br, —I or —F.

Embodiment 16

A method for activating a quiescent hair follicle stem cell (HFSC) in a subject in need thereof, said method comprising contacting a quiescent HFSC with an effective amount of a compound with structure of Formula (III):

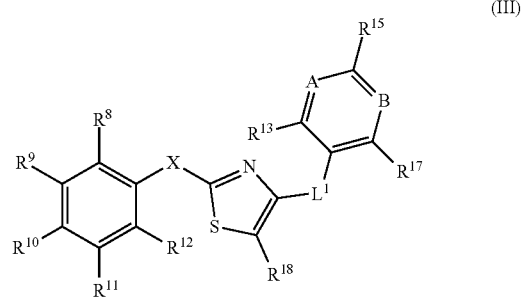

(III)

or a pharmaceutically acceptable salt thereof, wherein:

A is $CR^{14}$ or N;

B is $CR^{16}$ or N;

X is O, $NR^{19}$ or S;

$L^1$ is a bond or substituted or unsubstituted $C_1$-$C_3$ alkylene;

n1 is an integer from 0 to 4;

m1 and v1 are independently 1 or 2;

$R^8$ is hydrogen, halogen, —$CX^{8.1}_3$, —$CHX^{8.1}_2$, —$CH_2X^{8.1}$, —CN, —$SO_{n1}R^{8A}$, —$SO_{v1}NR^{8B}R^{8C}$, —$NHNR^{8B}R^{8C}$, —$ONR^{8B}R^{8C}$, —NHC(O)$NHNR^{8B}R^{8C}$, —NHC(O)$NR^{8B}R^{8C}$, —N(O)$_{m1}$, —$NR^{8B}R^{8C}$, —C(O)$R^{8D}$, —C(O)O$R^{8D}$, —C(O)$NR^{8B}R^{8C}$, —O$R^{8A}$, —$NR^{8B}SO_2R^{8A}$, —$NR^{8B}C(O)R^{8D}$, —$NR^{8B}C(O)OR^{8D}$, —$NR^{8B}OR^{8D}$, —$OCX^{8.1}_3$, —$OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^{9.1}_3$, —$CHX^{9.1}_2$, —$CH_2X^{9.1}$, —CN, —$SO_{n1}R^{9A}$, —$SO_{v1}NR^{9B}R^{9C}$, —$NHNR^{9B}R^{9C}$, —$ONR^{9B}R^{9C}$, —NHC(O)$NHNR^{9B}R^{9C}$, —NHC(O)$NR^{9B}R^{9C}$, —N(O)$_{m1}$, —$NR^{9B}R^{9C}$, —C(O)$R^{9D}$, —C(O)O$R^{9D}$, —C(O)$NR^{9B}R^{9C}$, —O$R^{9A}$, —$NR^{9B}SO_2R^{9A}$, —$NR^{9B}C(O)R^{9D}$, —$NR^{9B}C(O)OR^{9D}$, —$NR^{9B}OR^{9D}$, —$OCX^{9.1}_3$, —$OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —NHC(O)$NHNR^{10B}R^{10C}$, —NHC(O)$NR^{10B}R^{10C}$, —N(O)$_{m1}$, —$NR^{10B}R^{10C}$, —C(O)$R^{10D}$, —C(O)O$R^{10D}$, —C(O)$NR^{10B}R^{10C}$, —O$R^{10A}$, —$R^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —$CX^{11.1}_3$, —$CHX^{11.1}_2$, —$CH_2X^{11.1}$, —CN, —$SO_{n1}R^{11A}$, —$SO_{v1}NR^{11B}R^{11C}$, —$NHNR^{11B}R^{11C}$, —$NHNR^{11B}R^{11C}$, —$ONR^{11B}R^{11C}$, —NHC(O)$NHNR^{11B}R^{11C}$, —NHC(O)$NR^{11B}R^{11C}$, —N(O)$_{m1}$, —$NR^{11B}R^{11C}$, —C(O)$R^{11D}$, —C(O)O$R^{11D}$, —C(O)$NR^{11B}R^{11C}$, —O$R^{11A}$, —$NR^{11B}SO_2R^{11A}$, —$NR^{11B}C(O)R^{11D}$, —$NR^{11B}C(O)OR^{11D}$, —$NR^{11B}OR^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —NHNR$^{3B}$R$^{13C}$, —ONR$^{3B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{14}$ is hydrogen, halogen, —CX$^{14.1}_3$, —CHX$^{14.1}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}_3$, —OCHX$^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{1D}$, —OCX$^{15.1}_3$, —OCHX$^{51.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —CX$^{16.1}_3$, —CHX$^{16.1}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17c}$, $R^{18B}$, $R^{18C}$, $R^{19B}$ and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently —Cl, —Br, —I or —F.

Embodiment 17

The method according to embodiment 16, wherein said quiescent HFSC is a human HFSC.

Embodiment 18

The method according to embodiment 17, wherein said quiescent HFSC is within a human subject.

Embodiment 19

A method for inducing glycolysis in a hair follicle stem cell (HFSC), said method comprising contacting a HFSC with an effective amount of a compound with structure of Formula (III):

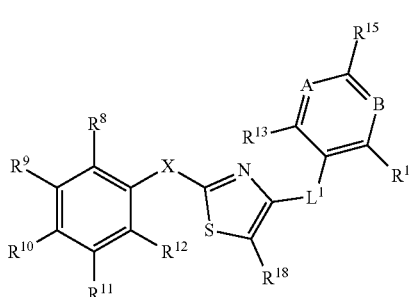

(III)

or a pharmaceutically acceptable salt thereof,
wherein:
A is $CR^{14}$ or N;
B is $CR^{16}$ or N;
X is O, $NR^{19}$ or S;
$L^1$ is a bond or substituted or unsubstituted $C_1$-$C_3$ alkylene;
n1 is an integer from 0 to 4;
m1 and v1 are independently 1 or 2;
$R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m1}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{10}$ is hydrogen, halogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{11B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{11}$ is hydrogen, halogen, $-CX^{11.1}_3$, $-CHX^{11.1}_2$, $-CH_2X^{11.1}$, $-CN$, $-SO_{n1}R^{11A}$, $-SO_{v1}NR^{11B}R^{11C}$, $-NHNR^{11B}R^{11C}$, $-ONR^{11B}R^{11C}$, $-NHC(O)NHNR^{11B}R^{11C}$, $-NHC(O)NR^{11B}R^{11C}$, $-N(O)_{m1}$, $-NR^{11B}R^{11C}$, $-C(O)R^{11D}$, $-C(O)OR^{11D}$, $-C(O)NR^{11B}R^{11C}$, $-OR^{11A}$, $-NR^{11B}SO_2R^{11A}$, $-NR^{11B}C(O)R^{11D}$, $-NR^{11B}C(O)OR^{11D}$, $-NR^{11B}OR^{11D}$, $-OCX^{11.1}_3$, $-OCHX^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{12}$ is hydrogen, halogen, $-CX^{12.1}_3$, $-CHX^{12.1}_2$, $-CH_2X^{12.1}$, $-CN$, $-SO_{n1}R^{12A}$, $-SO_{v1}NR^{12B}R^{12C}$, $-NHNR^{12B}R^{12C}$, $-ONR^{12B}R^{12C}$, $-NHC(O)NHNR^{12B}R^{12C}$, $-NHC(O)NR^{12B}R^{12C}$, $-N(O)_{m1}$, $-NR^{12B}R^{12C}$, $-C(O)R^{12D}$, $-C(O)OR^{12D}$, $-C(O)NR^{12B}R^{12C}$, $-OR^{12A}$, $-R^{12B}SO_2R^{12A}$, $-NR^{12B}C(O)R^{12D}$, $-NR^{12B}C(O)OR^{12D}$, $-NR^{12B}OR^{12D}$, $-OCX^{12.1}_3$, $-OCHX^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{13}$ is hydrogen, halogen, $-CX^{13.1}_3$, $-CHX^{13.1}_2$, $-CH_2X^{13.1}$, $-CN$, $-SO_{n1}R^{13A}$, $-SO_{v1}NR^{13B}R^{13C}$, $-NHNR^{13B}R^{13C}$, $-ONR^{13B}R^{13C}$, $-NHC(O)NHNR^{13B}R^{13C}$, $-NHC(O)NR^{13B}R^{13C}$, $-N(O)_{m1}$, $-NR^{13B}R^{13C}$, $-C(O)R^{13D}$, $-C(O)OR^{13D}$, $-C(O)NR^{13B}R^{13C}$, $-OR^{13A}$, $-NR^{13B}SO_2R^{13A}$, $-NR^{13B}C(O)R^{13D}$, $-NR^{13B}C(O)OR^{13D}$, $-NR^{13B}OR^{13D}$, $-OCX^{13.1}_3$, $-OCHX^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{14}$ is hydrogen, halogen, $-CX^{14.1}_3$, $-CHX^{14.1}_2$, $-CH_2X^{14.1}$, $-CN$, $-SO_{n1}R^{14A}$, $-SO_{v1}NR^{14B}R^{14C}$, $-NHNR^{14B}R^{14C}$, $-ONR^{14B}R^{14C}$, $-NHC(O)NHNR^{14B}R^{14C}$, $-NHC(O)NR^{14B}R^{14C}$, $-N(O)_{m1}$, $-NR^{14B}R^{14C}$, $-C(O)R^{14D}$, $-C(O)OR^{14D}$, $-C(O)NR^{14B}R^{14C}$, $-OR^{14A}$, $-NR^{14B}SO_2R^{14A}$, $-NR^{14B}C(O)R^{14D}$, $-NR^{14B}C(O)OR^{14D}$, $-NR^{14B}OR^{14D}$, $-OCX^{14.1}_3$, $-OCHX^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{15}$ is hydrogen, halogen, $-CX^{15.1}_3$, $-CHX^{15.1}_2$, $-CH_2X^{15.1}$, $-CN$, $-SO_{n1}R^{15A}$, $-SO_{v1}NR^{15B}R^{15C}$, $-NHNR^{15B}R^{15C}$, $-ONR^{15B}R^{15C}$, $-NHC(O)NHNR^{15B}R^{15C}$, $-NHC(O)NR^{15B}R^{15C}$, $-N(O)_{m1}$, $-NR^{15B}R^{15C}$, $-C(O)R^{15D}$, $-C(O)OR^{15D}$, $-C(O)NR^{15B}R^{15C}$, $-OR^{15A}$, $-NR^{15B}SO_2R^{15A}$, $-NR^{15B}C(O)R^{15D}$, $-NR^{15B}C(O)OR^{15D}$, $-NR^{15B}OR^{15D}$, $-OCX^{15.1}_3$, $-OCHX^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{16}$ is hydrogen, halogen, $-CX^{16.1}_3$, $-CHX^{16.1}_2$, $-CH_2X^{16.1}$, $-CN$, $-SO_{n1}R^{16A}$, $-SO_{v1}NR^{16B}R^{16C}$, $-NHNR^{16B}R^{16C}$, $-ONR^{16B}R^{16C}$, $-NHC(O)NHNR^{16B}R^{16C}$, $-NHC(O)NR^{16B}R^{16C}$, $-N(O)_{m1}$, $-NR^{16B}R^{16C}$, $-C(O)R^{16D}$, $-C(O)OR^{16D}$, $-C(O)NR^{16B}R^{16C}$, $-OR^{16A}$, $-NR^{16B}SO_2R^{16A}$, $-N^{16B}C(O)R^{16D}$, $-NR^{16B}C(O)OR^{16D}$, $-NR^{16B}OR^{16D}$, $-OCX^{16.1}_3$, $-OCHX^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17.1}_3$, $-CHX^{17.1}_2$, $-CH_2X^{17.1}$, $-CN$, $-SO_{n1}R^{17A}$, $-SO_{v1}NR^{17B}R^{17C}$, $-NHNR^{17B}R^{17C}$, $-ONR^{17B}R^{17C}$, $-NHC(O)NHNR^{17B}R^{17C}$, $-NHC(O)NR^{17B}R^{17C}$, $-N(O)_{m1}$, $-NR^{17B}R^{17C}$, $-C(O)R^{17D}$, $-C(O)OR^{17D}$, $-C(O)NR^{17B}R^{17C}$, $-OR^{17A}$, $-R^{17B}SO_2R^{17A}$, $-NR^{17B}C(O)R^{17D}$, $-NR^{17B}C(O)OR^{17D}$, $-NR^{17B}OR^{17D}$, $-OCX^{17.1}_3$, $-OCHX^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{18}$ is hydrogen, halogen, $-CX^{18.1}_3$, $-CHX^{18.1}_2$, $-CH_2X^{18.1}$, $-CN$, $-SO_{n1}R^{18A}$, $-SO_{v1}NR^{18B}R^{18C}$, $-NHNR^{18B}R^{18C}$, $-ONR^{18B}R^{18C}$, $-NHC(O)NHNR^{18B}R^{18C}$, $-NHC(O)NR^{18B}R^{18C}$, $-N(O)_{m1}$, $-NR^{18B}R^{18C}$, $-C(O)R^{18D}$, $-C(O)OR^{18D}$, $-C(O)NR^{18B}R^{18C}$, $-OR^{18A}$, $-NR^{18B}SO_2R^{18A}$, $-NR^{18B}C(O)R^{18D}$, $-NR^{18B}C(O)OR^{18D}$, $-NR^{18B}OR^{18D}$, $-OCX^{18.1}_3$, $-OCHX^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{19}$ is hydrogen, $-COR^{19D}$, $-C(O)NHNR^{19B}R^{19C}$, $-C(O)OR^{19D}$, $-SO_2R^{19A}$, $C(O)NR^{19B}R^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{11D}$, $R^{11A}$, $R^{11B}$, $R^{11C}$, $R^{11D}$, $R^{12A}$, $R^{12B}$, $R^{12C}$, $R^{12D}$, $R^{13A}$, $R^{13B}$, $R^{13C}$, $R^{13D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$ and $R^{19D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{19B}$ and $R^{19C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{1.1}$, $X^{12.1}$, $X^{13.1}$, $X^{14.1}$, $X^{15.1}$, $X^{16.1}$, $X^{17.1}$, $X^{18.1}$, and $X^{19.1}$ are independently $-Cl$, $-Br$, $-I$ or $-F$.

Embodiment 20

The method according to embodiment 19, wherein said HFSC is a human HFSC.

Embodiment 21

The method according to embodiment 20, wherein said HFSC is within a human subject.

Embodiment 22

The method according to any one of embodiments 19 to 21, wherein said HFSC is a quiescent HFSC.

Embodiment 23

The method according to any one of embodiments 19 to 22, wherein levels of glycolytic metabolites in said cell are increased relative to the absence of administration of said compound.

Embodiment 24

The method according to embodiment 23, wherein said glycolytic metabolites are glucose, fructose-6-phosphate, fructose-bisphosphate, dihydroxyacetone phosphate, 3-phosphoglycerate or lactate.

Embodiment 25

A method for activating lactate dehydrogenase in a hair follicle stem cell (HFSC), said method comprising contacting a HFSC with an effective amount of a compound with structure of Formula (III):

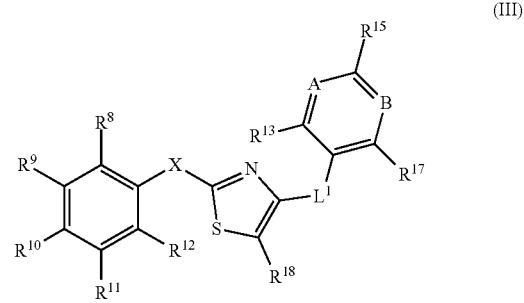

or a pharmaceutically acceptable salt thereof,
wherein:
A is $CR^{14}$ or N;
B is $CR^{16}$ or N;
X is O, $NR^{19}$ or S;
$L^1$ is a bond or substituted or unsubstituted $C_1$-$C_3$ alkylene;
n1 is an integer from 0 to 4;
m1 and v1 are independently 1 or 2;
$R^8$ is hydrogen, halogen, $-CX^{8.1}_3$, $-CHX^{8.1}_2$, $-CH_2X^{8.1}$, $-CN$, $-SO_{n1}R^{8A}$, $-SO_{v1}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m1}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^{9.1}_3$, $-CHX^{9.1}_2$, $-CH_2X^{9.1}$, $-CN$, $-SO_{n1}R^{9A}$, $-SO_{v1}NR^{9B}R^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m1}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{11.1}_3$, —CHX$^{10.1}_2$, —CH$_2$X$^{10.1}$, —CN, —SO$_{n1}$R$^{10A}$, —SO$_{v1}$NR$^{10B}$R$^{10C}$, —NHNR$^{10B}$R$^{10C}$, —ONR$^{10B}$R$^{10C}$, —NHC(O)NHNR$^{10B}$R$^{10C}$, —NHC(O)NR$^{10B}$R$^{10C}$, —N(O)$_{m1}$, —NR$^{10B}$R$^{10C}$, —C(O)R$^{10D}$, —C(O)OR$^{10D}$, —C(O)NR$^{10B}$R$^{10C}$, —OR$^{10A}$, —NR$^{10B}$SO$_2$R$^{10A}$, —NR$^{10B}$C(O)R$^{10D}$, —NR$^{10B}$C(O)OR$^{10D}$, —NR$^{10B}$OR$^{10D}$, —OCX$^{10.1}_3$, —OCHX$^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11.1}_3$, —CHX$^{11.1}_2$, —CH$_2$X$^{1.11}$, —CN, —SO$_{n1}$R$^{11A}$, —SO$_{v1}$NR$^{11B}$R$^{11C}$, —NHNR$^{11B}$R$^{11C}$, —ONR$^{11B}$R$^{11C}$, —NHC(O)NHNR$^{11B}$R$^{11C}$, —NHC(O)NR$^{11B}$R$^{11C}$, —N(O)$_{m1}$, —NR$^{11B}$R$^{11C}$, —C(O)R$^{11D}$, —C(O)OR$^{11D}$, —C(O)NR$^{11B}$R$^{11C}$, —OR$^{11A}$, —NR$^{11B}$SO$_2$R$^{11A}$, —NR$^{11B}$C(O)R$^{11D}$, —NR$^{11B}$C(O)OR$^{11D}$, —NR$^{11B}$OR$^{11D}$, —OCX$^{11.1}_3$, —OCHX$^{11.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12.1}_3$, —CHX$^{12.1}_2$, —CH$_2$X$^{12.1}$, —CN, —SO$_{n1}$R$^{12A}$, —SO$_{v1}$NR$^{12B}$R$^{12C}$, —NHNR$^{12B}$R$^{12C}$, —ONR$^{12B}$R$^{12C}$, —NHC(O)NHNR$^{12B}$R$^{12C}$, —NHC(O)NR$^{12B}$R$^{12C}$, —N(O)$_{m1}$, —NR$^{12B}$R$^{12C}$, —C(O)R$^{12D}$, —C(O)OR$^{12D}$, —C(O)NR$^{12B}$R$^{12C}$, —OR$^{12A}$, —NR$^{12B}$SO$_2$R$^{12A}$, —NR$^{12B}$C(O)R$^{12D}$, —NR$^{12B}$C(O)OR$^{12D}$, —NR$^{12B}$OR$^{12D}$, —OCX$^{12.1}_3$, —OCHX$^{12.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, halogen, —CX$^{13.1}_3$, —CHX$^{13.1}_2$, —CH$_2$X$^{13.1}$, —CN, —SO$_{n1}$R$^{13A}$, —SO$_{v1}$NR$^{13B}$R$^{13C}$, —NHNR$^{13B}$R$^{13C}$, —ONR$^{13B}$R$^{13C}$, —NHC(O)NHNR$^{13B}$R$^{13C}$, —NHC(O)NR$^{13B}$R$^{13C}$, —N(O)$_{m1}$, —NR$^{13B}$R$^{13C}$, —C(O)R$^{13D}$, —C(O)OR$^{13D}$, —C(O)NR$^{13B}$R$^{13C}$, —OR$^{13A}$, —NR$^{13B}$SO$_2$R$^{13A}$, —NR$^{13B}$C(O)R$^{13D}$, —NR$^{13B}$C(O)OR$^{13D}$, —NR$^{13B}$OR$^{13D}$, —OCX$^{13.1}_3$, —OCHX$^{13.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$ is hydrogen, halogen, —CX$^{14.1}_3$, —CHX$^{14.1}_2$, —CH$_2$X$^{14.1}$, —CN, —SO$_{n1}$R$^{14A}$, —SO$_{v1}$NR$^{14B}$R$^{14C}$, —NHNR$^{14B}$R$^{14C}$, —ONR$^{14B}$R$^{14C}$, —NHC(O)NHNR$^{14B}$R$^{14C}$, —NHC(O)NR$^{14B}$R$^{14C}$, —N(O)$_{m1}$, —NR$^{14B}$R$^{14C}$, —C(O)R$^{14D}$, —C(O)OR$^{14D}$, —C(O)NR$^{14B}$R$^{14C}$, —OR$^{14A}$, —NR$^{14B}$SO$_2$R$^{14A}$, —NR$^{14B}$C(O)R$^{14D}$, —NR$^{14B}$C(O)OR$^{14D}$, —NR$^{14B}$OR$^{14D}$, —OCX$^{14.1}_3$, —OCHX$^{14.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —CX$^{15.1}_3$, —CHX$^{15.1}_2$, —CH$_2$X$^{15.1}$, —CN, —SO$_{n1}$R$^{15A}$, —SO$_{v1}$NR$^{15B}$R$^{15C}$, —NHNR$^{15B}$R$^{15C}$, —ONR$^{15B}$R$^{15C}$, —NHC(O)NHNR$^{15B}$R$^{15C}$, —NHC(O)NR$^{15B}$R$^{15C}$, —N(O)$_{m1}$, —NR$^{15B}$R$^{15C}$, —C(O)R$^{15D}$, —C(O)OR$^{15D}$, —C(O)NR$^{15B}$R$^{15C}$, —OR$^{15A}$, —NR$^{15B}$SO$_2$R$^{15A}$, —NR$^{15B}$C(O)R$^{15D}$, —NR$^{15B}$C(O)OR$^{15D}$, —NR$^{15B}$OR$^{15D}$, —OCX$^{15.1}_3$, —OCHX$^{15.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —CX$^{16.1}_3$, —CHX$^{16.1}_2$, —CH$_2$X$^{16.1}$, —CN, —SO$_{n1}$R$^{16A}$, —SO$_{v1}$NR$^{16B}$R$^{16C}$, —NHNR$^{16B}$R$^{16C}$, —ONR$^{16B}$R$^{16C}$, —NHC(O)NHNR$^{16B}$R$^{16C}$, —NHC(O)NR$^{16B}$R$^{16C}$, —N(O)$_{m1}$, —NR$^{16B}$R$^{16C}$, —C(O)R$^{16D}$, —C(O)OR$^{16D}$, —C(O)NR$^{16B}$R$^{16C}$, —OR$^{16A}$, —NR$^{16B}$SO$_2$R$^{16A}$, —NR$^{16B}$C(O)R$^{16D}$, —NR$^{16B}$C(O)OR$^{16D}$, —NR$^{16B}$OR$^{16D}$, —OCX$^{16.1}_3$, —OCHX$^{16.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17.1}_3$, —CHX$^{17.1}_2$, —CH$_2$X$^{17.1}$, —CN, —SO$_{n1}$R$^{17A}$, —SO$_{v1}$NR$^{17B}$R$^{17C}$, —NHNR$^{17B}$R$^{17C}$, —ONR$^{17B}$R$^{17C}$, —NHC(O)NHNR$^{17B}$R$^{17C}$, —NHC(O)NR$^{17B}$R$^{17C}$, —N(O)$_{m1}$, —NR$^{17B}$R$^{17C}$, —C(O)R$^{17D}$, —C(O)OR$^{17D}$, —C(O)NR$^{17B}$R$^{17C}$, —OR$^{17A}$, —NR$^{17B}$SO$_2$R$^{17A}$, —NR$^{17B}$C(O)R$^{17D}$, —NR$^{17B}$C(O)OR$^{17D}$, —NR$^{17B}$OR$^{17D}$, —OCX$^{17.1}_3$, —OCHX$^{17.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{18}$ is hydrogen, halogen, —CX$^{18.1}_3$, —CHX$^{18.1}_2$, —CH$_2$X$^{18.1}$, —CN, —SO$_{n1}$R$^{18A}$, —SO$_{v1}$NR$^{18B}$R$^{18C}$, —NHNR$^{18B}$R$^{18C}$, —ONR$^{18B}$R$^{18C}$, —NHC(O)NHNR$^{18B}$R$^{18C}$, —NHC(O)NR$^{18B}$R$^{18C}$, —N(O)$_{m1}$, —NR$^{18B}$R$^{18C}$, —C(O)R$^{18D}$, —C(O)OR$^{18D}$, —C(O)NR$^{18B}$R$^{18C}$, —OR$^{18A}$, —NR$^{18B}$SO$_2$R$^{18A}$, —NR$^{18B}$C(O)R$^{18D}$, —NR$^{18B}$C(O)OR$^{18D}$, —NR$^{18B}$OR$^{18D}$, —OCX$^{18.1}_3$, —OCHX$^{18.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{19}$ is hydrogen, —COR$^{19D}$, —C(O)NHNR$^{19B}$R$^{19C}$, —C(O)OR$^{19D}$, —SO$_2$R$^{19A}$, C(O)NR$^{19B}$R$^{19C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$, R$^{12D}$, R$^{13A}$, R$^{13B}$, R$^{13C}$, R$^{13D}$, R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17B}$, R$^{17C}$, R$^{17D}$, R$^{18A}$, R$^{18B}$, R$^{18C}$, R$^{18D}$, R$^{19A}$, R$^{19B}$, R$^{19C}$ and R$^{19D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{11B}$, $R^{11C}$, $R^{12B}$, $R^{12C}$, $R^{13B}$, $R^{13C}$, $R^{14B}$, $R^{14C}$, $R^{15B}$, $R^{15C}$, $R^{16B}$, $R^{16C}$, $R^{17B}$, $R^{17C}$, $R^{18B}$, $R^{18C}$, $R^{18B'}$ and $R^{18C}$ substituents bonded to the same nitrogen atom may optionally be joined to form a substituted or unsubstituted heterocycloalkyl or substituted or unsubstituted heteroaryl; and $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, $X^{11.1}$, $X^{12.1}$, $X^{13.1}$, $X^{14.1}$, $X^{15.1}$, $X^{16.1}$, $X^{17.1}$, $X^{18.1}$, and $X^{19.1}$ are independently —Cl, —Br, —I or —F.

Embodiment 26

The method according to embodiment 25, said HFSC is a human HFSC.

Embodiment 27

The method according to embodiment 26, said HFSC is within a human subject.

Embodiment 28

The method according to any one of embodiments 25 to 27, wherein said HFSC is a quiescent HFSC.

V. Examples

Example 1. Lactate Production Drives Hair Follicle Stem Cell Activation

While normally dormant, Hair Follicle Stem Cells (HFSCs) quickly become activated to divide during a new hair cycle. The quiescence of HFSCs is known to be regulated by a number of intrinsic and extrinsic mechanisms. Here we provide several lines of evidence to demonstrate that HFSCs utilize glycolytic metabolism and produce significantly more lactate than other cells in the epidermis. Furthermore, without wishing to be bound by any theory, lactate generation appears to be critical for the activation of HFSCs as deletion of lactate dehydrogenase (Ldha) prevented their activation. Conversely, genetically promoting lactate production in HFSCs through mitochondrial pyruvate carrier (Mpc1) deletion accelerated their activation and the hair cycle. Finally, we identify small molecules that increase lactate production by stimulating Myc levels or inhibiting Mpc1 carrier activity and can topically induce the hair cycle. These data suggest that HFSCs maintain a metabolic state that allow them to remain dormant and yet quickly respond to appropriate proliferative stimuli.

The hair follicle is able to undergo cyclical rounds of rest (telogen), regeneration (anagen), and degeneration (catagen). The ability of the hair follicle to maintain this cycle depends on the presence of the hair follicle stem cells, which reside in the bulge (FIGS. 1A-1E). At the start of anagen, bulge stem cells are activated by signals received from the dermal papilla, which at that stage abuts the bulge area [1,2]. These stem cells exit the bulge and proliferate downwards, creating a trail that becomes the outer root sheath (ORS).

Bulge stem cells are capable of giving rise to all the different cell types of the hair follicle. The ability of HFSCs to maintain quiescence and yet become proliferative for a couple days before returning to quiescence is unique in this tissue, and the precise mechanism by which these cells are endowed with this ability is not fully understood. While significant effort has produced a wealth of knowledge on both the transcriptional and epigenetic mechanisms by which HFSCs are maintained and give rise to various lineages [3,4], little is known about metabolic pathways in the hair follicle or adult stem cells in vivo.

Considering the fact that there are essentially no published data on metabolic states of any cell in the hair follicle, a detailed study of metabolism was necessary to understand the nature of HFSCs and their progeny. Several previous studies employed genetic disruption of the mitochondrial electron transport chain in the epidermis by deletion under the control of a pan-epidermal keratin promoter and found that mitochondrial function was essential for maintenance of the follicle [8-11]. However, these studies did not explore the metabolic requirements for specific cell types within the tissue, nor did they explore a role for glycolytic metabolism. As disclosed herein, we present methods to study the metabolism of HFSCs in vivo, and provide evidence that these cells take advantage of a distinct mode of metabolism not found in their progeny. In the process, we also identify small molecules that can take advantage of the unique metabolism of HFSCs to ignite the hair cycle in otherwise quiescent follicles.

Figure 7A:
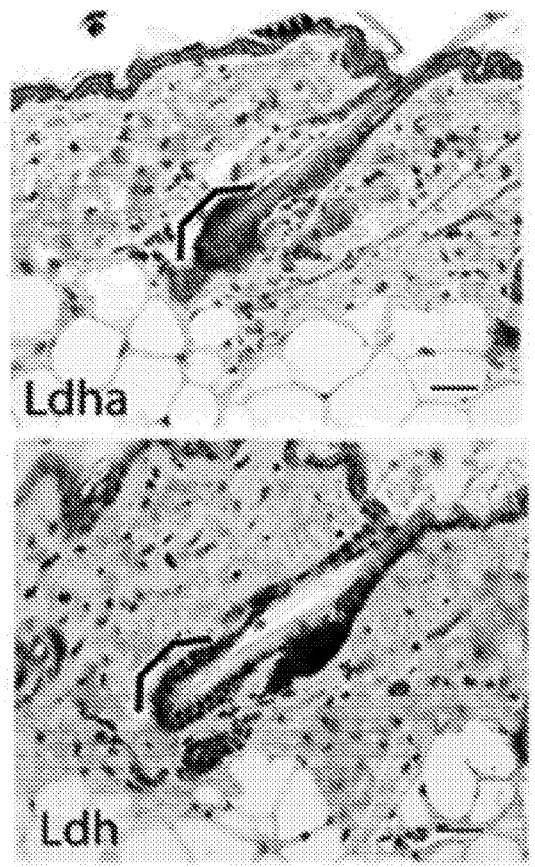
FIGS. 7A-7C. Validation of key reagents and assays.

Numerous studies have uncovered unique gene expression signatures in HFSCs versus other follicle cells or cells of the interfollicular epidermis [12-15]. Many of these signatures are regulated by transcription factors that were later shown to play important roles in HFSC homeostasis [16]. Lactate dehydrogenase is most commonly encoded by the Ldha and Ldhb genes in mammals, the protein products of which form homo- or hetero-tetramers to catalyze the NADH-dependent reduction of pyruvate to lactate and NAD$^+$-dependent oxidation of lactate to pyruvate[18]. By immunostaining, Ldha appeared to be enriched in quiescent HFSCs in situ (telogen) (FIG. 1A), IHC with an antibody that recognizes both Ldha and Ldhb showed that only Ldha appears to be localized to the HFSC niche (FIG. 7A).

Figure 7B:
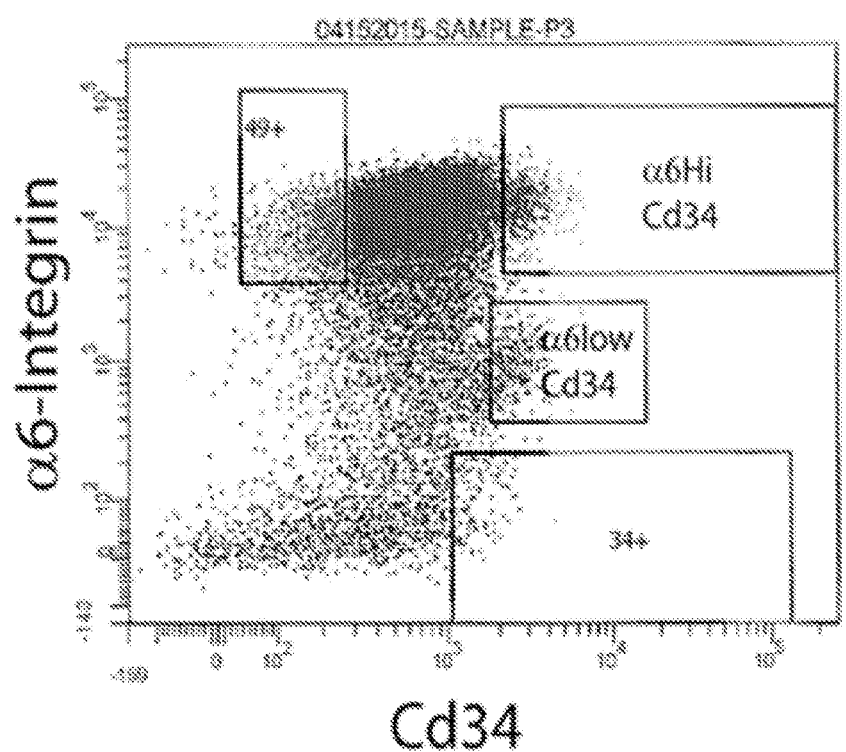

HFSCs are known to go through successive rounds of quiescence (telogen) punctuated by brief periods of proliferation correlating with the start of the hair cycle (telogen-anagen transition) [4,19]. Proliferation or activation of HFSCs is well known to be a prerequisite for advancement of the hair cycle. IHC analysis also showed Ldha expression was enriched in HFSCs (Sox9+) at three stages of the hair cycle (FIG. 1A). Consistently, immunoblotting of lysates from sorted cells showed strong expression of Ldha in the basal HFSCs (α6HiCD34+), and suprabasal (α6LoCD34+) HFSC populations relative to total epidermis (FIG. 1B) [12](Sorting strategy is outlined in FIG. 7B).

To determine whether Ldha expression patterns correlate with activity of the Ldh enzyme, we used a colorimetric-based enzymatic assay to assess Ldh activity capacity in situ. Typically performed on protein lysates or aliquots with a plate reader [20], we adapted the Ldh activity assay to work in situ on frozen tissue sections. Note that since both the in situ and in vitro Ldh activity assays employ use of excess substrate (lactate), the results from these assays reflect the capacity for Ldh activity, and not the steady-state activity.

Figure 1C:
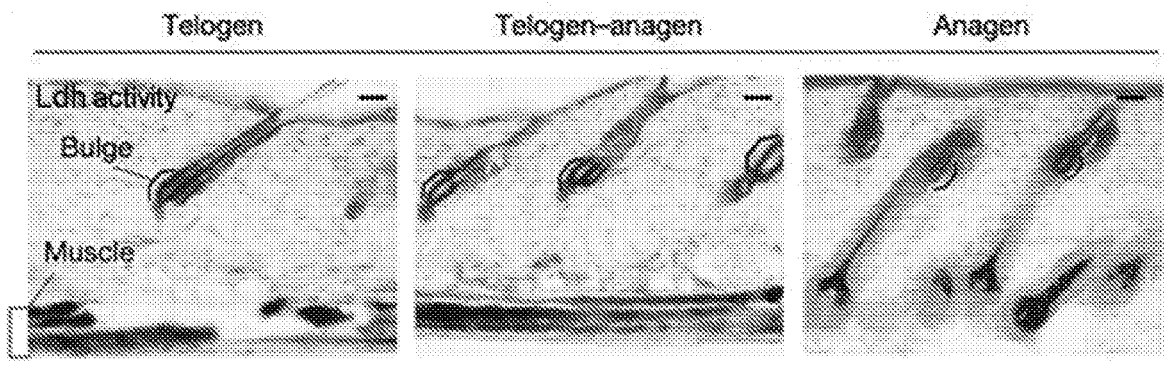

Applying this assay to skin samples demonstrated that Ldh activity capacity was significantly higher in HFSCs, consistent with the expression pattern of Ldha (FIG. 1C).

Figure 1D:
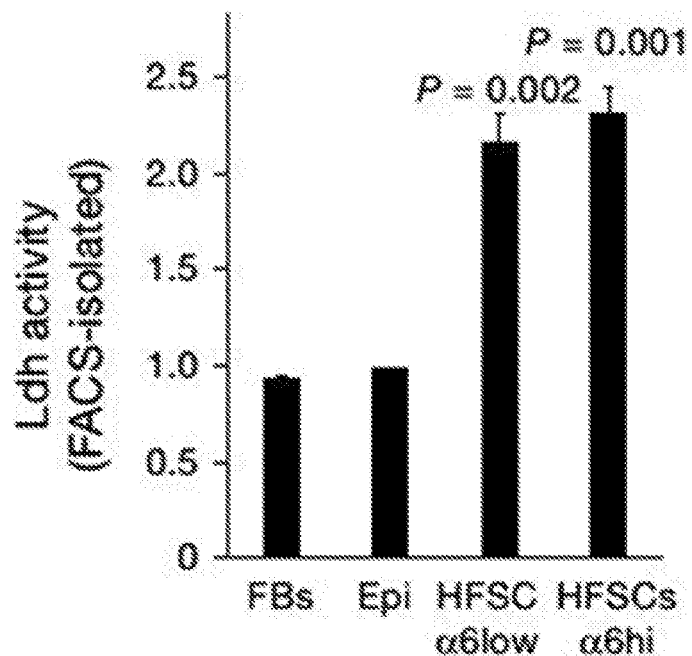
Figure 1E:
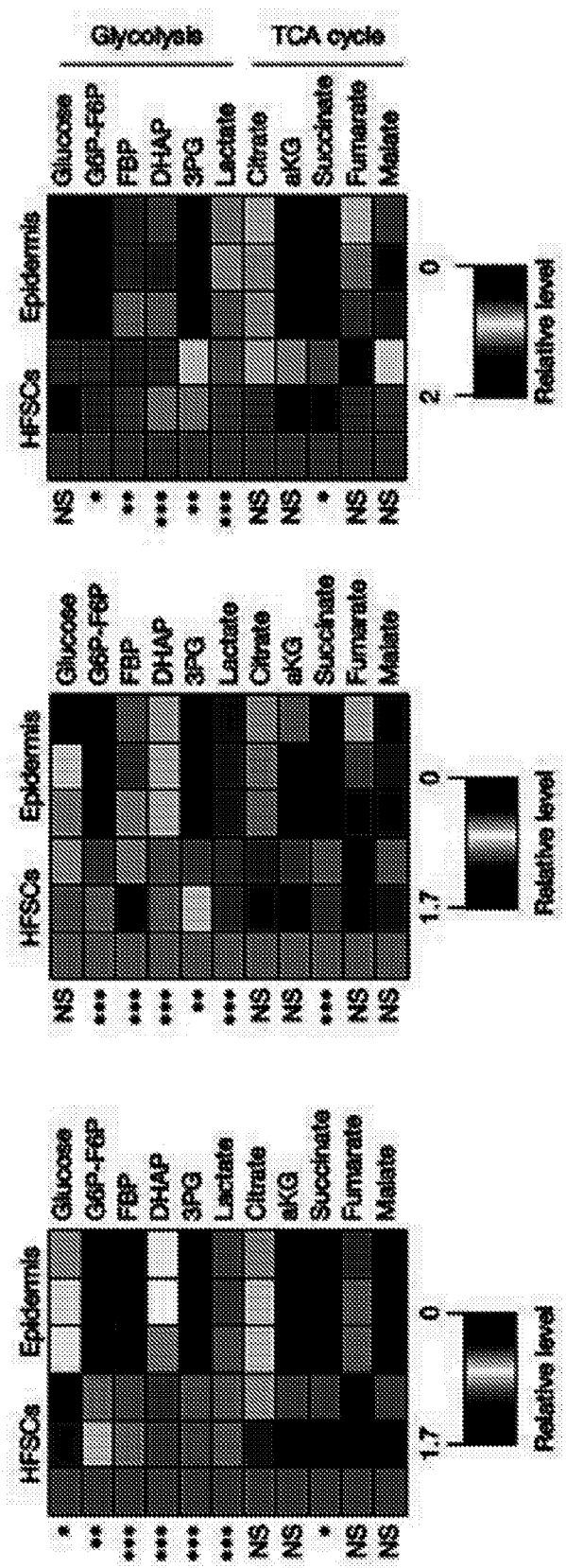
Figure 7C:
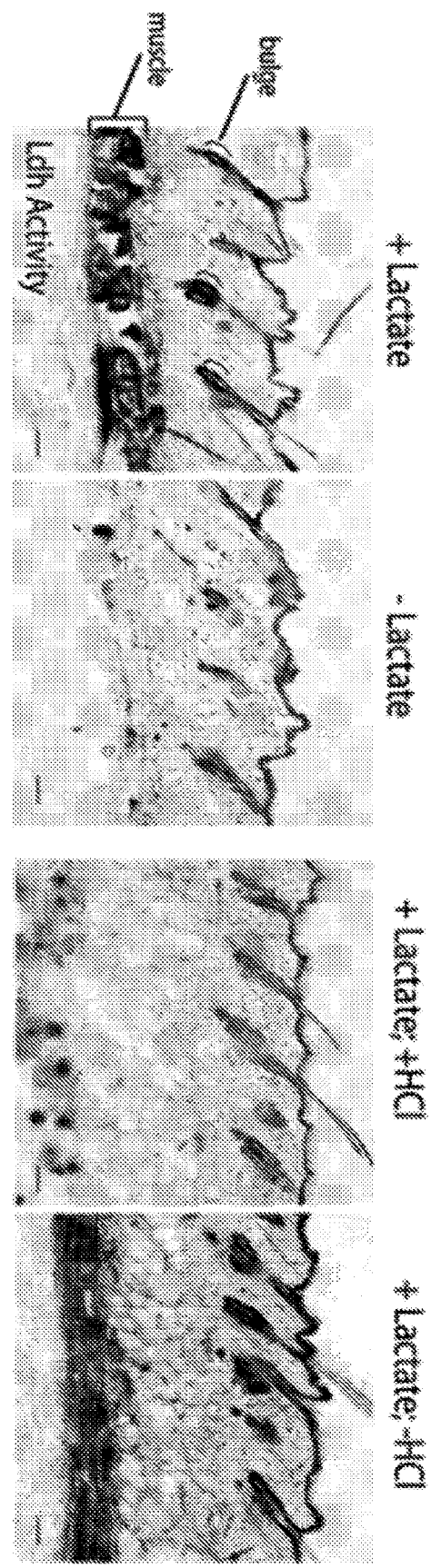

Furthermore, Ldh activity was enriched in HFSCs across the hair cycle (FIG. 1C). As a control, assays conducted without the enzymatic substrate (lactate) or on acid-treated tissue yielded zero activity (FIG. 7C). To further validate these results, we sorted epidermal populations, generated cell lysates on the sorted cells, and performed a similar colorimetric-based enzymatic assay on the sorted cell lysates, which also showed increased Ldh activity in HFSCs (FIG. 1D). To better characterize the metabolism of HFSCs, we performed metabolomics analysis on sorted populations from mouse skin by liquid chromatography-mass spectrometry (LC-MS) (FIG. 1E). Several glycolytic metabolites, including glucose/fructose-6-phosphate, fructose-bisphosphate, dihydroxyacetone phosphate, 3-phosphoglycerate, and lactate, were routinely higher in HFSCs relative to total epidermis across three independent experiments (isolated from different mice on different days). Conversely, most TCA cycle metabolites were not consistently different between the epidermis and HFSCs (FIG. 1E). Collectively these results suggest that while all cells in the epidermis use the TCA cycle extensively to generate energy, HFSCs also have increased Ldha expression, Ldh activity, and glycolytic metabolism.

Figure 2A:
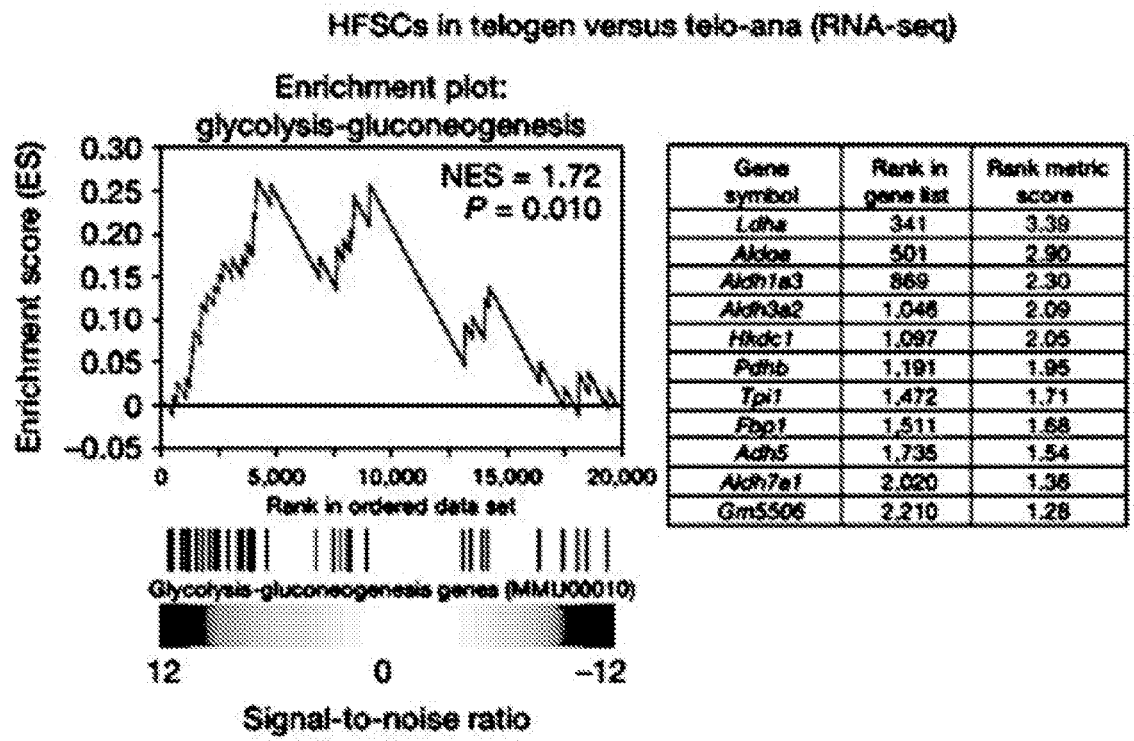
FIGS. 2A-2E. Ldh activity increases during HFSC activation.
Figure 2B:
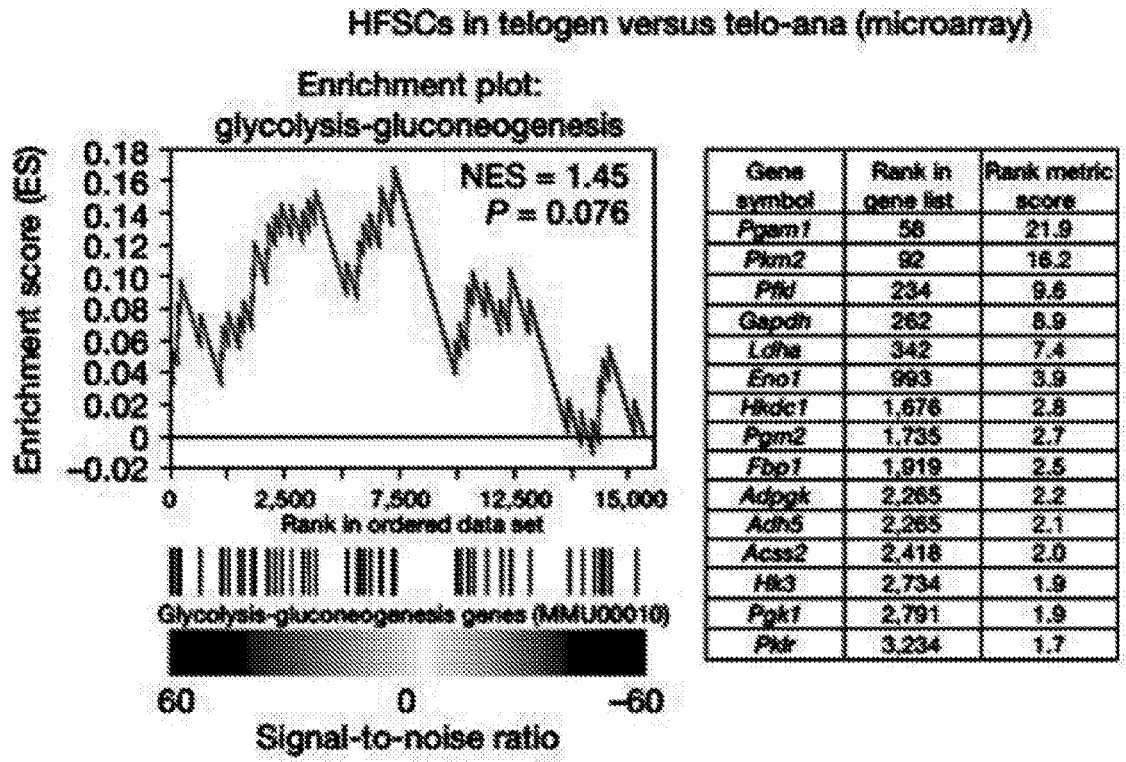
Figure 2C:
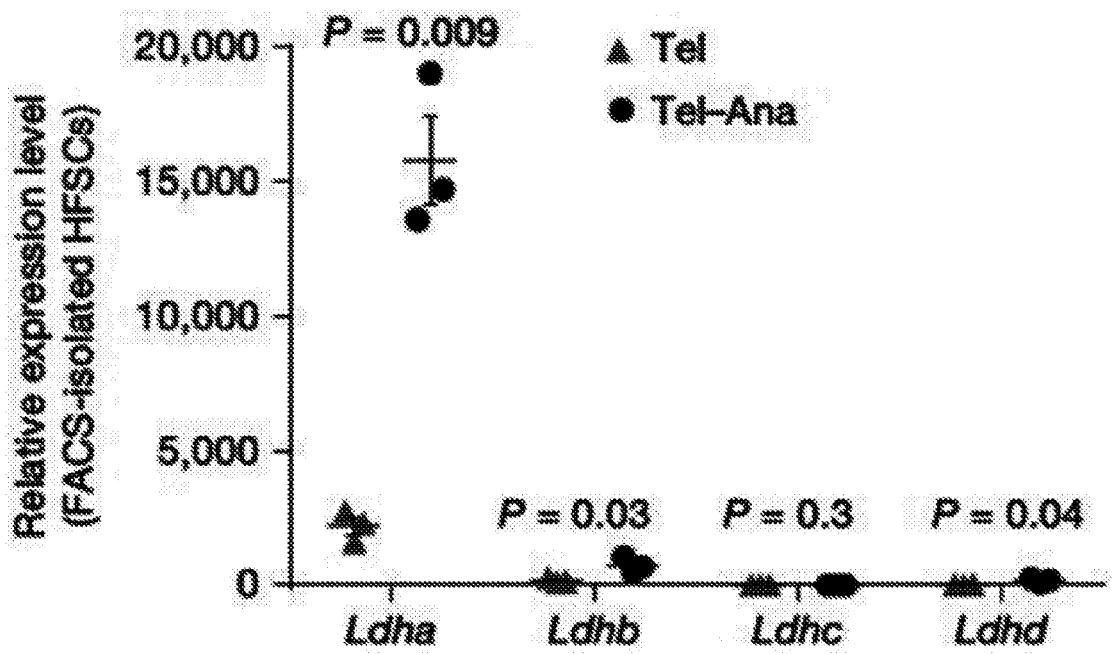
Figure 8A:
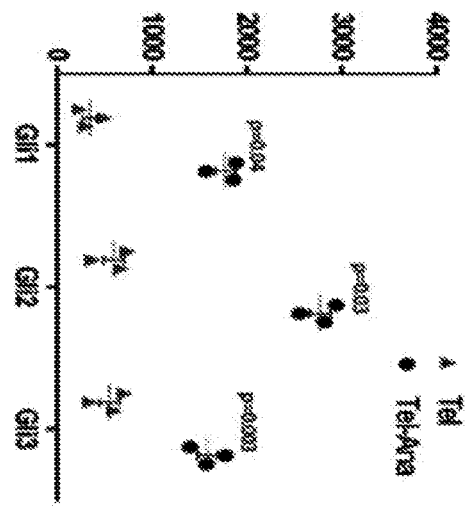
FIGS. 8A-8B. Validation of hair cycle stage.
Figure 8A:
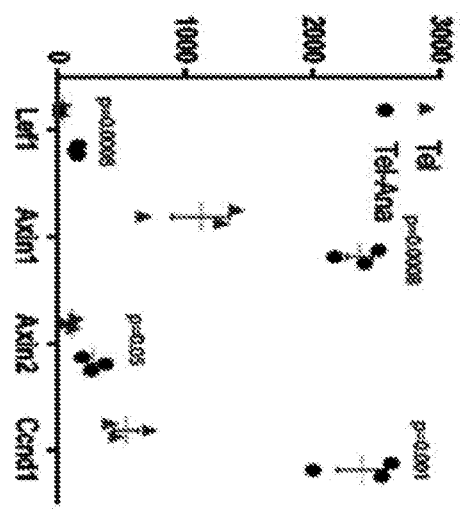
Figure 8A:
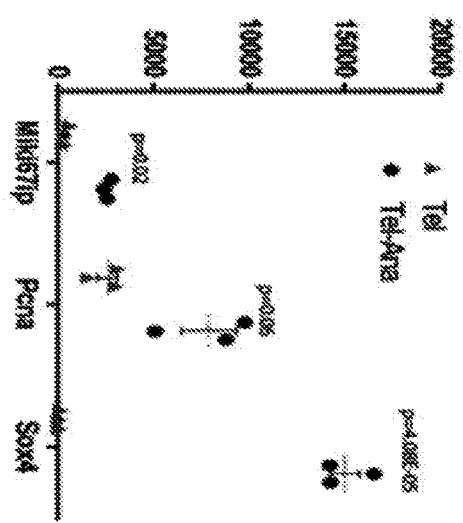

Measuring metabolism across the hair cycle therefore would capture any dynamic changes that occur in HFSCs that correlate with activation or quiescence. Analysis of RNA-seq data from HFSCs isolated during either telogen or the telogen-anagen transition demonstrated not only that Ldha is the predominant Ldh isoform expressed in HFSCs (FIG. 2C), but is also induced during the telogen-anagen transition (FIGS. 2A-2B, NIHGEOGSE67404 and GSE51635). To confirm that the cells analyzed by RNA-seq were indeed either in telogen or the telogen to anagen transition, important markers of this transition were assessed including the Shh and Wnt pathways (Gli1, 2, 3; Lef1, Axin1, Axin2, Ccnd1) as well as proliferation markers (Ki-67, Pcna and Sox4) (FIG. 8A).

Figure 2D:
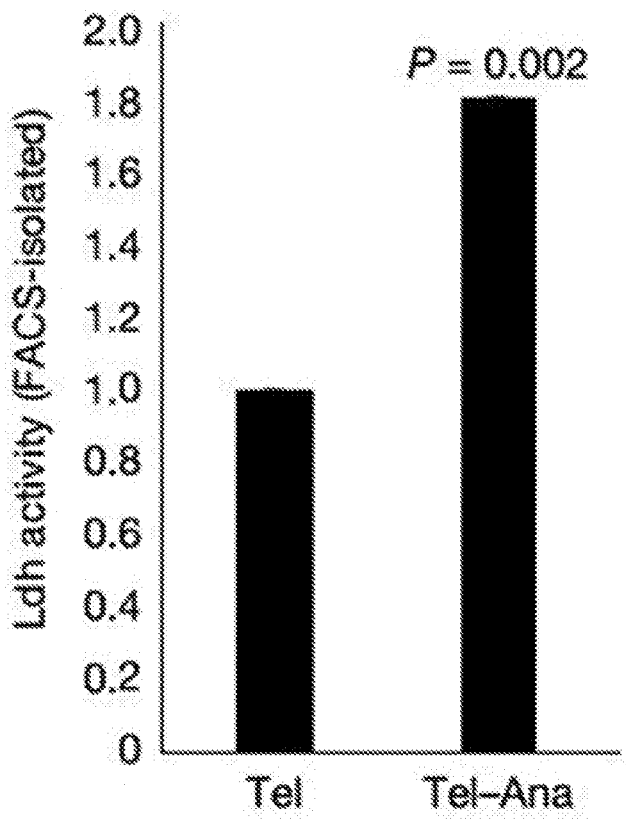
Figure 2E:
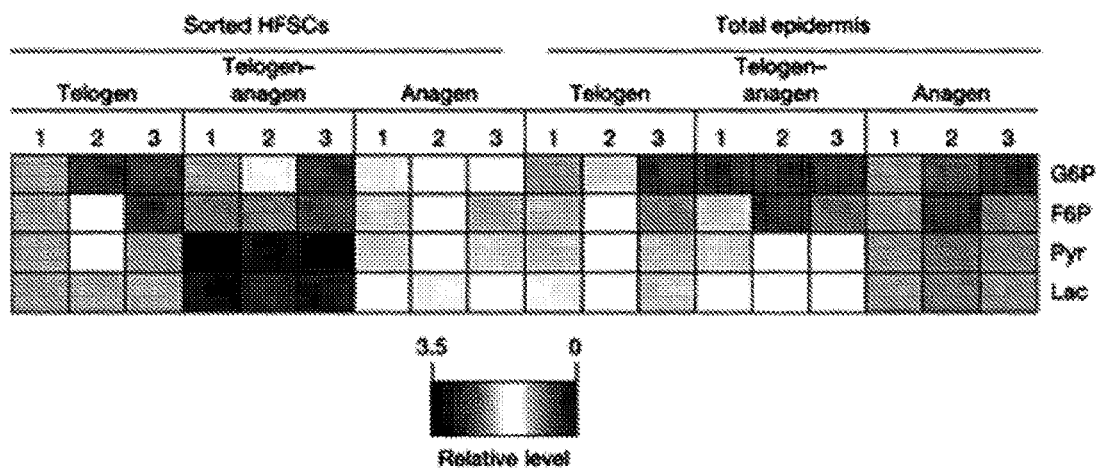
Figure 8B:
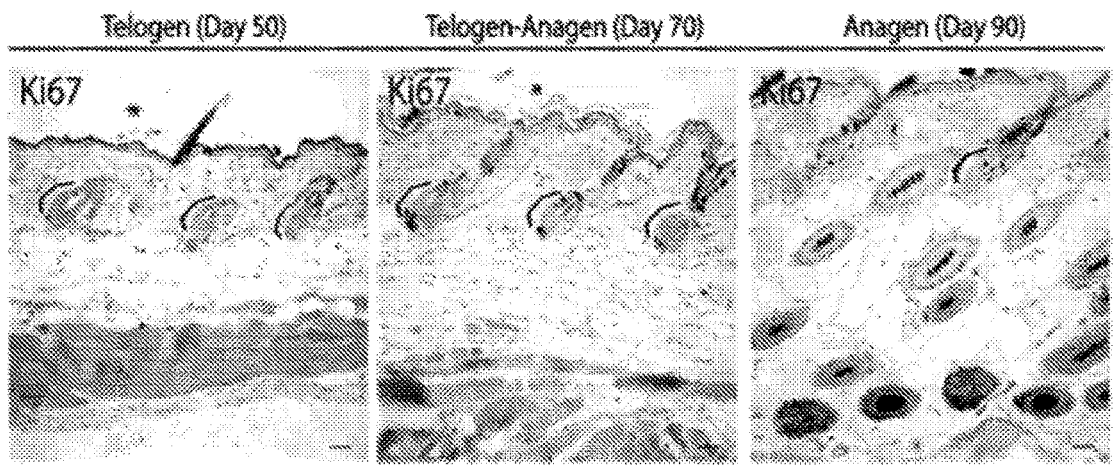

The in vitro Ldh activity assay on lysates from sorted HFSCs uncovered a modest induction of Ldh activity correlating with the telogen to anagen transition (FIG. 2D). Hair cycle staging was validated by Ki-67 immunostaining to determine HFSC activation (FIG. 8B). Additionally, measurements of steady-state metabolites extracted from sorted HFSCs showed an increase in lactate in HFSCs as they transition from telogen to telogen-anagen transition, and then decrease again in anagen as HFSCs return to quiescence (FIG. 2E).

Figure 3A:
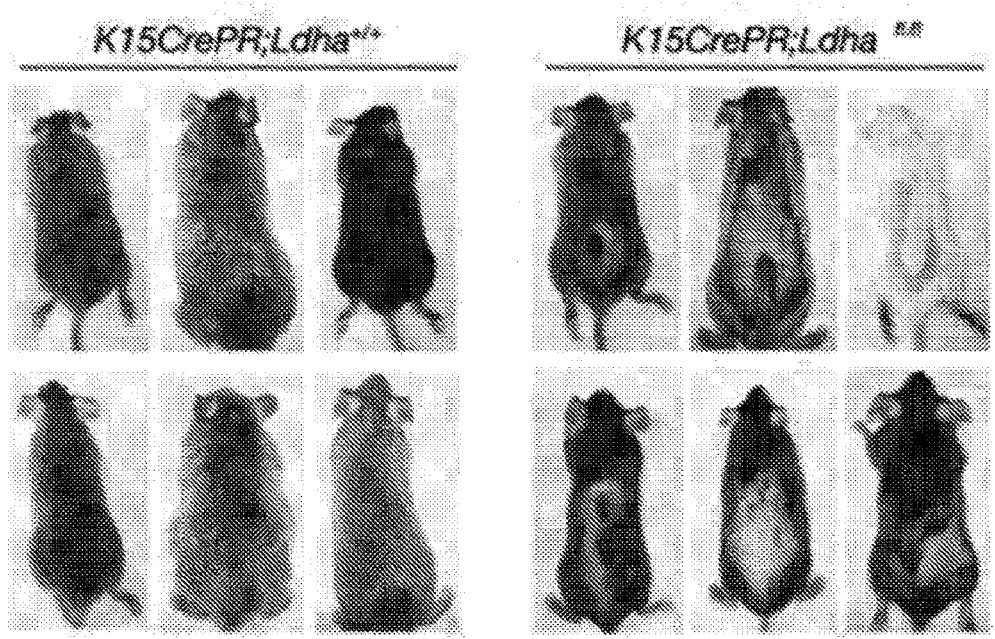
FIGS. 3A-3I. Deletion of Ldha blocks HFSC activation.

To determine whether Ldh activity is functionally related to the ability of HFSCs to remain quiescent or to activate at the start of a hair cycle, we deleted Ldha specifically in the HFSCs. Taking advantage of mice with floxed alleles of Ldha [22], this enzyme was deleted in HFSCs by crossing to mice bearing the K15CrePR allele [14], known to be inducible by Mifepristone specifically in HFSCs. Deletion of Ldha in HFSCs was initiated by administration of Mifepristone during telogen (day 50) and led to a typically mosaic recombination of the floxed alleles across the backskin [14,23]. Mice with HFSC-specific deletion of Ldha failed to undergo a proper hair cycle, with most follicles remaining in telogen across at least 33 pairs of littermates 3-4 weeks after Mifepristone treatment (FIG. 3A). A complete list of transgenic animals including birthdate, sex, and genotype is provided in Table 1.

TABLE 1

Transgeneic animals used in the study.

| Animal ID | DOB | K15CrePR | Ldha | Sex |
|---|---|---|---|---|
| 2990 | Jun. 11, 2015 | + | fl/fl | M |
| 2991 | Jun. 11, 2015 | − | +/+ | M |
| 125 | Jul. 16, 2015 | − | +/+ | F |
| 126 | Jul. 16, 2015 | + | fl/fl | F |
| 127 | Jul. 16, 2015 | + | fl/fl | F |
| 128 | Jul. 16, 2015 | + | fl/fl | F |
| 129 | Jul. 16, 2015 | + | fl/fl | F |
| 130 | Jul. 16, 2015 | + | fl/fl | F |
| 131 | Jul. 16, 2015 | − | fl/fl | F |
| 132 | Jul. 16, 2015 | + | fl/fl | M |
| 133 | Jul. 16, 2015 | − | fl/fl | M |
| 134 | Jul. 16, 2015 | − | +/+ | M |
| 278 | Aug. 30, 2015 | − | +/+ | F |
| 279 | Aug. 30, 2015 | + | fl/fl | F |
| 280 | Aug. 30, 2015 | + | fl/fl | F |
| 281 | Aug. 30, 2015 | − | +/+ | F |
| 473 | Jan. 3, 2016 | + | fl/fl | F |
| 474 | Jan. 3, 2016 | + | +/+ | F |
| 475 | Jan. 3, 2016 | + | +/+ | F |
| 476 | Jan. 3, 2016 | + | +/+ | F |
| 477 | Jan. 3, 2016 | + | fl/fl | F |
| 478 | Jan. 3, 2016 | + | +/+ | M |
| 479 | Jan. 3, 2016 | + | fl/fl | M |
| 480 | Jan. 4, 2016 | − | +/+ | F |
| 481 | Jan. 4, 2016 | + | fl/fl | F |
| 482 | Jan. 4, 2016 | + | fl/fl | M |
| 483 | Jan. 4, 2016 | + | +/+ | M |
| 484 | Jan. 4, 2016 | − | fl/fl | M |
| 485 | Jan. 4, 2016 | + | +/+ | M |
| 486 | Jan. 4, 2016 | − | +/+ | M |
| 487 | Jan. 4, 2016 | + | +/+ | M |
| 488 | Jan. 4, 2016 | − | +/+ | M |
| 489 | Jan. 4, 2016 | + | fl/fl | M |
| 507 | Jan. 25, 2016 | + | fl/fl | F |
| 508 | Jan. 25, 2016 | + | fl/fl | F |
| 509 | Jan. 25, 2016 | − | +/+ | F |
| 510 | Jan. 25, 2016 | + | fl/fl | F |
| 511 | Jan. 25, 2016 | + | +/+ | F |
| 751 | Jun. 9, 2016 | + | fl/fl | F |
| 755 | Jun. 9, 2016 | + | fl/fl | M |
| 758 | Jun. 13, 2016 | + | fl/fl | F |
| 759 | Jun. 13, 2016 | − | +/+ | F |
| 760 | Jun. 13, 2016 | + | fl/fl | F |
| 761 | Jun. 13, 2016 | + | fl/fl | M |
| 762 | Jun. 13, 2016 | + | +/+ | M |
| 763 | Jun. 13, 2016 | − | +/+ | M |
| 813 | Jul. 13, 2016 | + | fl/fl | M |
| 814 | Jul. 13, 2016 | + | fl/fl | M |
| 815 | Jul. 13, 2016 | − | +/+ | M |
| 816 | Jul. 13, 2016 | + | fl/fl | M |
| 818 | Jul. 13, 2016 | + | +/+ | M |
| 819 | Jul. 13, 2016 | − | fl/fl | M |
| 820 | Jul. 13, 2016 | + | fl/fl | M |
| 822 | Jul. 13, 2016 | − | +/+ | M |
| 1050 | Oct. 17, 2016 | − | +/+ | M |
| 1051 | Oct. 17, 2016 | + | fl/fl | M |
| 1052 | Oct. 17, 2016 | − | +/+ | M |
| 1028 | Oct. 14, 2016 | + | fl/fl | M |
| 1029 | Oct. 14, 2016 | − | fl/fl | M |
| 1032 | Oct. 14, 2016 | − | fl/fl | M |
| 1033 | Oct. 14, 2016 | + | fl/fl | M |
| 1191 | Oct. 19, 2016 | + | fl/fl | F |
| 1192 | Oct. 19, 2016 | − | fl/fl | F |
| 1193 | Oct. 19, 2016 | + | fl/fl | F |
| 1194 | Oct. 19, 2016 | + | +/+ | F |
| 1195 | Oct. 19, 2016 | + | fl/fl | F |

| Animal ID | DOB | Lgr5CreER | Ldha | Sex |
|---|---|---|---|---|
| 2780 | Mar. 31, 2015 | − | fl/fl | M |
| 2787 | Mar. 31, 2015 | + | fl/fl | M |
| 13 | Jun. 15, 2015 | + | +/+ | F |
| 14 | Jun. 15, 2015 | + | fl/fl | F |
| 86 | Jul. 3, 2015 | + | fl/fl | F |
| 92 | Jul. 3, 2015 | + | fl/fl | M |
| 93 | Jul. 3, 2015 | − | +/+ | M |

TABLE 1-continued

Transgeneic animals used in the study.

| Animal ID | DOB | | | Sex |
|---|---|---|---|---|
| 81 | Jul. 10, 2015 | + | +/+ | M |
| 83 | Jul. 10, 2015 | + | fl/fl | M |
| 84 | Jul. 3, 2015 | + | +/+ | F |
| 663 | Apr. 26, 2016 | + | fl/fl | F |
| 664 | Apr. 26, 2016 | + | +/+ | F |
| 717 | May 22, 2016 | − | fl/fl | F |
| 718 | May 22, 2016 | + | fl/fl | F |
| 778 | Jun. 16, 2016 | − | +/+ | F |
| 779 | Jun. 16, 2016 | − | fl/fl | F |
| 780 | Jun. 16, 2016 | + | fl/fl | F |
| 781 | Jun. 16, 2016 | − | fl/fl | F |
| 782 | Jun. 16, 2016 | − | +/+ | F |
| 783 | Jun. 16, 2016 | − | +/+ | M |
| 784 | Jun. 16, 2016 | + | fl/fl | M |
| 785 | Jun. 16, 2016 | + | fl/fl | M |
| 786 | Jun. 16, 2016 | + | fl/fl | M |
| 845 | Aug. 4, 2016 | − | +/+ | M |
| 846 | Aug. 4, 2016 | + | fl/fl | M |
| 850 | Aug. 4, 2016 | − | fl/fl | M |
| 851 | Aug. 4, 2016 | + | +/+ | M |
| 892 | Aug. 23, 2016 | + | fl/fl | F |
| 893 | Aug. 23, 2016 | − | fl/fl | F |
| 987 | Nov. 15, 2016 | + | +/+ | F |
| 988 | Nov. 15, 2016 | + | fl/fl | F |
| 989 | Nov. 15, 2016 | + | +/+ | F |
| 990 | Nov. 15, 2016 | + | +/+ | M |
| 1069 | Oct. 16, 2016 | + | fl/fl | F |
| 1070 | Oct. 16, 2016 | − | fl/fl | M |
| 1071 | Oct. 16, 2016 | + | fl/fl | M |
| 1072 | Oct. 16, 2016 | + | fl/fl | M |
| 1073 | Oct. 16, 2016 | + | fl/fl | M |
| 1074 | Oct. 16, 2016 | + | fl/fl | M |
| 1075 | Oct. 16, 2016 | − | fl/fl | M |
| 1076 | Oct. 16, 2016 | + | fl/fl | M |

| Animal ID | DOB | K15CrePR | Mpc1 | Sex |
|---|---|---|---|---|
| 493 | Jan. 8, 2016 | + | +/+ | M |
| 494 | Jan. 8, 2016 | + | fl/fl | M |
| 495 | Jan. 8, 2016 | − | fl/fl | M |
| 550 | Feb. 17, 2016 | − | +/+ | F |
| 551 | Feb. 17, 2016 | + | fl/fl | F |
| 552 | Feb. 17, 2016 | − | +/+ | F |
| 631 | Mar. 24, 2016 | + | fl/fl | F |
| 633 | Mar. 24, 2016 | + | +/+ | F |
| 634 | Mar. 24, 2016 | − | +/+ | F |
| 680 | Apr. 27, 2016 | + | fl/fl | F |
| 681 | Apr. 27, 2016 | + | +/+ | F |
| 682 | Apr. 27, 2016 | − | fl/fl | F |
| 683 | Apr. 27, 2016 | + | fl/fl | F |
| 684 | Apr. 27, 2016 | − | fl/fl | F |
| 768 | Jun. 12, 2016 | − | fl/fl | F |
| 769 | Jun. 12, 2016 | + | fl/fl | F |
| 770 | Jun. 12, 2016 | + | fl/fl | F |
| 860 | Jul. 18, 2016 | + | +/+ | F |
| 861 | Jul. 18, 2016 | + | fl/fl | F |
| 875 | Jul. 22, 2016 | + | fl/fl | M |
| 876 | Jul. 22, 2016 | + | +/+ | M |
| 880 | Aug. 22, 2016 | + | fl/fl | M |
| 881 | Aug. 22, 2016 | + | +/+ | M |
| 991 | Sep. 18, 2016 | + | fl/fl | M |
| 992 | Sep. 18, 2016 | + | +/+ | M |
| 993 | Sep. 18, 2016 | + | +/+ | F |
| 994 | Sep. 18, 2016 | + | fl/fl | F |
| 995 | Sep. 18, 2016 | + | +/+ | M |
| 996 | Sep. 18, 2016 | + | fl/fl | M |
| 997 | Sep. 18, 2016 | − | fl/fl | M |

| Animal ID | DOB | Lgr5CreER | Mpc1 | Sex |
|---|---|---|---|---|
| 5652 | Jul. 6, 2016 | + | fl/fl | M |
| 5653 | Jul. 6, 2016 | + | fl/fl | M |
| 5654 | Jul. 6, 2016 | − | fl/fl | M |
| 5655 | Jul. 6, 2016 | + | fl/fl | F |
| 5656 | Jul. 6, 2016 | − | fl/fl | F |
| 5657 | Jul. 6, 2016 | − | fl/fl | F |
| 5658 | Jul. 6, 2016 | − | fl/fl | F |
| 5659 | Jul. 6, 2016 | − | fl/fl | F |
| 5660 | Jul. 6, 2016 | + | fl/fl | F |
| 5661 | Jul. 6, 2016 | + | fl/fl | F |
| 5662 | Jul. 6, 2016 | − | fl/fl | F |
| 5663 | Jul. 6, 2016 | + | fl/fl | M |
| 5664 | Jul. 6, 2016 | + | fl/fl | M |
| 5665 | Jul. 6, 2016 | − | fl/fl | M |
| 5666 | Jul. 6, 2016 | + | fl/fl | F |
| 5667 | Jul. 6, 2016 | + | fl/fl | F |
| 5668 | Jul. 9, 2016 | + | +/+ | F |
| 5672 | Jul. 9, 2016 | + | +/+ | M |
| 5673 | Jul. 9, 2016 | + | +/+ | M |
| 5674 | Jul. 9, 2016 | + | +/+ | M |
| 5675 | Jul. 9, 2016 | + | +/+ | M |
| 5882 | Aug. 17, 2016 | + | fl/fl | M |
| 5883 | Aug. 17, 2016 | + | fl/fl | M |
| 5884 | Aug. 21, 2016 | + | +/+ | F |
| 5886 | Aug. 21, 2016 | + | +/+ | F |
| 5890 | Aug. 21, 2016 | + | +/+ | M |
| 5891 | Aug. 21, 2016 | + | +/+ | M |
| 5892 | Aug. 24, 2016 | + | +/+ | F |
| 5893 | Aug. 24, 2016 | + | +/+ | F |
| 5896 | Aug. 24, 2016 | + | +/+ | M |
| 5897 | Aug. 24, 2016 | + | +/+ | M |
| 5898 | Aug. 27, 2016 | + | fl/fl | F |

| Animal ID | DOB | Lgr6CreER | Mpc1 | Sex |
|---|---|---|---|---|
| 659 | Apr. 26, 2016 | − | fl/fl | M |
| 660 | Apr. 26, 2016 | + | fl/fl | F |
| 661 | Apr. 26, 2016 | + | fl/fl | M |
| 662 | Apr. 26, 2016 | − | fl/fl | M |
| 693 | Apr. 28, 2016 | + | fl/fl | M |
| 694 | Apr. 28, 2016 | − | fl/fl | M |
| 696 | Apr. 28, 2016 | + | fl/fl | M |
| 697 | Apr. 28, 2016 | + | fl/fl | M |
| 701 | May 9, 2016 | + | +/+ | F |
| 702 | May 9, 2016 | + | +/+ | F |
| 703 | May 9, 2016 | + | fl/fl | F |
| 704 | May 9, 2016 | − | fl/fl | M |
| 705 | May 9, 2016 | + | fl/fl | M |
| 735 | Jun. 4, 2016 | + | fl/fl | M |
| 736 | Jun. 4, 2016 | − | fl/fl | M |
| 737 | Jun. 4, 2016 | + | fl/fl | M |
| 777 | Jun. 4, 2016 | + | +/+ | M |
| 793 | Jul. 12, 2016 | + | fl/fl | F |
| 794 | Jul. 12, 2016 | − | fl/fl | F |
| 795 | Jul. 12, 2016 | + | fl/fl | F |

Figure 3B:
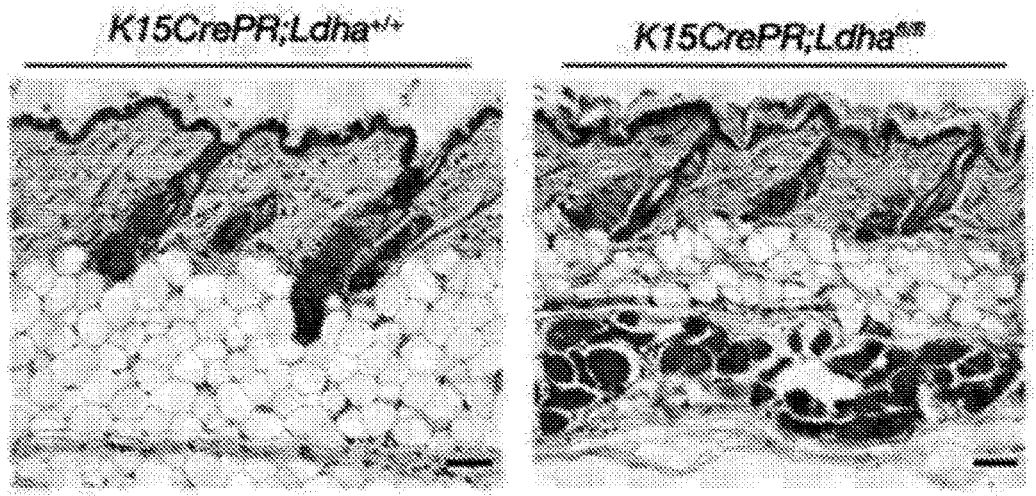
Figure 3C:
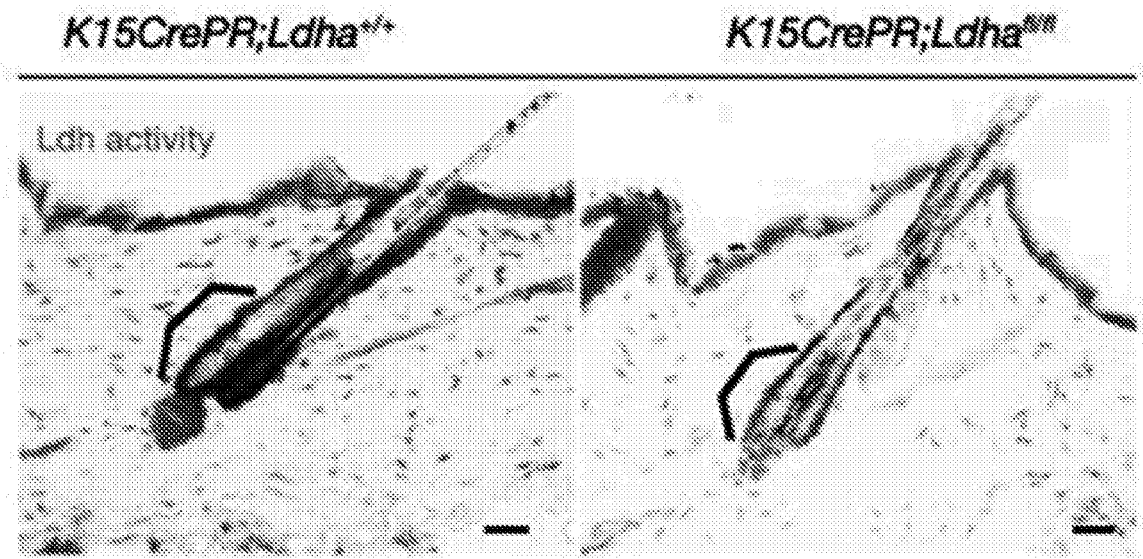
Figure 3D:
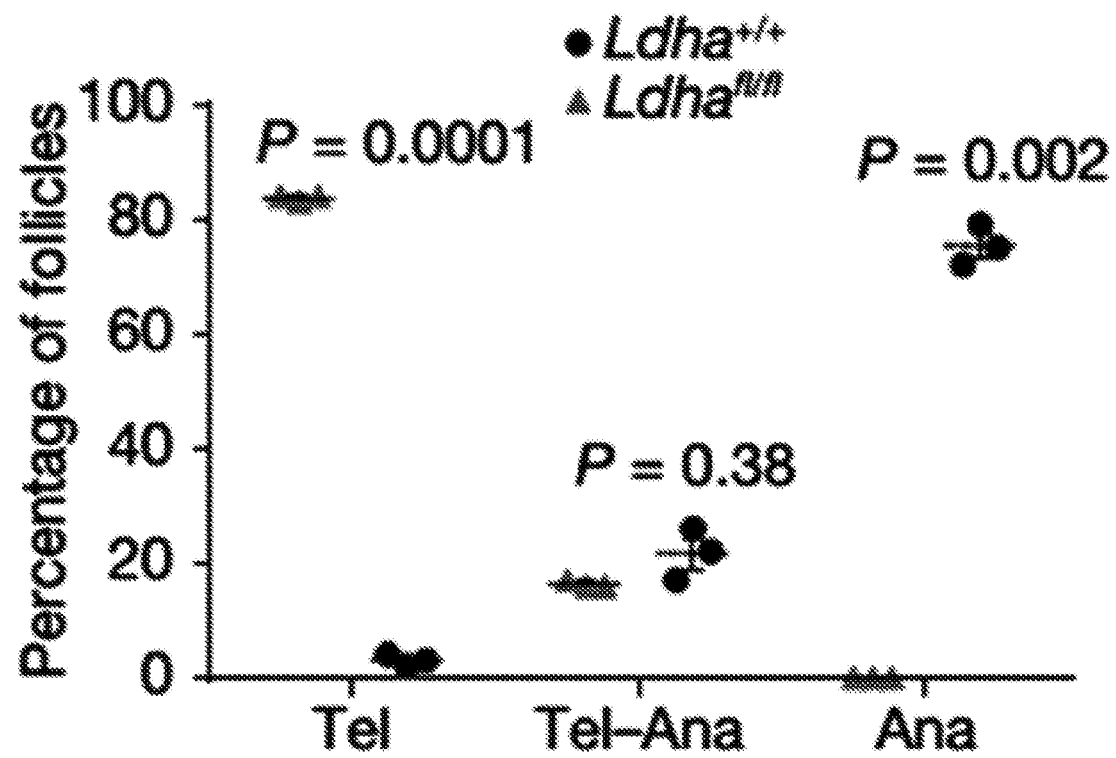

Histology showed that WT hair follicles entered into the telogen to anagen transition typically by day 70, and this was accompanied by typical expansion of the hypodermis below (FIG. 3B). However, in backskin with deletion of Ldha, the hypodermis did not expand, and the telogen to anagen transition was severely abrogated (FIG. 3B). In areas of strong phenotypic penetrance, Ldh activity was severely abrogated in the HFSC compartment (FIG. 3C), demonstrating that the Ldha allele is critically important for Ldh activity in HFSCs and consistent with the fact that the 'a' isoform of Ldh is expressed at the highest level. Quantification of hair cycle progression across numerous animals indicated that most follicles lacking Ldha remained in telogen (FIG. 3D).

Figure 3E:
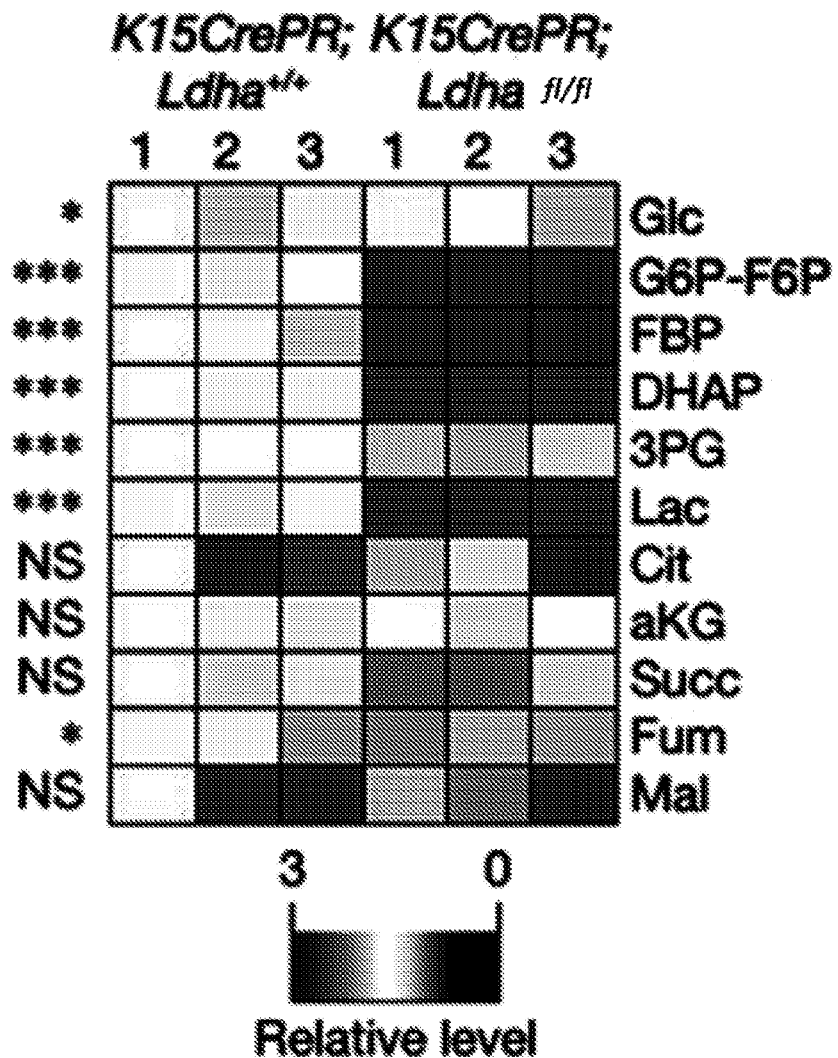
Figure 3F:
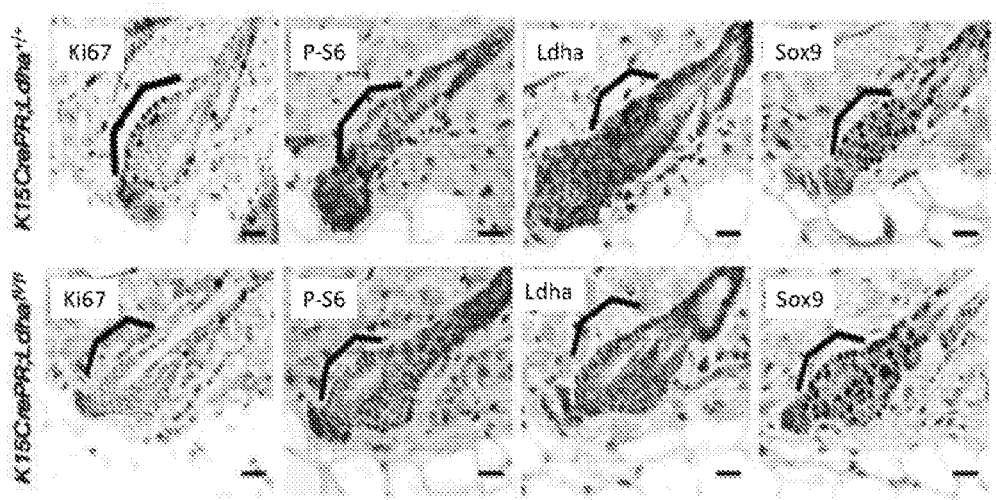
Figure 3G:
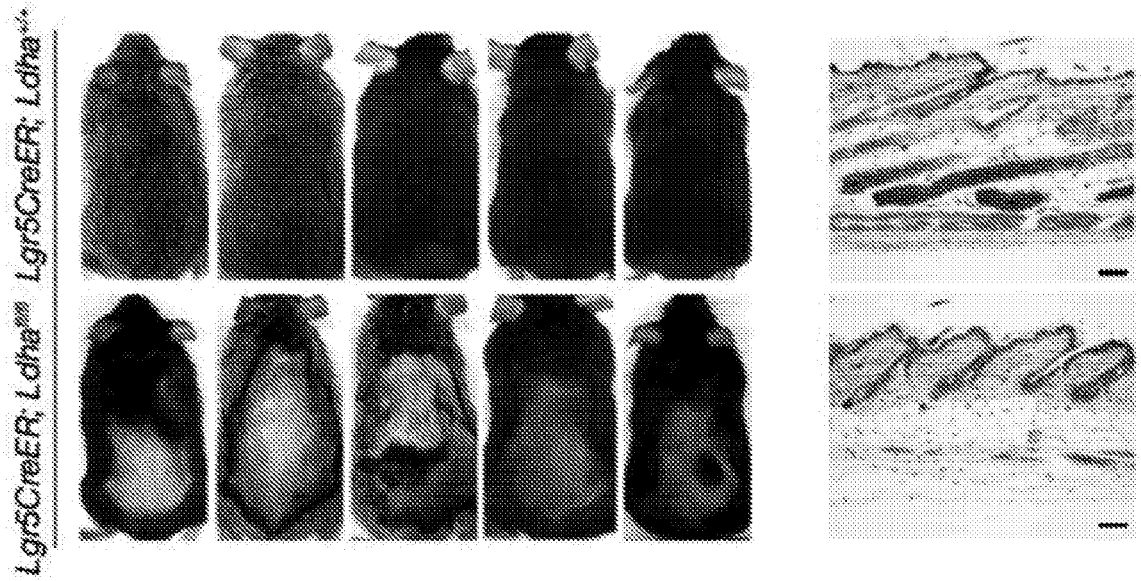
Figure 3H:
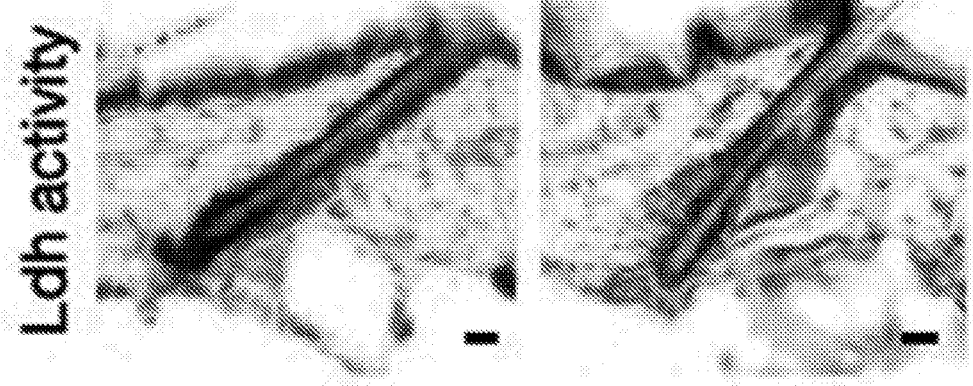
Figure 3I:
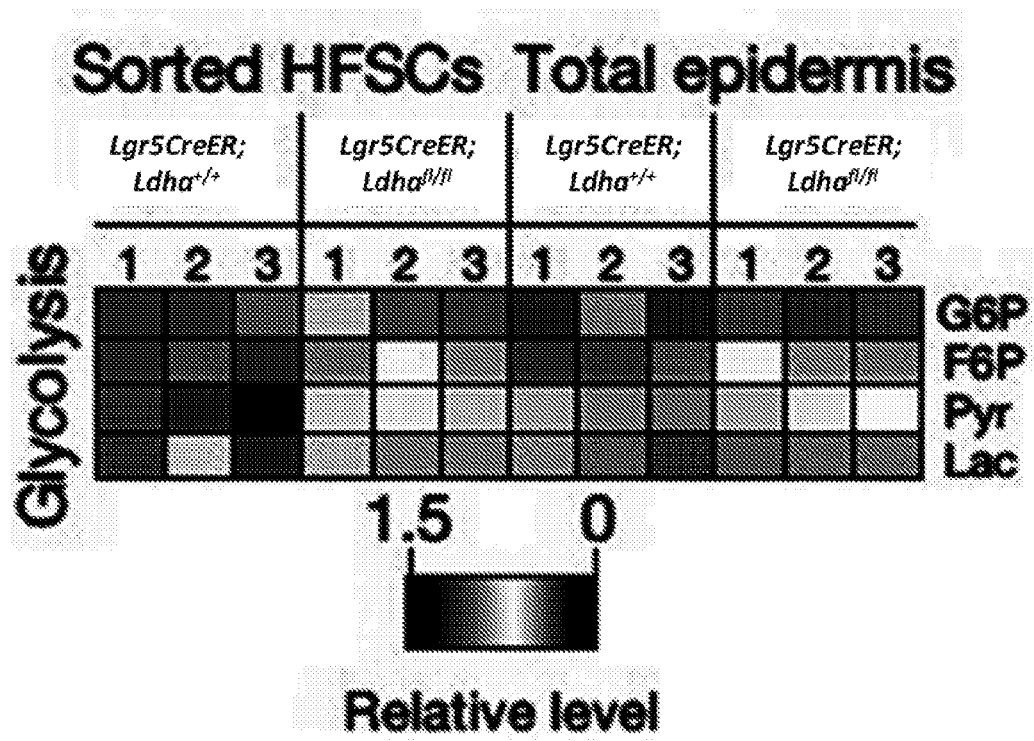

In addition, to confirm the phenotypes, we also deleted Ldha with an independent HFSC-specific Cre strategy. Lgr5-CreER has been used for lineage tracing in a variety of adult stem cell models, and has been shown to mark cells with high regenerative capacity, including HFSCs [24]. Lgr5CreER;Ldha$^{fl/fl}$ mice, treated with tamoxifen at postnatal day 50 prior to a synchronized hair cycle, also failed to activate anagen across at least 20 littermate pairs (FIG. 3G). in situ Ldh assay and metabolomics confirmed the successful deletion of Ldha in these animals (FIGS. 3H and 3I).

Figure 9A:
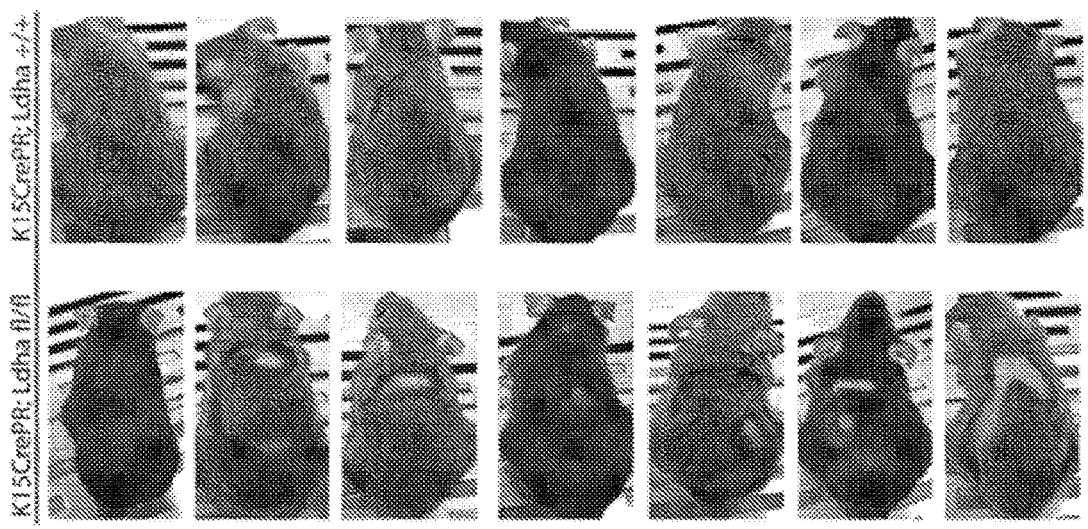
FIGS. 9A-9D. Long term deletion of Ldha in HFSCs.
Figure 9B:
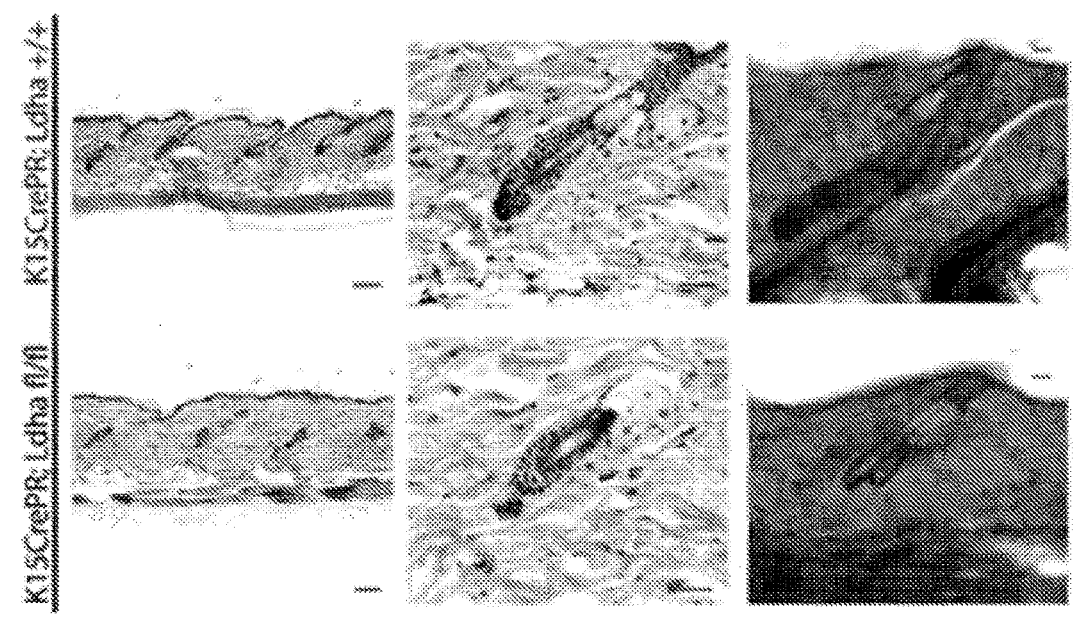
Figure 9C:
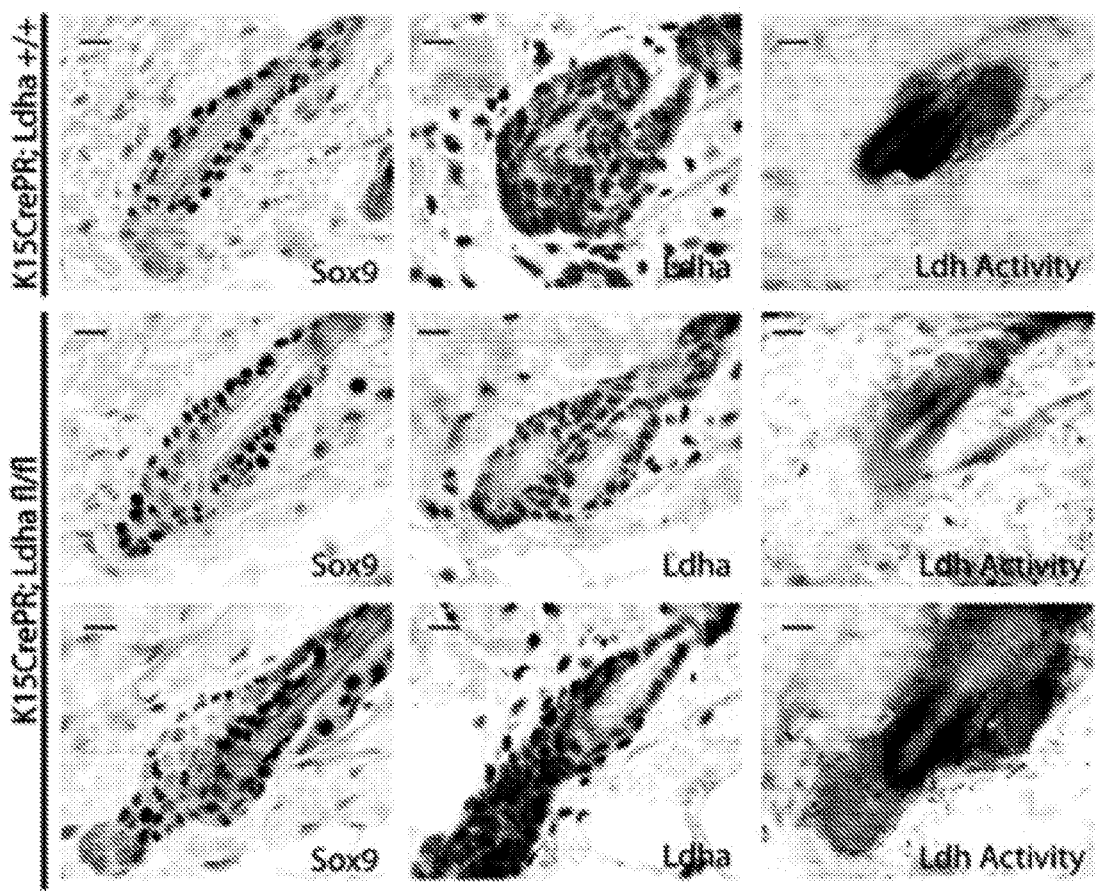

We also monitored the effect of loss of Ldha activity in K15+ cells over a six month period and found that deletion of Ldha led to a mosaic, but permanent block of HFSC activation in some portions of the backskin (FIG. 9A). These data confirm that Ldh activity is required for HFSC activation, and is not simply a marker of HFSCs. A closer look at these long term Ldha deletions showed that Ldha-null HFSCs continued expressing typical markers, but lacked Ldh activity, and failed to initiate new hair cycles, while those follicles that escaped deletion continued to express Ldha and to cycle normally (FIGS. 9B and 9C).

Figure 9D:
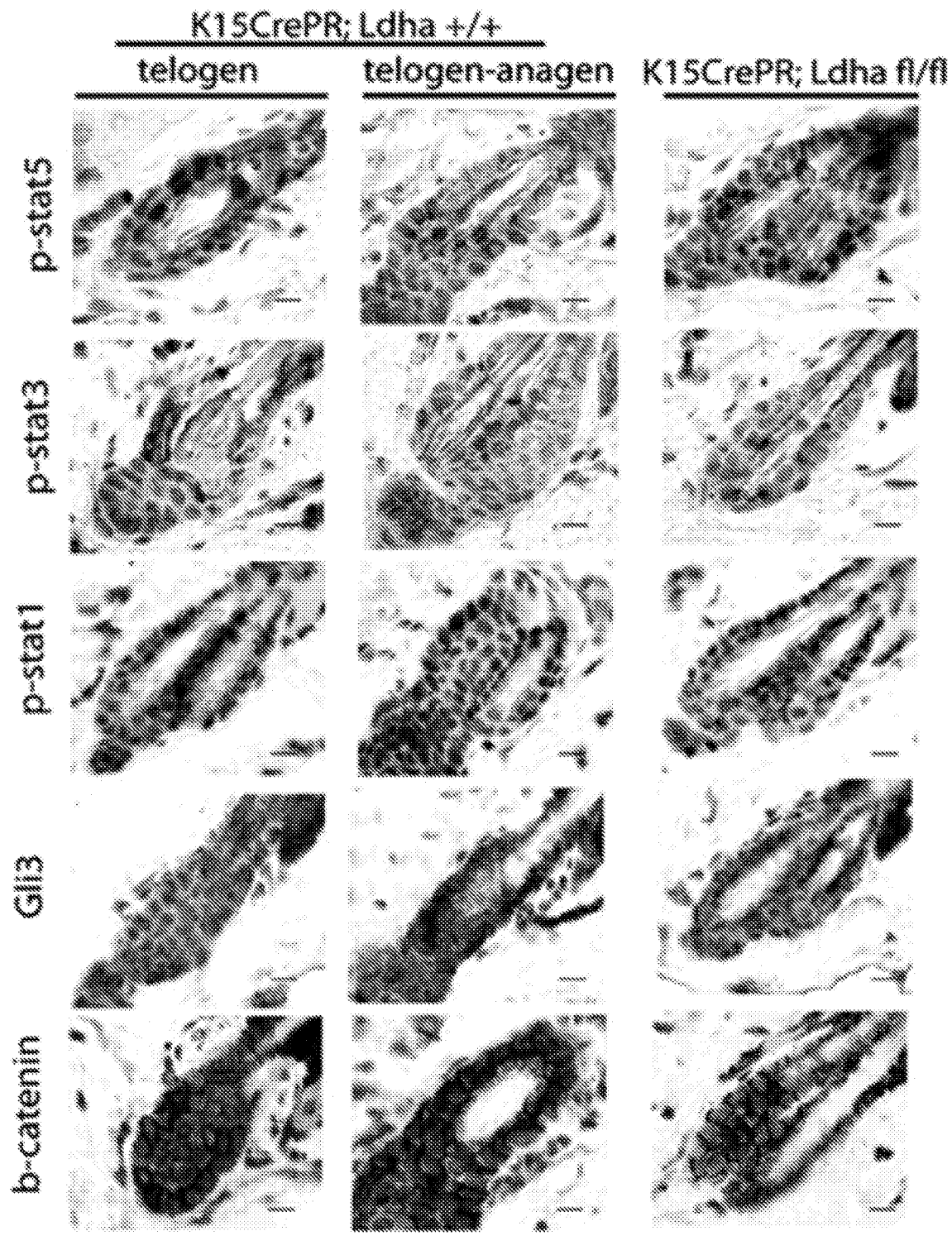

After sorting HFSCs from animals with or without Ldha deletion, LC-MS-based metabolomics analysis demonstrated that lactate levels, as well as levels of other glycolytic metabolites, were strongly reduced in the absence of Ldha (FIG. 3E), functional evidence that the targeting strategy was successful. The fact that glycolytic metabolites upstream of lactate were also suppressed suggests that HFSCs could be adapting their metabolism to account for the loss of Ldh activity. Immunostaining for markers of HFSC activation and proliferation indicated a failure of HFSC activation. Ki67 and pS6 have been clearly demonstrated to be abundant in the HFSC niche at the start of the hair cycle [25], and both of these markers were absent in Ldha deleted backskin (FIG. 3F). Immunostaining for Ldha also confirmed successful deletion of this protein, while staining for Sox9, a marker of HFSCs indicated that these cells remained in their niche, but just failed to activate in the absence of Ldha (FIG. 3F). Induction of the hair cycle is also thought to be regulated by signaling from the Shh, Wnt and Jak-Stat pathways. We assayed each of these by IHC in normal or Ldha deletion follicles and found that in general these pathways were not activated in Ldha-null HFSCs that failed to enter a telogen-anagen transition (FIG. 9D).

To determine whether induction of lactate production could affect HFSC activation or the hair cycle, we crossed K15CrePR animals to those floxed for mitochondrial pyruvate carrier 1 (Mpc1) (K15CrePR;Mpc1$^{fl/fl}$). Mpc1, as a heterodimer with Mpc2, forms the mitochondrial pyruvate carrier MPC, a transporter on the inner mitochondrial membrane required for pyruvate entry into the mitochondria [26]. Loss of function of Mpc1 has been shown to drive lactate production through enhanced conversion of pyruvate to lactate by Ldh [27].

Figure 4A:
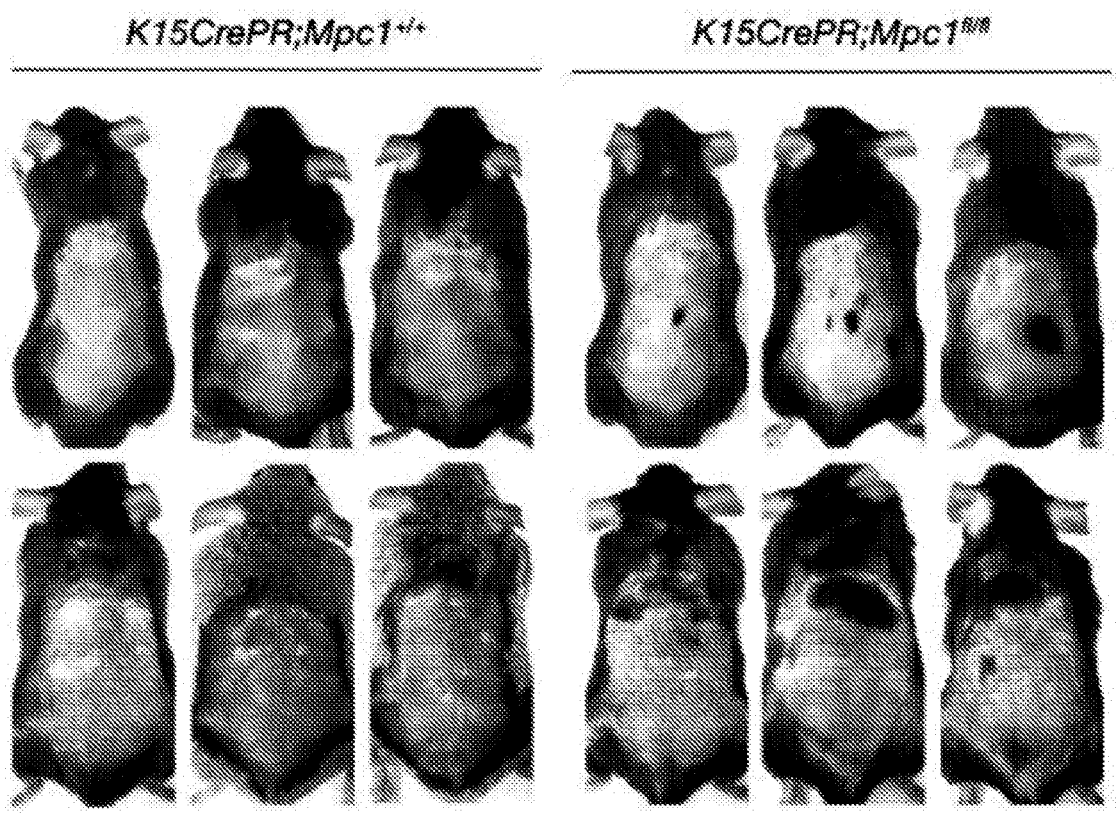
FIGS. 4A-4G. Deletion of Mpc1 increases lactate production and activation of HFSCs.
Figure 4B:
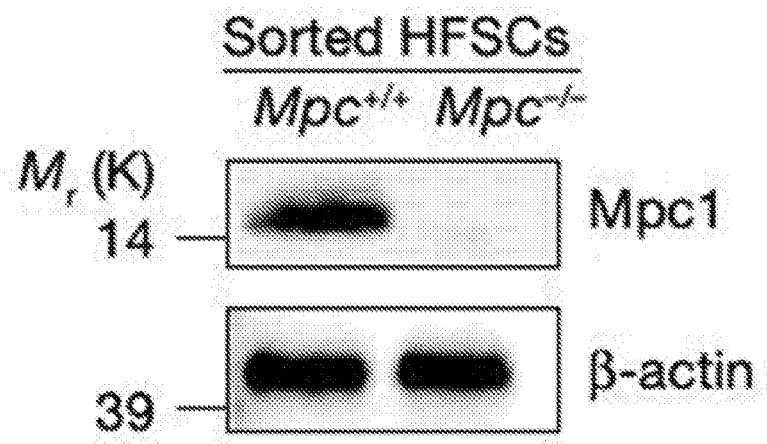
Figure 4C:
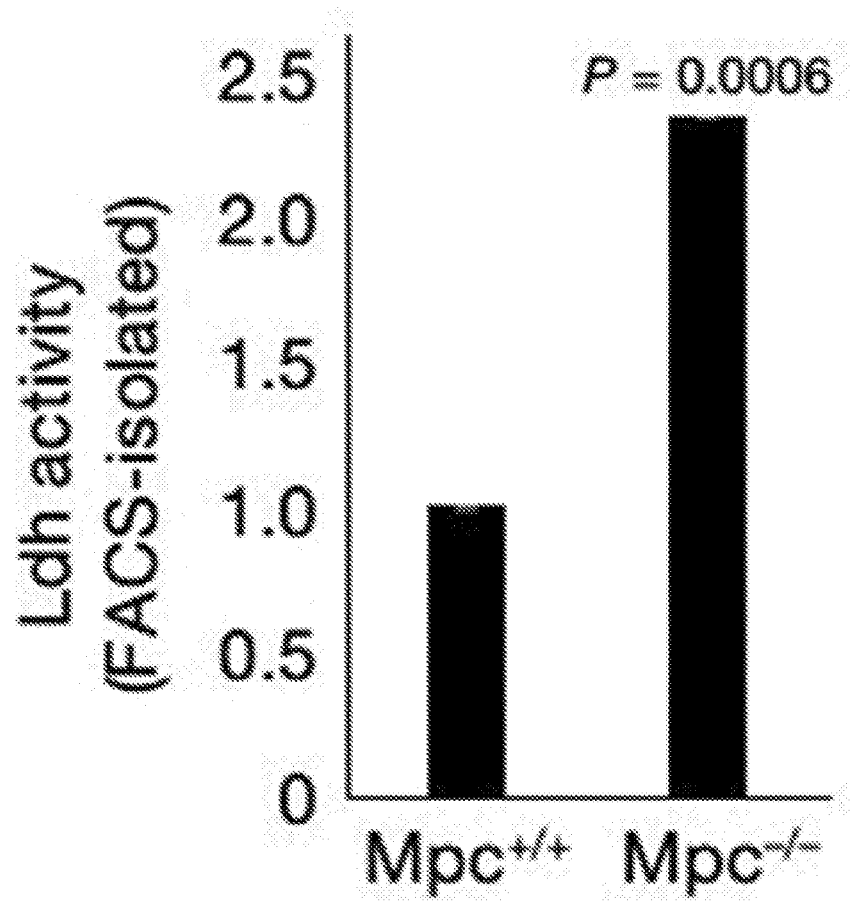
Figure 4D:
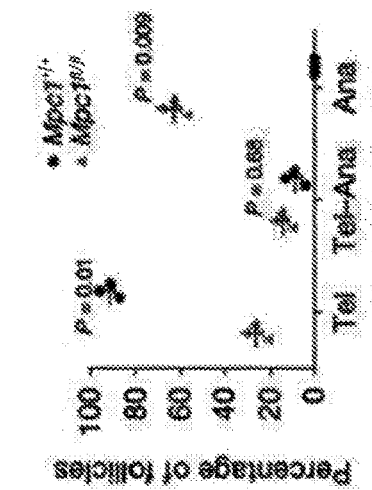
Figure 4D:
Figure 4E:
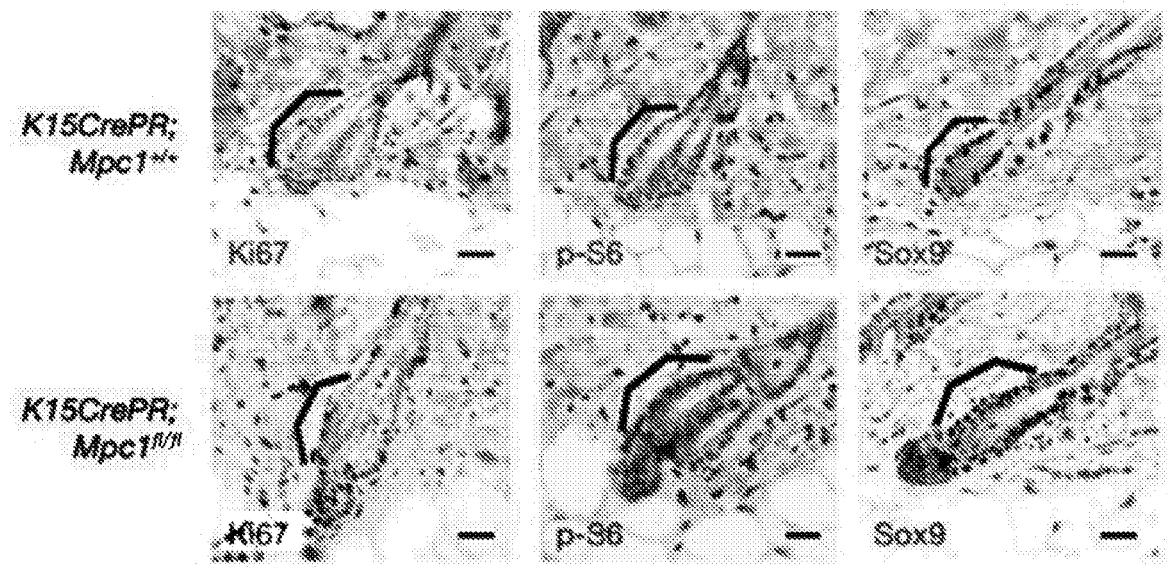
Figure 4F:
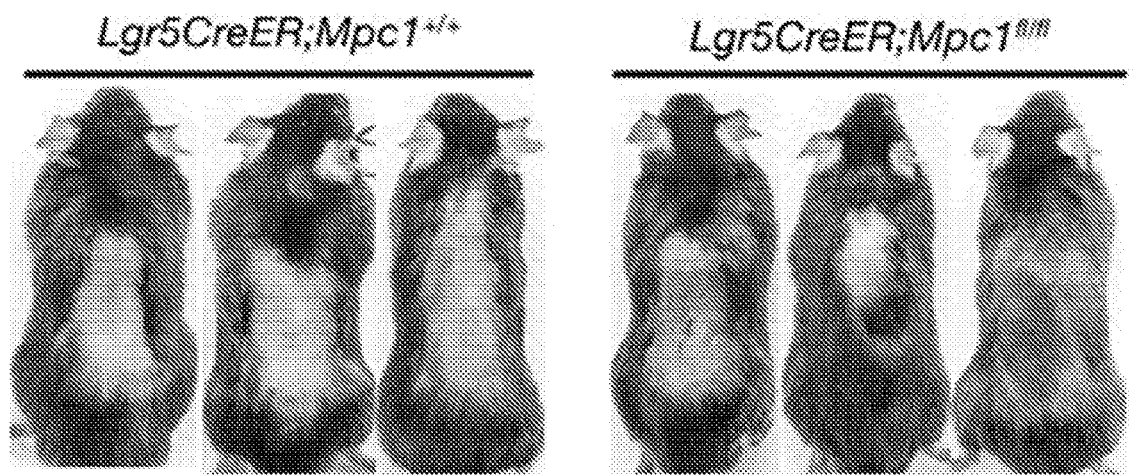
Figure 4G:
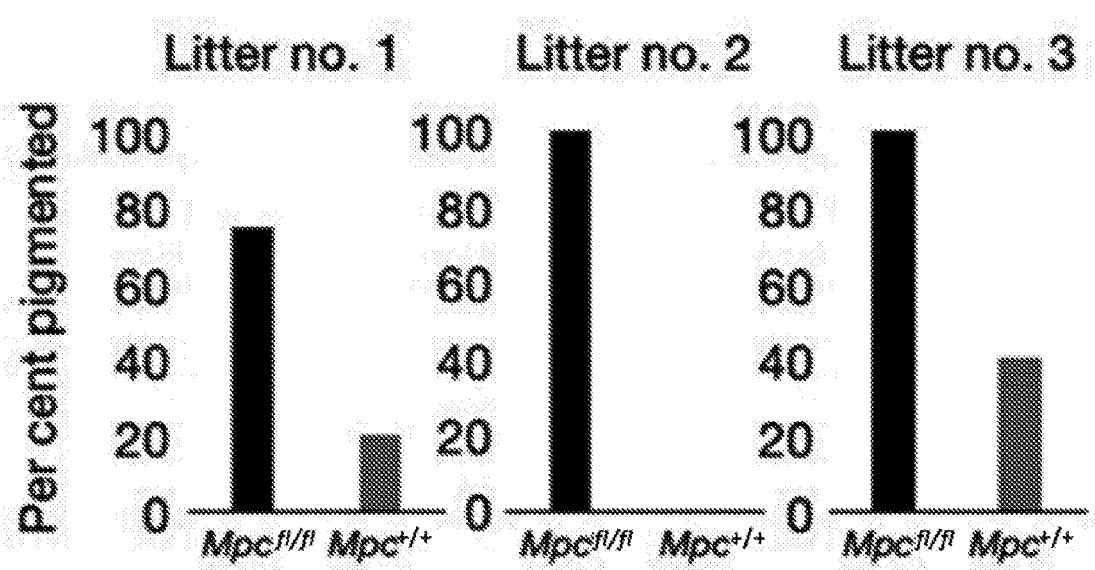
Figure 10A:
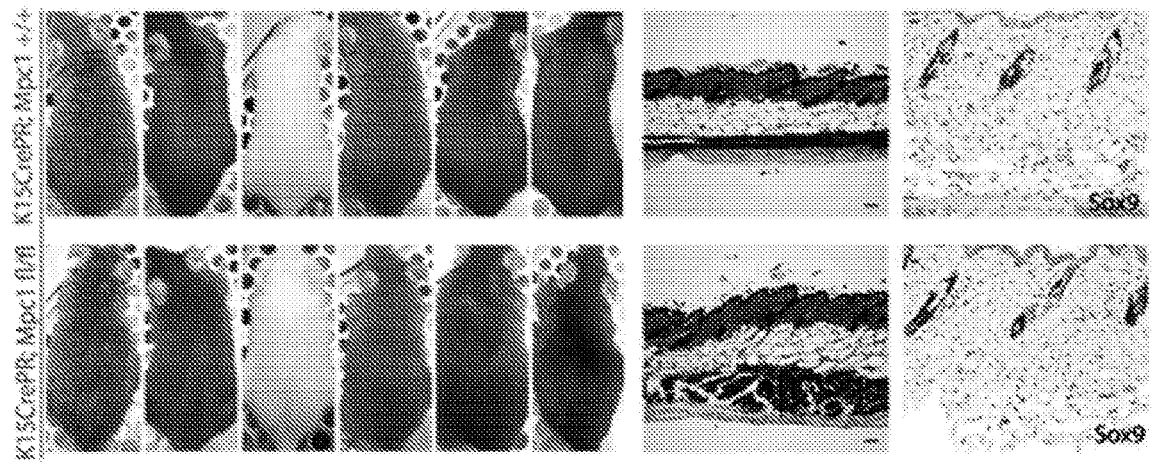
FIGS. 10A-10D. Long term deletion of Mpc1 in HFSCs.
Figure 10B:
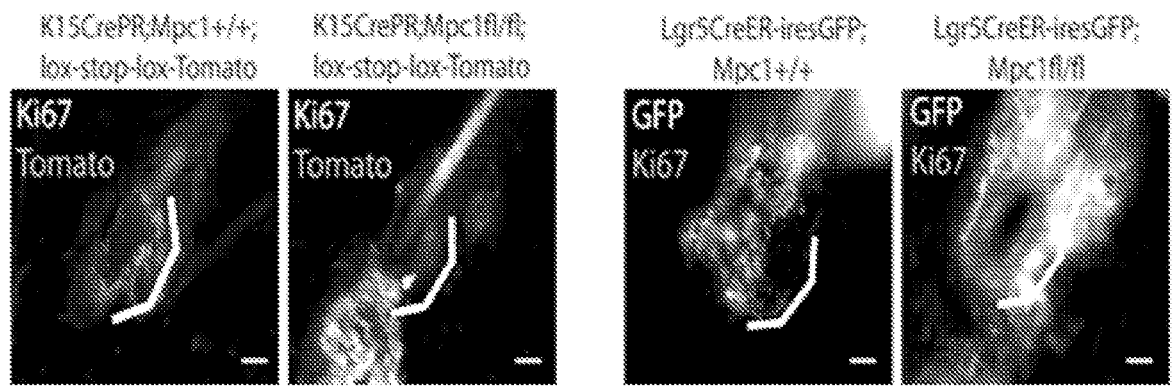

In animals with Mpc1 deletion in HFSCs, we observed a strong acceleration of the ventral and dorsal hair cycles with all the typical features of a telogen-anagen transition (FIG. 4A) (n=12 littermate pairs). Mifepristone treated K15CrePR;Mpc1$^{fl/fl}$ animals were the only to show any signs of dorsal anagen by day 70. Western blotting on sorted HFSCs validated the loss of Mpc1 protein (FIG. 4B). Importantly, purified HFSCs lacking Mpc1 showed a strong induction of Ldh activity (FIG. 4C). Quantification of the dorsal hair cycle across three pairs of littermates showed a strong induction of anagen in backskin lacking Mpc1 (FIG. 4D, right), and histology showed that the anagen induction was normal in appearance with a typical hypodermal expansion (FIG. 4D). Immunostaining demonstrated the induction in Mpc1-null HFSCs of various markers of hair cycle activation such as Ki-67 and pS6, while Sox9 expression was unaffected (FIG. 4E). Long term deletion of Mpc1 did not lead to aberrant follicles or exhaustion of HFSCs as judged by pathology and staining for Sox9 (FIG. 10A). Furthermore, deletion of Mpc1 with Lgr5CreER showed a very similar phenotype as deletion with K15CrePR (FIGS. 4F and 4G), validating the fact that deletion of this protein in HFSCs leads to their activation (n=12 pairs of littermates). Finally, immunofluorescence for the Ires-GFP of the Lgr5CreER transgene along with Ki-67 and lineage tracing with K15CrePR;Mpc1$^{fl/fl}$;1sl-Tomato mice also demonstrated that the HFSCs were indeed proliferative following induction of Mpc1 deletion by tamoxifen or mifepristone (FIG. 10B).

Figure 10C:
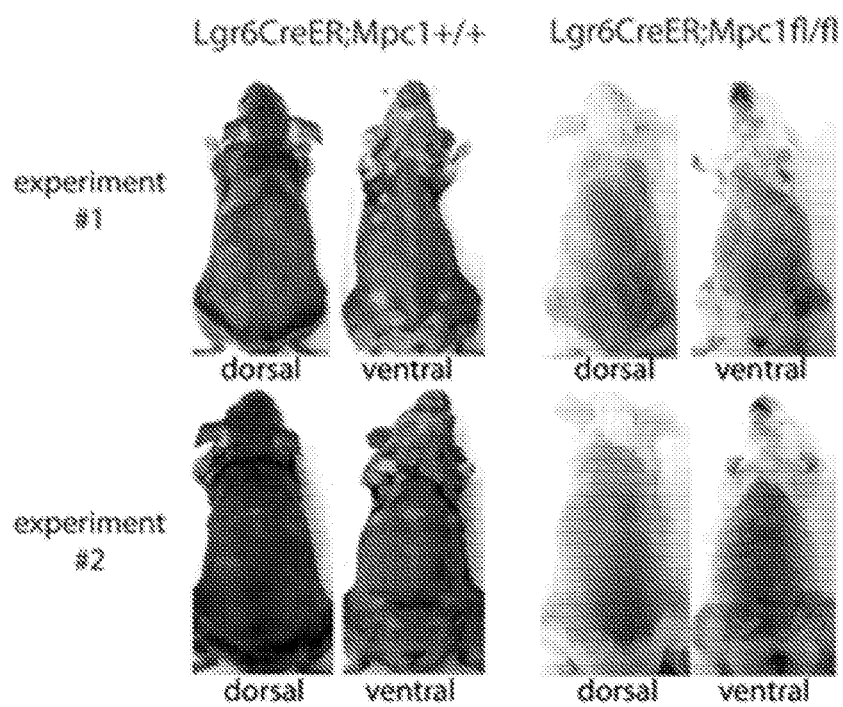
Figure 10D:
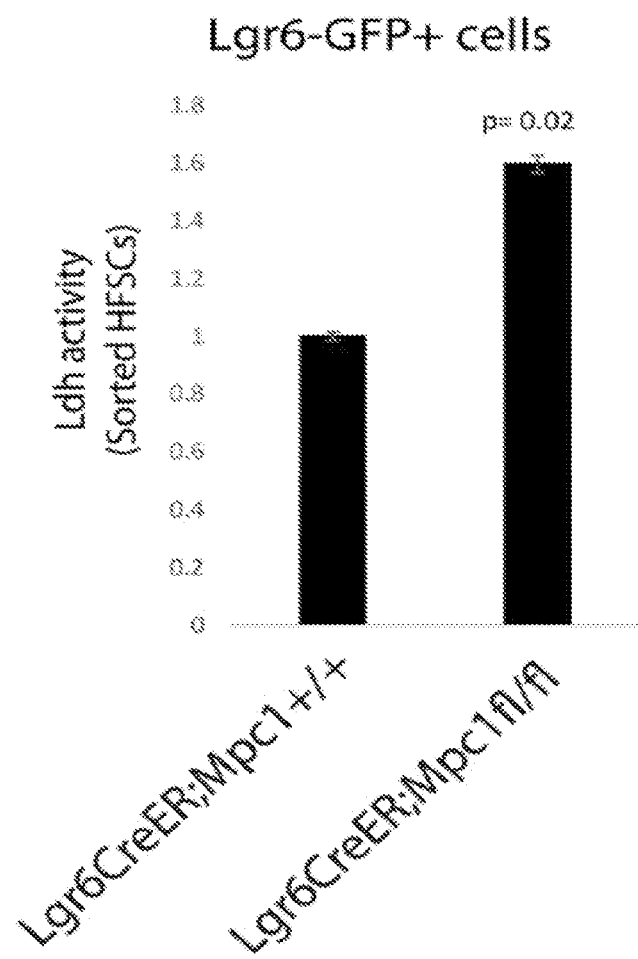

On the other hand, deletion of Mpc1 in the top of the follicle (infundibulum, sebaceous gland progenitors) and a limited number of interfollicular cells with Lgr6CreER [28] did not appear to affect the hair cycle (Lgr6CreER;Mpc1$^{fl/fl}$) (n=10 littermate pairs) or general skin homeostasis over at least 2 months (FIG. 10C). Ldh activity assay on Lgr6+ cells sorted from wildtype or deletion skin demonstrated that the Mpc1 deletion was effective (FIG. 10D). Together, these results indicate that increasing lactate production through the blockade of pyruvate into the TCA cycle has a strong effect on the ability of HFSCs, but not other cells in the hair follicle, to become activated to initiate a new hair cycle.

Figure 6A:
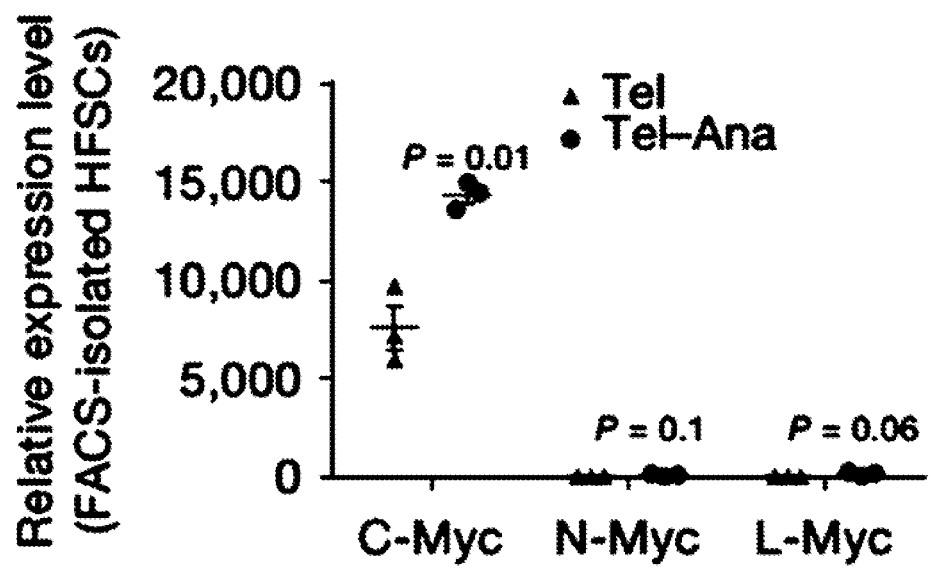
FIGS. 6A-6H. Stimulation of Myc levels promotes HFSC activation.
Figure 6B:
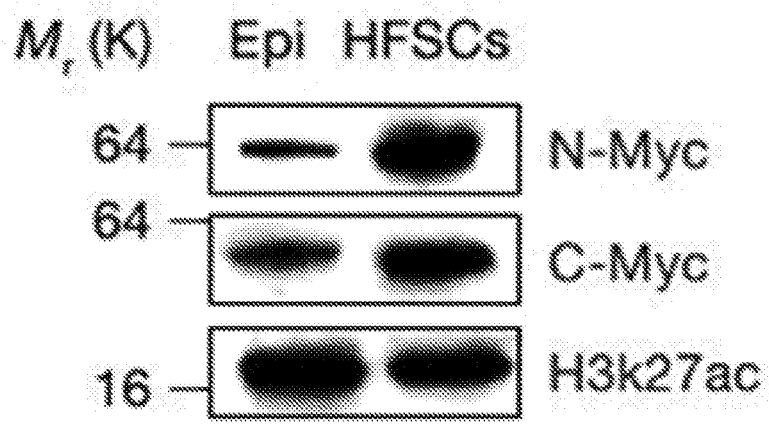

Because alteration of lactate production in HFSCs appeared to regulate their activation, we attempted to identify other small molecules that could take advantage of these findings to induce the hair cycle. Ldha is known to be transcriptionally regulated by Myc, which has been shown to play an important role in HFSC activation and the hair cycle [30-32]. RNA-seq on sorted HFSCs indicated that Myc is induced during the telogen-anagen transition (FIG. 6A). Western blotting for both c-Myc and n-Myc in sorted HFSCs versus total epidermis showed a strong increase in Myc protein in the nuclei of HFSCs (FIG. 6B).

Figure 6C:
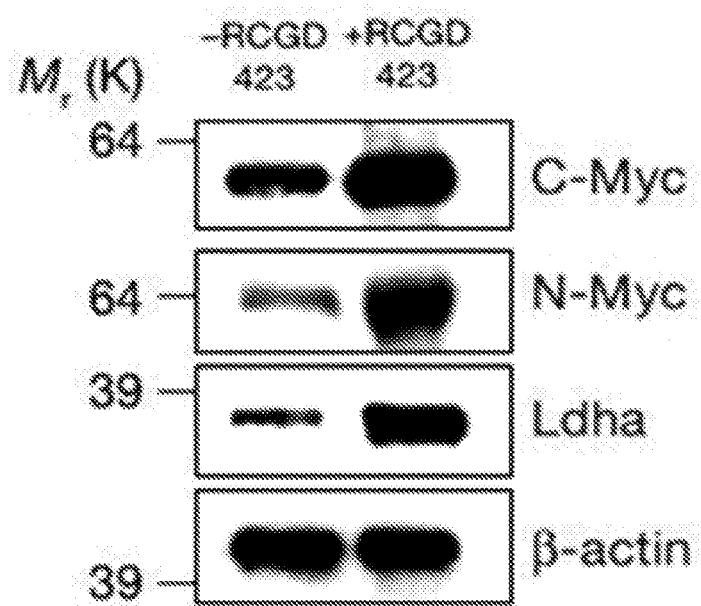
Figure 6D:
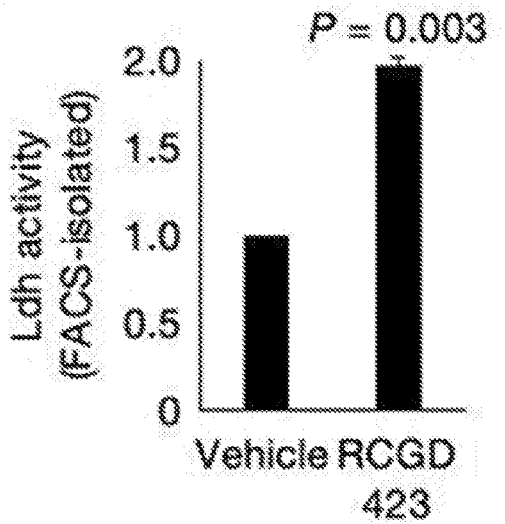
Figure 6E:
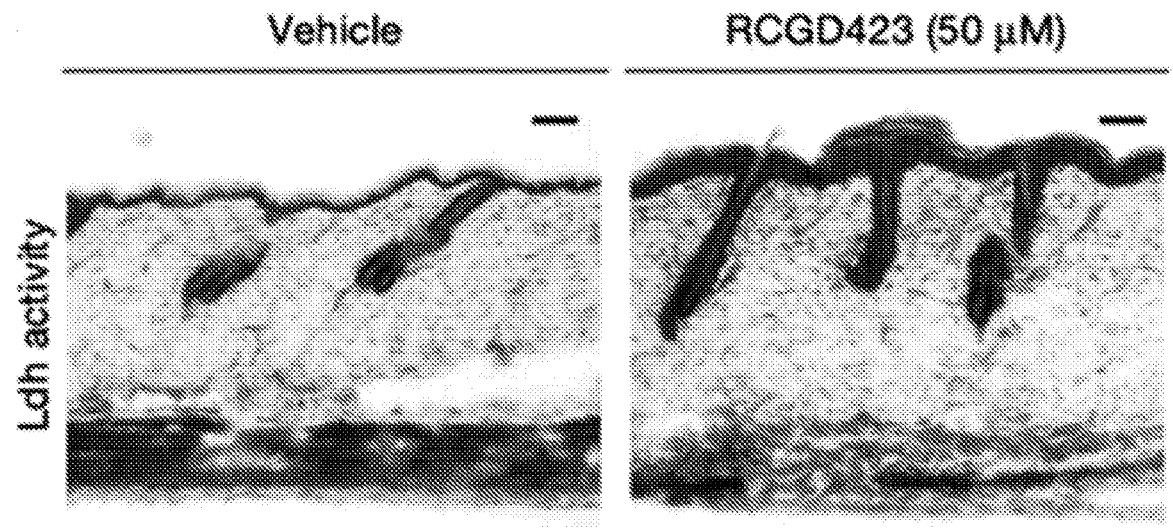
Figure 6F:
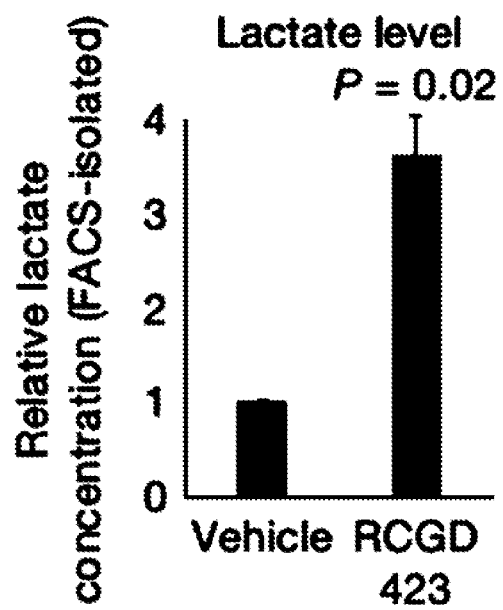

Taking advantage of a molecule with the robust ability to promote Myc expression through binding of GP130 and activation of Jak/Stat signaling, we topically treated mice for 48 hours to determine the effect of RCGD423 on Stat signaling and Myc expression. We found that RCGD423 (e.g., MPA-1/RCGD 423F) induced levels of both c-Myc and n-Myc as well as Ldha (FIG. 6C), consistent with activation of Stat3 signaling leading to induction of Myc and Ldha protein expression. In vitro measurement of Ldh activity on lysates from total epidermis showed an increase in activity by RCGD423 (FIG. 6D). In situ staining for Ldh activity showed a strong induction upon treatment with RCGD423 in both the epidermis and even in the dermis, as expected with topical treatment (FIG. 6E). LC-MS-based metabolomics on epidermis isolated from vehicle or RCGD423 showed a large increase in lactate as well, even after just 48 hours (FIG. 6F).

Figure 5:
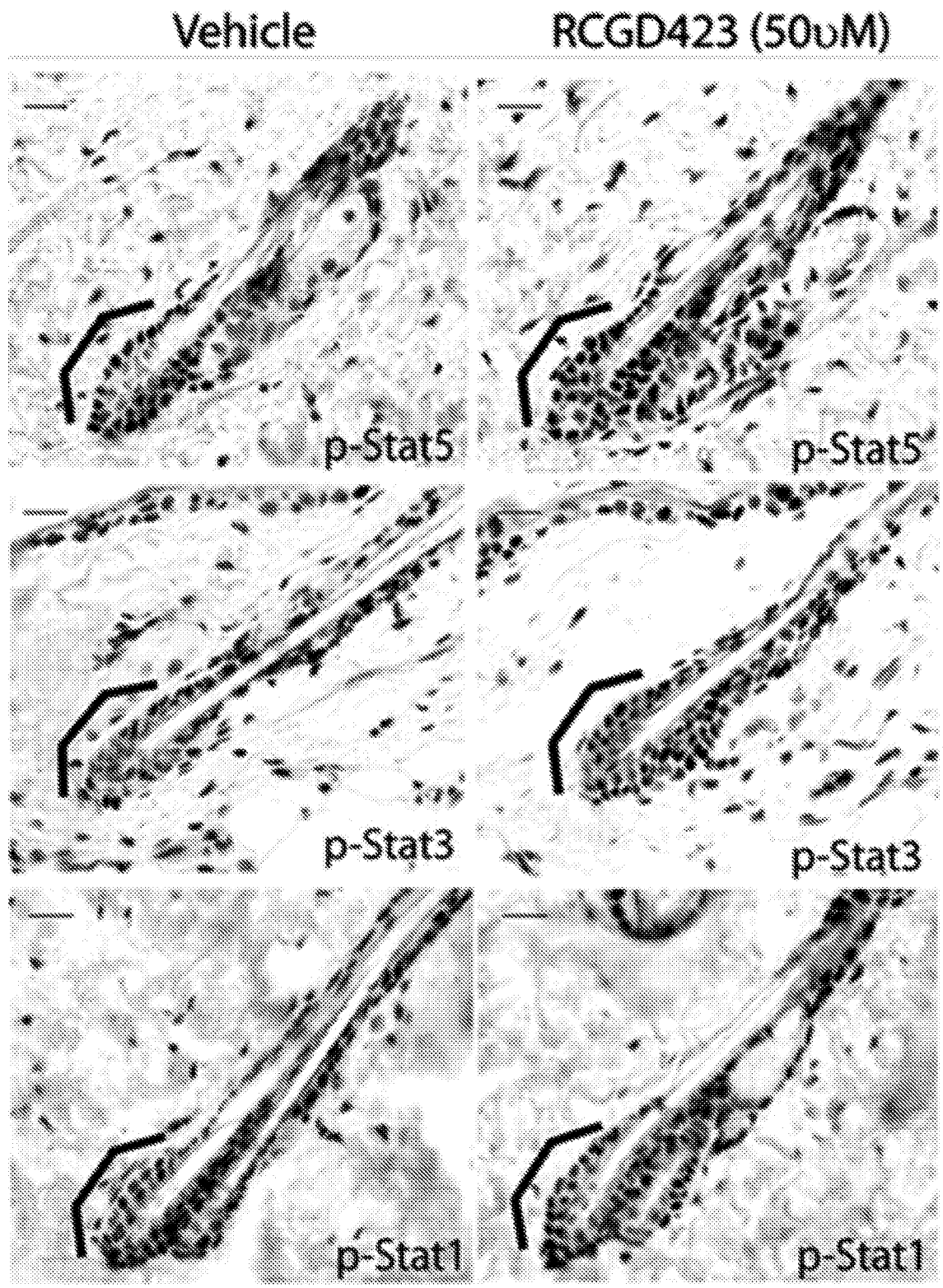
FIG. 5. Stimulation of Jak-Stat signaling and the hair cycle. RCGD423 was applied topically to shaved mice at day 50. 48 hours after treatment, the skin was harvested and prepared for IHC. IHC with the indicated antibodies demonstrates relative activity of Stat signaling in vehicle vs RCGD423 treated skin. Scale bars indicate 20 micrometers.
Figure 6G:
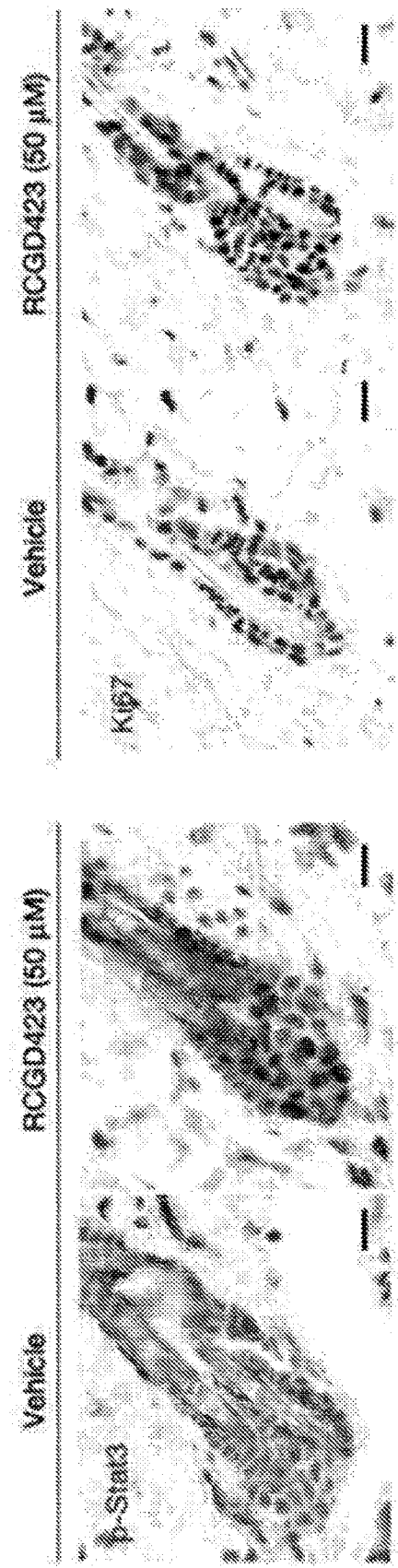
Figure 6H:
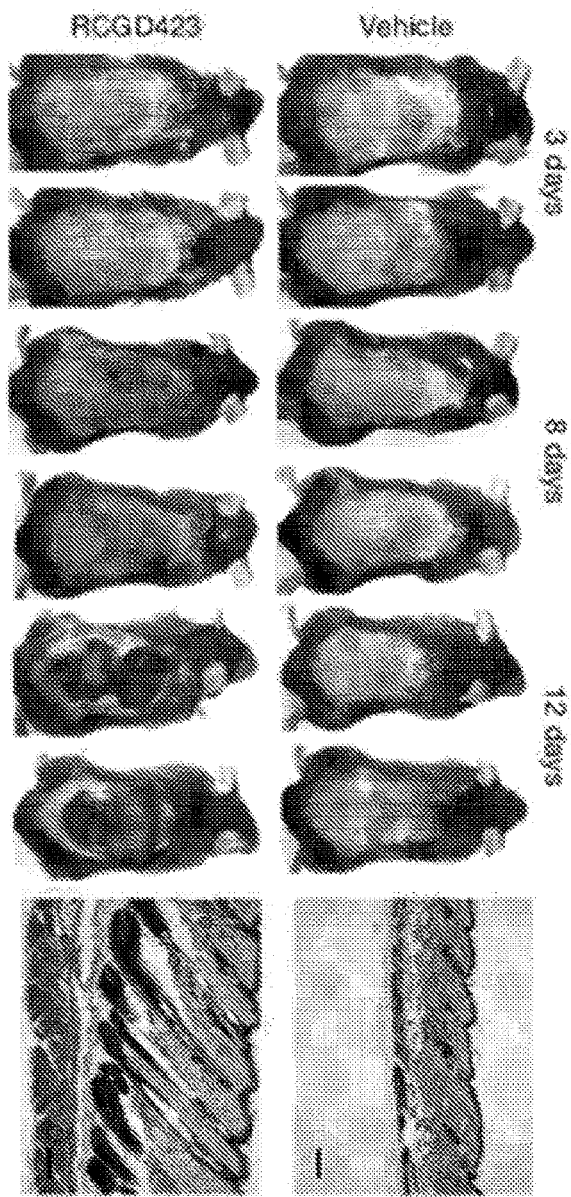
Figure 6H:
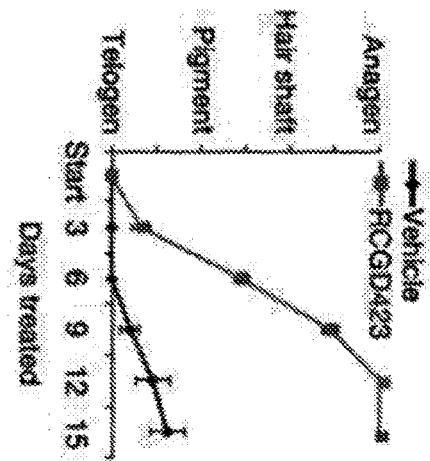

RCGD423 binds to GP130, a co-receptor for Jak-Stat signaling, and activates Stat-3. We found that Stat-3 was activated in HFSCs by RCGD423 after topical treatment by immunostaining with phospho-Stat3 antibody (FIG. 6G). This also correlated with induction of Ki-67 in HFSCs in the same tissue (FIG. 6G). IHC for pStat1 and pStat5 suggested that RCGD423 does not dramatically affect these other Stat family members (FIG. 5). Topical treatment of animals in telogen (day 50) with RCGD423 led to a robust acceleration of the hair cycle (FIG. 6H), as well as minor hyperproliferation of the interfollicular epidermis.

Together, these data demonstrate that the production of lactate, through Ldha, is important for HFSC activation, and that HFSCs may maintain a high capacity for glycolytic metabolism at least in part through the activity of Myc. Our data also demonstrate that a genetic or pharmacological disruption of lactate production can be exploited to regulate the activity of HFSCs. It is possible that these results have implications for adult stem cells in other tissues. In an accompanying manuscript, the Rutter lab describes a role for Mpc1 in adult intestinal stem cells. Consistent with data presented here on HFSCs, deletion of Mpc1 led to an increase in the ability of intestinal stem cells to form organoids.

Previous work showed that hematopoietic stem cells (HSCs) show higher glycolytic activity, but disruption of glycolysis in the HSCs led to activation of their cycling [7, 33-35], contrary to what we find with HFSCs. While the distinction could be biological, there are technical reasons for potential discrepancies as well. First, there are no Cre transgenic lines that can delete genes specifically in HSCs, as opposed to HFSCs (K15+ or Lgr5+). Second, to block glycolysis in HSCs, the previous study deleted PDK enzyme, which would only indirectly regulate glycolysis, whereas here we deleted Ldh enzyme specifically. In addition, HSCs and HFSCs are functionally distinct in that HFSCs only cycle at well-defined moments (telogen to anagen transition), while the timing of HSC activation is not as well established or synchronized. Instead, we hypothesize that increased glycolytic rate in HFSCs allows them to respond quickly to the barrage of cues that orchestrate the onset of a new hair cycle. This has also been proposed to be the case for neural stem cells based solely on RNA-seq data [36], but as of yet no in vivo functional evidence exists to confirm this possibility.

The fact that small molecules could be used to promote HFSC activation suggests that they could be useful for regenerative medicine. This is not only the case for hair growth, but potentially for wound healing as well. While HFSCs do not normally contribute to the interfollicular epidermis, in a wound setting, HFSCs migrate towards the wound site and make a contribution, as measured by lineage tracing [44].

Example 2. Materials and Methods

Mice. Animals were acquired from Jackson Labs (K15-CrePR, Lgr5-CreER and Lgr6-CreER), Rutter Lab (Mpc$^{fl/fl}$) and Seth Lab [22] (Ldha$^{fl/fl}$) and maintained under conditions set forth by IUCUC and ARC. For experiments that include analysis of the telogen stage of the hair cycle, animals were harvested at post-natal day 50, for telogen-anagen transition animals were harvested at day 70, and for anagen animals were harvested at post-natal day 90. For experiments that include analysis of transgenic animals, K15-CrePR animals were shaved and treated by intraperitoneal injections of mifepristone and Lgr5-CreER and Lgr6-CreER animals were shaved and treated with tamoxifen (10 mg/ml dissolved in sunflower seed oil, 2 mg per day for 3 days) during telogen (post-natal day 50), and monitored for hair regrowth following shaving. For FIGS. 6A-6G, wild-type C57BL/6J animals were shaved at post-natal day 50 and treated topically with Transderma Plo Gel Ultramax Base (TR220) (vehicle) or RCGD423 (50 uM) for indicated periods of time. Both male and female animals were used in this study in approximately equal numbers with no apparent difference in phenotype between genders. All phenotypes described are representative of a minimum of n=3 littermate pairs as indicated in the description of each experiment. No statistical measure was used to determine the sample size beforehand, nor were statistics used to measure effects, as the results were essentially positive or negative as represented in the figures. The results described include data from all treated animals. The investigators were not blinded to allocation during the experimental data collection, nor were the experiments randomized. The results shown were representative images from at least three independently treated animals, and genotyping was performed both before and after animal treatment for confirmation.

Histology, Immunostaining and Immunoblotting. Tissues were isolated from the indicated genotypes and embedded fresh in OCT compound for frozen tissue preparations, or fixed overnight in 4% formalin and embedded in paraffin. For frozen tissue, sectioning was performed on a Leica 3200 Cryostat, and fixed for 5 minutes in 4% paraformaldehyde. Paraffin embedded tissue was sectioned, de-paraffinized, and prepared for histology. All sections prepared for staining were blocked in staining buffer containing appropriate control IgG (Goat, Rabbit etc.). Immunohisto-chemistry was performed on formalin-fixed paraffin-embedded tissue with citrate or Tris buffer antigen retrieval with the following antibodies: Ki67 (Abcam ab16667, 1:50), p-S6 (Cell Signaling CST2215, 1:50), Sox9 (Abcam ab185230, 1:1000), Ldha (Abcam ab47010, 1:100), Ldh (Abcam ab125683, 1:100), p-Stat3 (Abcam ab68153, 1:200), p-Stat1 (Abcam ab109461, 1:200), p-Stat5 (Abcam ab32364; 1:50), Gli3 (Abcam ab6050; 1:100), β-catenin (Abcam ab32572; 1:500). The DAKO En Vision+ HRP Peroxidase System (Dako K400911-2) and Dako AEC Substrate Chromogen (Dako K346430-2) was used for detection. Images were collected on an Olympus BX43 Upright Microscope and Zeiss Model Axio Imager M1 Upright Fluorescence Microscope. Protein samples for western blots and enzymatic assays were extracted from FACS sorted epidermal populations in RIPA lysis buffer (Pierce) with Halt protease and phosphatase inhibitors (Thermo-Fisher) and precipitated in acetone for concentration. The following antibodies were used: 3-actin (Abcam ab8227; 1:1000), β-actin (Santa Cruz sc-47778; 1:1000), C-Myc (Abcam ab32072; 1:1000), N-Myc (Santa Cruz sc-53993; 1:200), H3K27Ac (Abcam ab177178; 1:200), Mpc1(Sigma HPA045119).

Cell isolation and FACS. Whole dorsal and ventral mouse skin were excised and floated on trypsin (0.25%) for 1 h at 370 or overnight at 40. The epidermis was separated from dermis by scraping, and epidermal cells were mechanically dissociated using a pipette. Epidermal cells were filtered with a 70 μM cell strainer into 20% BCS, collected at 300 g and washed twice with PBS. The cells were then filtered through a 40 μM cell strainer and stained for FACS processing with CD34 Monoclonal Antibody (RAM34), FITC, EBIOSCIENCE™ (Catalog #: 11-0341-82) and CD49d (Integrin alpha 4) Monoclonal Antibody (R1-2), PE, EBIOSCIENCE™ (Catalog #:12-0492-81). Gating strategy shown in FIG. 7B. Cells sorted using BD FACSAria high-speed cell sorters. Single positive and double positive populations were collected into 20% BCS, RIPA lysis buffer (Thermo Scientific, Pierce), or 80% methanol for enzymatic assays, western blots or mass spec analyses respectively.

Plate-reader Ldh assay. Ldh activity was determined in cell lysates by measuring the formation of soluble XTT formazan in direct relation to production of NADH over time at 475 nm at 37° C. using a Synergy-MX plate reader (Biotek Instruments). Lysates were prepared in RIPA Buffer (Thermo Scientific Pierce). Protein content was determined using the BCA Protein Assay Kit (Thermo Scientific Pierce). 10 μg of protein were used per well. The staining solution contained 50 mM Tris buffer pH 7.4, 150 μM XTT (Sigma), 750 μM NAD (Sigma), 80 μM phenazine methosulfate (Sigma) and 10 mM of substrate lactate (Sigma). Ldh activity was determined in cell lysates by measuring the change in absorbance of their common substrate or product, NADH, over time at 340 nm at 25° C. using a Synergy-MX plate reader (Biotek Instruments).

In situ Ldh assay. Cryostat sections of mouse skin were briefly fixed (4% formalin for 5 min), washed with PBS pH 7.4, and then incubated with the appropriate solution for LDH activity. Staining medium contained 50 mM Tris pH 7.4, 750 µM NAD (Sigma), 80 µM phenazine methosulfate (Sigma), 600 µM Nitrotetrazolium Blue chloride (Sigma), 10 mM MgCl2 (Sigma) and 10 mM of the substrate lactate (Sigma). Slides were incubated with staining medium at 37° C. until they reached the desired intensity, then counterstained using Nuclear Fast Red (Vector, Burlingame, Calif.) and mounted using VectaMount (Vector, Burlingame, Calif.). Control reactions were performed by using incubation medium that lacked the substrate mixture or NAD.

Mass spectrometry-based metabolomics analysis. The experiments were performed as described in [1]. To extract intracellular metabolites, FACS sorted cells were briefly rinsed with cold 150 mM ammonium acetate (pH 7.3), followed by addition of 1 ml cold 80% MeOH on dry ice. Cell suspensions were transferred into Eppendorf tubes and 10 nmol D/L-norvaline was added. After rigorously mixing, the suspension was pelleted by centrifugation ($1.3*10^4$ rpm, 4° C.). The supernatant was transferred into a glass vial, metabolites dried down under vacuum, and resuspended in 70% acetonitrile. For the mass spectrometry-based analysis of the sample, 5 ul was injected onto a Luna NH2 (150 mm×2 mm, Phenomenex) column. The samples were analyzed with an UltiMate 3000RSLC (Thermo Scientific) coupled to a Q Exactive mass spectrometer (Thermo Scientific). The Q Exactive was run with polarity switching (+3.50 kV/−3.50 kV) in full scan mode with an m/z range of 65-975. Separation was achieved using A) 5 mM $NH_4AcO$ (pH 9.9) and B) ACN. The gradient started with 15% A) going to 90% A) over 18 min, followed by an isocratic step for 9 min and reversal to the initial 15% A) for 7 min. Metabolites were quantified with TraceFinder 3.3 using accurate mass measurements (<3 ppm) and retention times.

Statistics. Both male and female animals were used in this study in approximately equal numbers with no apparent difference in phenotype between genders. All phenotypes described are representative of a minimum of n=3 littermate pairs as indicated in the description of each experiment. For analysis of hair regrowth phenotype no statistical measure was used to determine the sample size beforehand, nor were statistics used to measure effects, as the results were essentially positive or negative as represented in the figures. The results described include data from all treated animals. The investigators were not blinded to allocation during the experimental data collection, nor were the experiments randomized. All results shown were representative images from at least three independently treated animals, and genotyping was performed both before and after animal treatment for confirmation. For graphs, all comparisons are shown by Student's two-tailed unpaired t-test and all graphs, bars or lines indicate mean and error bars indicate Standard error of the mean (S.E.M.).

REFERENCES

[1] Hsu, Y. C., Pasolli, H. A. & Fuchs, E. Dynamics between stem cells, niche, and progeny in the hair follicle. Cell 144, 92-105, doi:10.1016/j.cell.2010.11.049 (2011); [2] Morris, R. J. & Potten, C. S. Highly persistent label-retaining cells in the hair follicles of mice and their fate following induction of anagen. J Invest Dermatol 112, 470-475 (1999); [3] Fuchs, E. The tortoise and the hair: slow-cycling cells in the stem cell race. Cell 137, 811-819, doi:10.1016/j.cell.2009.05.002 (2009); [4] Fuchs, E., Merrill, B. J., Jamora, C. & DasGupta, R. At the roots of a never-ending cycle. Dev Cell 1, 13-25 (2001); [5] Folmes, C. D. et al. Somatic oxidative bioenergetics transitions into pluripotency-dependent glycolysis to facilitate nuclear reprogramming. Cell Metab 14, 264-271, doi:10.1016/j.cmet.2011.06.011 (2011); [6] Suda, T., Takubo, K. & Semenza, G. L. Metabolic regulation of hematopoietic stem cells in the hypoxic niche. Cell Stem Cell 9, 298-310, doi:10.1016/j.stem.2011.09.010 (2011); [7] Simsek, T. et al. The distinct metabolic profile of hematopoietic stem cells reflects their location in a hypoxic niche. Cell Stem Cell 7, 380-390, doi:10.1016/j.stem.2010.07.011 (2010); [8] Kloepper, J. E. et al. Mitochondrial function in murine skin epithelium is crucial for hair follicle morphogenesis and epithelial-mesenchymal interactions. J Invest Dermatol 135, 679-689, doi:10.1038/jid.2014.475 (2015); [9] Hamanaka, R. B. & Chandel, N. S. Mitochondrial metabolism as a regulator of keratinocyte differentiation. Cell Logist 3, e25456, doi:10.4161/cl.25456 (2013); [10] Hamanaka, R. B. et al. Mitochondrial reactive oxygen species promote epidermal differentiation and hair follicle development. Sci Signal 6, ra8, doi:10.1126/scisignal.2003638 (2013); [11] Baris, O. R. et al. The mitochondrial electron transport chain is dispensable for proliferation and differentiation of epidermal progenitor cells. Stem Cells 29, 1459-1468, doi:10.1002/stem.695 (2011); [12] Blanpain, C., Lowry, W. E., Geoghegan, A., Polak, L. & Fuchs, E. Self-renewal, multipotency, and the existence of two cell populations within an epithelial stem cell niche. Cell 118, 635-648 (2004); [13] Tumbar, T. et al. Defining the epithelial stem cell niche in skin. Science 303, 359-363 (2004); [14] Morris, R. J. et al. Capturing and profiling adult hair follicle stem cells. Nat Biotechnol 22, 411-417 (2004); [15] Trempus, C. S. et al. Enrichment for living murine keratinocytes from the hair follicle bulge with the cell surface marker CD34. J Invest Dermatol 120, 501-511 (2003); [16] Nguyen, H., Rendl, M. & Fuchs, E. Tcf3 governs stem cell features and represses cell fate determination in skin. Cell 127, 171-183 (2006); [17] Lowry, W. E. et al. Defining the impact of beta-catenin/Tcf transactivation on epithelial stem cells. Genes Dev 19, 1596-1611 (2005); [18] Fromm, H. J. The nature of pyruvate involved in the enzymic formation of L-lactate in the rabbit-muscle lactate dehydrogenase reaction. Biochim Biophys Acta 99, 540-542 (1965); [19] Paus, R., Muller-Rover, S. & Botchkarev, V. A. Chronobiology of the hair follicle: hunting the "hair cycle clock". J Investig Dermatol Symp Proc 4, 338-345 (1999); [20] Chan, F. K., Moriwaki, K. & De Rosa, M. J. Detection of necrosis by release of lactate dehydrogenase activity. Methods Mol Biol 979, 65-70, doi:10.1007/978-1-62703-290-2_7 (2013); [21] Wang, L., Siegenthaler, J. A., Dowell, R. D. & Yi, R. Foxc1 reinforces quiescence in self-renewing hair follicle stem cells. Science 351, 613-617, doi:10.1126/science.aad5440 (2016); [22] Xie, H. et al. Targeting lactate dehydrogenase—a inhibits tumorigenesis and tumor progression in mouse models of lung cancer and impacts tumor-initiating cells. Cell Metab 19, 795-809, doi:10.1016/j.cmet.2014.03.003 (2014); [23] White, A. C. et al. Defining the origins of Ras/p53-mediated squamous cell carcinoma. Proc Natl Acad Sci USA 108, 7425-7430, doi: 1012670108 [pii] 10.1073/pnas.1012670108 (2011); [24] Jaks, V. et al. Lgr5 marks cycling, yet long-lived, hair follicle stem cells. Nat Genet 40, 1291-1299, doi:ng.239 [pii]10.1038/ng.239 (2008); [25] Kellenberger, A. J. & Tauchi, M. Mammalian target of rapamycin complex 1 (mTORC1) may modulate the timing of anagen entry in mouse hair follicles. Exp Dermatol 22, 77-80, doi:10.1111/exd.12062 (2013); [26] Bricker, D. K. et al. A mitochondrial pyruvate carrier required for pyruvate uptake in yeast, Drosophila, and humans. Science 337, 96-100, doi:10.1126/science.1218099 (2012); [27] Schell, J. C. et al. A role for the mitochondrial pyruvate carrier as a repressor of the Warburg effect and colon cancer cell growth. Mol Cell 56, 400-413, doi:10.1016/j.molcel.2014.09.026 (2014); [28] Snippert, H. J. et al. Lgr6 marks stem cells in the hair follicle that generate all cell lineages of the skin. Science 327, 1385-1389, doi:327/5971/1385 [pii]10.1126/science.1184733 (2010); [29] Patterson, J. N. et al. Mitochondrial metabolism of pyruvate is essential for regulating glucose-stimulated insulin secretion. J Biol Chem 289, 13335-13346, doi:10.1074/jbc.M113.521666 (2014); [30] Wang, N. et al. The expression and role of c-Myc in mouse hair follicle morphogenesis and cycling. Acta Histochem 114, 199-206, doi:10.1016/j.acthis.2011.04.009 (2012); [31] Bull, J. J. et al. Ectopic expression of c-Myc in the skin affects the hair growth cycle and causes an enlargement of the sebaceous gland. Br J Dermatol 152, 1125-1133, doi:10.1111/j.1365-2133.2005.06458.x (2005); [32] Zanet, J. et al. Endogenous Myc controls mammalian epidermal cell size, hyperproliferation, endoreplication and stem cell amplification. J Cell Sci 118, 1693-1704, doi:10.1242/jcs.02298 (2005); [33] Hsu, P. & Qu, C. K. Metabolic plasticity and hematopoietic stem cell biology. Curr Opin Hematol 20, 289-294, doi:10.1097/MOH.0b013e328360ab4d (2013); [34] Harris, J. M. et al. Glucose metabolism impacts the spatiotemporal onset and magnitude of HSC induction in vivo. Blood 121, 2483-2493, doi: 10.1182/blood-2012-12-471201 (2013); [35] Takubo, K. et al. Regulation of glycolysis by Pdk functions as a metabolic checkpoint for cell cycle quiescence in hematopoietic stem cells. Cell Stem Cell 12, 49-61, doi:10.1016/j.stem.2012.10.011 (2013); [36] Shin, J. et al. Single-Cell RNA-Seq with Waterfall Reveals Molecular Cascades underlying Adult Neurogenesis. Cell Stem Cell 17, 360-372, doi:10.1016/j.stem.2015.07.013 (2015); [37] Sutton, R., Cam, G. R., Ward, W. G., Raphael, K. A. & Ward, K. A. myc protooncogenes of wool and hair growth. Ann N Y Acad Sci 642, 326-338 (1991); [38] Gu, W. et al. Glycolytic Metabolism Plays a Functional Role in Regulating Human Pluripotent Stem Cell State. Cell Stem Cell 19, 476-490, doi:10.1016/j.stem.2016.08.008 (2016); [39] Folmes, C. D. et al. Nuclear reprogramming with c-Myc potentiates glycolytic capacity of derived induced pluripotent stem cells. J Cardiovasc Transl Res 6, 10-21, doi:10.1007/s12265-012-9431-2 (2013); [40] Dang, C. V., Le, A. & Gao, P. MYC-induced cancer cell energy metabolism and therapeutic opportunities. Clin Cancer Res 15, 6479-6483, doi:10.1158/1078-0432.CCR-09-0889 (2009); [41] He, T. L. et al. The c-Myc-LDHA axis positively regulates aerobic glycolysis and promotes tumor progression in pancreatic cancer. Med Oncol 32, 187, doi:10.1007/s12032-015-0633-8 (2015); [42] Nilsson, L. M. et al. Mouse genetics suggests cell-context dependency for Myc-regulated metabolic enzymes during tumorigenesis. PLoS Genet 8, e1002573, doi:10.1371/journal.pgen.1002573 (2012); [43] Kim, J. W. et al. Evaluation of myc E-box phylogenetic footprints in glycolytic genes by chromatin immunoprecipitation assays. Mol Cell Biol 24, 5923-5936, doi: 10.1128/MCB.24.13.5923-5936.2004 (2004); [44] Ito, M. et al. Stem cells in the hair follicle bulge contribute to wound repair but not to homeostasis of the epidermis. Nat Med 11, 1351-1354 (2005); [45] Subramanian, A. et al. Gene set enrichment analysis: a knowledge-based approach for interpreting genome-wide expression profiles. Proc Natl Acad Sci USA 102, 15545-15550, doi:10.1073/pnas.0506580102 (2005).

Although the invention has been described with reference to the above examples, it will be understood that modifications and variations are encompassed within the spirit and scope of the invention. Accordingly, the invention is limited only by the following claims.

What is claimed is:

1. A method for inducing hair growth or inducing hair regeneration in a subject in need thereof, the method comprising administering to the subject an effective amount of a compound of formula (III):

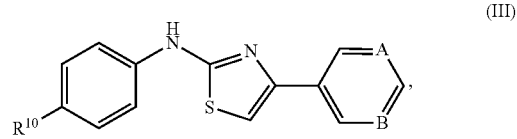

wherein:
A is CH or N;
B is CH or N; and
$R^{10}$ is halogen, hydrogen, $-CX^{10.1}{}_3$, $-CHX^{10.1}{}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
n1 is an integer from 0 to 4;
m1 is 1 or 2;
v1 is 1 or 2;
$R^{10A}$, $R^{10B}$, $R^{10C}$, and $R^{10D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10B}$ and $R^{10C}$ substituents bonded to the same nitrogen atom may optionally be joined to form a substituted or unsubstituted heterocycloalkyl or substituted or unsubstituted heteroaryl; and
$X^{10.1}$ is independently $-Cl$, $-Br$, $-I$ or $-F$.

2. The method of claim 1, wherein $R^{10}$ is halogen.

3. The method of claim 1, wherein $R^{10}$ is fluorine, chlorine, or iodine.

4. The method of claim 1, wherein the compound of formula (III) is:

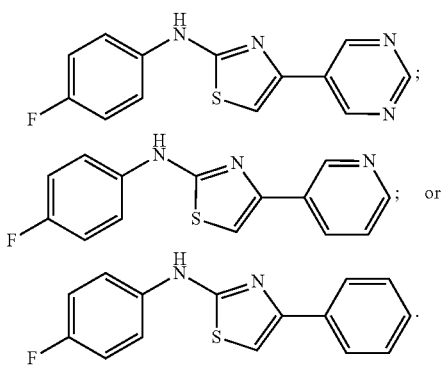

5. The method of claim 1, wherein the compound of formula (III) is:

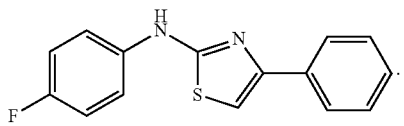

6. A method for activating a quiescent hair follicle stem cell in a subject in need thereof, the method comprising contacting a quiescent hair follicle stem cell with an effective amount of a compound of formula (III):

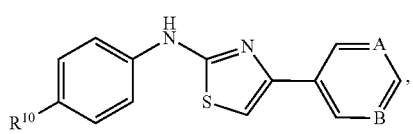

wherein:
A is CH or N;
B is CH or N; and
$R^{10}$ is halogen, hydrogen, $-CX^{10.1}_3$, $-CHX^{10.1}_2$, $-CH_2X^{10.1}$, $-CN$, $-SO_{n1}R^{10A}$, $-SO_{v1}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m1}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
n1 is an integer from 0 to 4;
m1 is 1 or 2;
v1 is 1 or 2;
$R^{10A}$, $R^{10B}$, $R^{10C}$, and $R^{10D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10B}$ and $R^{10C}$ substituents bonded to the same nitrogen atom may optionally be joined to form a substituted or unsubstituted heterocycloalkyl or substituted or unsubstituted heteroaryl; and
$X^{10.1}$ is independently $-Cl$, $-Br$, $-I$ or $-F$.

7. The method of claim 6, wherein the quiescent hair follicle stem cell is a human hair follicle stem cell.

8. The method of claim 6, wherein the subject is a human subject.

9. The method of claim 6, wherein $R^{10}$ is halogen.

10. The method of claim 6, wherein $R^{10}$ is fluorine, chlorine, or iodine.

11. The method of claim 6, wherein the compound of formula (III) is:

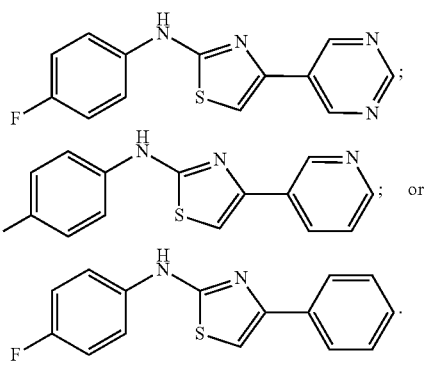

12. The method of claim 6, wherein the compound of formula (III) is:

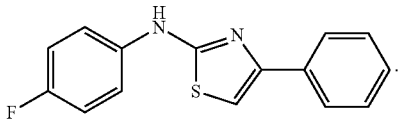 [SMILES: Fc1ccc(Nc2nc(-c3ccccc3)cs2)cc1]

13. A method for inducing glycolysis in a hair follicle stem cell or activating lactate dehydrogenase in a hair follicle stem cell, the method comprising contacting a hair follicle stem cell with an effective amount of a compound of formula (III):

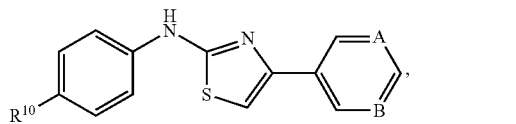

wherein:
A is CH or N; and
B is CH or N; and $R^{10}$ is halogen, hydrogen, —$CX^{10.1}_3$, —$CHX^{10.1}_2$, —$CH_2X^{10.1}$, —CN, —$SO_{n1}R^{10A}$, —$SO_{v1}NR^{10B}R^{10C}$, —$NHNR^{10B}R^{10C}$, —$ONR^{10B}R^{10C}$, —$NHC(O)NHNR^{10B}R^{10C}$, —$NHC(O)NR^{10B}R^{10C}$, —$N(O)_{m1}$, —$NR^{10B}R^{10C}$, —$C(O)R^{10D}$, —$C(O)OR^{10D}$, —$C(O)NR^{10B}R^{10C}$, —$OR^{10A}$, —$NR^{10B}SO_2R^{10A}$, —$NR^{10B}C(O)R^{10D}$, —$NR^{10B}C(O)OR^{10D}$, —$NR^{10B}OR^{10D}$, —$OCX^{10.1}_3$, —$OCHX^{10.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n1 is an integer from 0 to 4;

m1 is 1 or 2;

v1 is 1 or 2;

$R^{10A}$, $R^{10B}$, $R^{10C}$, and $R^{10D}$ are independently hydrogen, halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10B}$ and $R^{10C}$ substituents bonded to the same nitrogen atom may optionally be joined to form a substituted or unsubstituted heterocycloalkyl or substituted or unsubstituted heteroaryl; and $X^{10.1}$ is independently —Cl, —Br, —I or —F.

14. The method of claim 13, wherein the hair follicle stem cell is a quiescent hair follicle stem cell.

15. The method of claim 13, wherein a level of a glycolytic metabolite in the hair follicle stem cell is increased relative to the absence of contacting the hair follicle stem cell with the compound of formula (III).

16. The method of claim 15, wherein the glycolytic metabolite is glucose, fructose-6-phosphate, fructose-bisphosphate, dihydroxyacetone phosphate, 3-phosphoglycerate, lactate, or a combination of two or more thereof.

17. The method of claim 13, wherein $R^{10}$ is halogen.

18. The method of claim 13, wherein $R^{10}$ is fluorine, chlorine, or iodine.

19. The method of claim 13, wherein the compound of formula (III) is:

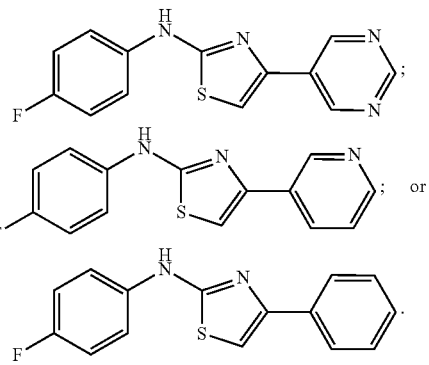

20. The method of claim 13, wherein the compound of formula (III) is:

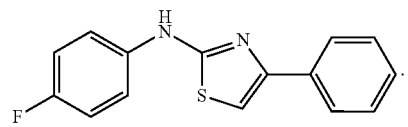 [SMILES: Fc1ccc(Nc2nc(-c3ccccc3)cs2)cc1]

21. The method of claim 6, wherein the effective amount of the compound of Formula (III) is contained in a formulation for topical administration to a skin surface.

22. The method of claim 9, wherein the method for activating a quiescent hair follicle stem cell is a method for healing a wound.

* * * * *